United States Patent
Kim et al.

(10) Patent No.: US 9,850,537 B2
(45) Date of Patent: Dec. 26, 2017

(54) BIOMARKER TFF1 FOR PREDICTING EFFECT OF C-MET INHIBITOR

(71) Applicant: Samsung Electronics Co., Ltd., Suwon-si, Gyeonggi-do (KR)

(72) Inventors: Bo Gyou Kim, Seoul (KR); Eunjin Lee, Yongin-si (KR); Kyung Ah Kim, Seongnam-si (KR); Tae Jin Ahn, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/604,361

(22) Filed: Jan. 23, 2015

(65) Prior Publication Data

US 2015/0212077 A1    Jul. 30, 2015

(30) Foreign Application Priority Data

Jan. 24, 2014 (KR) .................. 10-2014-0008733

(51) Int. Cl.
| | | |
|---|---|---|
| A61K 39/00 | (2006.01) | |
| C12Q 1/68 | (2006.01) | |
| C07K 16/28 | (2006.01) | |
| C07K 16/30 | (2006.01) | |
| A61K 39/395 | (2006.01) | |
| A61K 45/06 | (2006.01) | |
| G01N 33/574 | (2006.01) | |

(52) U.S. Cl.
CPC ...... *C12Q 1/6876* (2013.01); *A61K 39/39558* (2013.01); *A61K 45/06* (2013.01); *C07K 16/2863* (2013.01); *C07K 16/3023* (2013.01); *C07K 16/3046* (2013.01); *C12Q 1/6886* (2013.01); *G01N 33/574* (2013.01); *A61K 2039/505* (2013.01); *C07K 2317/24* (2013.01); *C07K 2317/622* (2013.01); *C07K 2317/73* (2013.01); *C07K 2317/76* (2013.01); *C07K 2319/30* (2013.01); *C07K 2319/32* (2013.01); *C12Q 2600/106* (2013.01); *C12Q 2600/158* (2013.01); *G01N 2333/47* (2013.01); *G01N 2800/52* (2013.01)

(58) Field of Classification Search
None
See application file for complete search history.

(56) References Cited

U.S. PATENT DOCUMENTS

| | | |
|---|---|---|
| 2005/0064455 A1 | 3/2005 | Baker et al. |
| 2009/0269736 A1 | 10/2009 | Nimmrich et al. |
| 2009/0311193 A1 | 12/2009 | Mauro et al. |
| 2012/0225433 A1 | 9/2012 | Cobleigh et al. |
| 2012/0253160 A1 | 10/2012 | Mauro et al. |

FOREIGN PATENT DOCUMENTS

WO    WO 2007-109809 A    9/2007

OTHER PUBLICATIONS

Kirikoshi et al, Inter J Onco, 21:655-659, 2002.*
Affymetrix, GeneChip 3' IVT Plus Reagent Kit, User Manual: pp. 1-45 (2013).

* cited by examiner

*Primary Examiner* — Lei Yao
(74) *Attorney, Agent, or Firm* — Leydig, Voit & Mayer, Ltd.

(57) ABSTRACT

A method of predicting an effect of a c-Met inhibitor and/or selecting a subject for application of a c-Met inhibitor using TFF1, a method of monitoring an effect of a c-Met inhibitor using TFF1, and a method of treating and/or preventing cancer including administering a c-Met inhibitor to the selected subject.

7 Claims, 10 Drawing Sheets

SEQUENCE LISTING

```
<160> NUMBER OF SEQ ID NOS: 125

<210> SEQ ID NO 1
<211> LENGTH: 5
<212> TYPE: PRT
<213> ORGANISM: Artificial Sequence
<220> FEATURE:
<223> OTHER INFORMATION: Synthetic heavy chain CDR1 of AbF46

<400> SEQUENCE: 1

Asp Tyr Tyr Met Ser
 1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic heavy chain CDR2 of AbF46

<400> SEQUENCE: 2

Phe Ile Arg Asn Lys Ala Asn Gly Tyr Thr Thr Glu Tyr Ser Ala Ser
 1               5                  10                  15

Val Lys Gly
```

```
<210> SEQ ID NO 3
<211> LENGTH: 6
<212> TYPE: PRT
<213> ORGANISM: Artificial Sequence
<220> FEATURE:
<223> OTHER INFORMATION: Synthetic heavy chain CDR3 of AbF46

<400> SEQUENCE: 3

Asp Asn Trp Phe Ala Tyr
  1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic heavy chain CDR1 of c-Met antibody
<220> FEATURE:
<221> NAME/KEY: MOD_RES
<222> LOCATION: (1)
<223> OTHER INFORMATION: Xaa is Pro or Ser or absent
<220> FEATURE:
<221> NAME/KEY: MOD_RES
<222> LOCATION: (2)
<223> OTHER INFORMATION: Xaa is Glu or Asp

<400> SEQUENCE: 4

Xaa Xaa Tyr Tyr Met Ser
  1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic heavy chain CDR2 of c-Met antibody
<220> FEATURE:
<221> NAME/KEY: MOD_RES
<222> LOCATION: (3)
<223> OTHER INFORMATION: Xaa is Asn or Lys
<220> FEATURE:
<221> NAME/KEY: MOD_RES
<222> LOCATION: (4)
<223> OTHER INFORMATION: Xaa is Ala or Val
<220> FEATURE:
<221> NAME/KEY: MOD_RES
<222> LOCATION: (7)
<223> OTHER INFORMATION: Xaa is Asn or Thr

<400> SEQUENCE: 5

Arg Asn Xaa Xaa Asn Gly Xaa Thr
  1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic heavy chain CDR3 of c-Met antibody
<220> FEATURE:
<221> NAME/KEY: MOD_RES
<222> LOCATION: (5)
<223> OTHER INFORMATION: X is Ser or Thr

<400> SEQUENCE: 6

Asp Asn Trp Leu Xaa Tyr
  1               5

<210> SEQ ID NO 7
<211> LENGTH: 17
```

```
<212> TYPE: PRT
<213> ORGANISM: Artificial Sequence
<220> FEATURE:
<223> OTHER INFORMATION: Synthetic light chain CDR1 of c-Met antibody
<220> FEATURE:
<221> NAME/KEY: MOD_RES
<222> LOCATION: (4)
<223> OTHER INFORMATION: Xaa is His, Arg, Gln or Lys
<220> FEATURE:
<221> NAME/KEY: MOD_RES
<222> LOCATION: (9)
<223> OTHER INFORMATION: Xaa is Ser or Trp
<220> FEATURE:
<221> NAME/KEY: MOD_RES
<222> LOCATION: (12)
<223> OTHER INFORMATION: Xaa is His or Gln
<220> FEATURE:
<221> NAME/KEY: MOD_RES
<222> LOCATION: (13)
<223> OTHER INFORMATION: Xaa is Lys or Asn

<400> SEQUENCE: 7

Lys Ser Ser Xaa Ser Leu Leu Ala Xaa Gly Asn Xaa Xaa Asn Tyr Leu
 1               5                  10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic light chain CDR2 of c-Met antibody
<220> FEATURE:
<221> NAME/KEY: MOD_RES
<222> LOCATION: (2)
<223> OTHER INFORMATION: Xaa is Ala or Gly
<220> FEATURE:
<221> NAME/KEY: MOD_RES
<222> LOCATION: (4)
<223> OTHER INFORMATION: Xaa is Thr or Lys
<220> FEATURE:
<221> NAME/KEY: MOD_RES
<222> LOCATION: (7)
<223> OTHER INFORMATION: Xaa is Ser or Pro

<400> SEQUENCE: 8

Trp Xaa Ser Xaa Arg Val Xaa
 1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic light chain CDR3 of c-Met antibody
<220> FEATURE:
<221> NAME/KEY: MOD_RES
<222> LOCATION: (1)
<223> OTHER INFORMATION: Xaa is Gly, Ala or Gln
<220> FEATURE:
<221> NAME/KEY: MOD_RES
<222> LOCATION: (6)
<223> OTHER INFORMATION: Xaa is Arg, His, Ser, Ala, Gly or Lys
<220> FEATURE:
<221> NAME/KEY: MOD_RES
<222> LOCATION: (8)
<223> OTHER INFORMATION: Xaa is Leu, Tyr, Phe or Met

<400> SEQUENCE: 9

Xaa Gln Ser Tyr Ser Xaa Pro Xaa Thr
 1               5
```

```
<210> SEQ ID NO 10
<211> LENGTH: 17
<212> TYPE: PRT
<213> ORGANISM: Artificial Sequence
<220> FEATURE:
<223> OTHER INFORMATION: Synthetic light chain CDR1 of AbF46

<400> SEQUENCE: 10

Lys Ser Ser Gln Ser Leu Leu Ala Ser Gly Asn Gln Asn Asn Tyr Leu
 1               5                  10                  15
Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic light chain CDR2 of AbF46

<400> SEQUENCE: 11

Trp Ala Ser Thr Arg Val Ser
 1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic light chain CDR3 of AbF46

<400> SEQUENCE: 12

Gln Gln Ser Tyr Ser Ala Pro Leu Thr
 1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic CDR-L3 derived from L3-1 clone

<400> SEQUENCE: 13

Gln Gln Ser Tyr Ser Arg Pro Tyr Thr
 1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic CDR-L3 derived from L3-2 clone

<400> SEQUENCE: 14

Gly Gln Ser Tyr Ser Arg Pro Leu Thr
 1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic CDR-L3 derived from L3-3 clone

<400> SEQUENCE: 15

Ala Gln Ser Tyr Ser His Pro Phe Ser
 1               5
```

```
<210> SEQ ID NO 16
<211> LENGTH: 9
<212> TYPE: PRT
<213> ORGANISM: Artificial Sequence
<220> FEATURE:
<223> OTHER INFORMATION: Synthetic CDR-L3 derived from L3-5 clone

<400> SEQUENCE: 16

Gln Gln Ser Tyr Ser Arg Pro Phe Thr
  1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic heavy chain variable region of anti
      c-Met humanized antibody(huAbF46-H4)

<400> SEQUENCE: 17

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser
            115

<210> SEQ ID NO 18
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 18

Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110
```

<210> SEQ ID NO 19
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 19

```
Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
                 20                  25                  30

Gly Asn Gln Asn Asn Tyr Leu Ala Trp His Gln Gln Lys Pro Gly Lys
             35                  40                  45

Ala Pro Lys Met Leu Ile Ile Trp Ala Ser Thr Arg Val Ser Gly Val
         50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gly Gln
                 85                  90                  95

Ser Tyr Ser Arg Pro Leu Thr Phe Gly Gln Gly Thr Lys Val Glu Ile
                100                 105                 110

Lys Arg
```

<210> SEQ ID NO 20
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 20

```
Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
                 20                  25                  30

Gly Asn Gln Asn Asn Tyr Leu Ala Trp His Gln Gln Lys Pro Gly Lys
             35                  40                  45

Ala Pro Lys Met Leu Ile Ile Trp Ala Ser Thr Arg Val Ser Gly Val
         50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Ala Gln
                 85                  90                  95

Ser Tyr Ser His Pro Phe Ser Phe Gly Gln Gly Thr Lys Val Glu Ile
                100                 105                 110

Lys Arg
```

<210> SEQ ID NO 21
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Phe Thr Phe Gly Gln Gly Thr Lys Val Glu Ile
            100                 105                 110

Lys Arg

<210> SEQ ID NO 22
<211> LENGTH: 6
<212> TYPE: PRT
<213> ORGANISM: Artificial Sequence
<220> FEATURE:
<223> OTHER INFORMATION: Synthetic CDR-H1 derived from H11-4 clone

<400> SEQUENCE: 22

Pro Glu Tyr Tyr Met Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic CDR-H1 derived from YC151 clone

<400> SEQUENCE: 23

Pro Asp Tyr Tyr Met Ser
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic CDR-H1 derived from YC193 clone

<400> SEQUENCE: 24

Ser Asp Tyr Tyr Met Ser
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic CDR-H2 derived from YC244 clone

<400> SEQUENCE: 25

Arg Asn Asn Ala Asn Gly Asn Thr
1               5

-continued

```
<210> SEQ ID NO 26
<211> LENGTH: 8
<212> TYPE: PRT
<213> ORGANISM: Artificial Sequence
<220> FEATURE:
<223> OTHER INFORMATION: Synthetic CDR-H2 derived from YC321 clone

<400> SEQUENCE: 26

Arg Asn Lys Val Asn Gly Tyr Thr
 1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic CDR-H3 derived from YC354 clone

<400> SEQUENCE: 27

Asp Asn Trp Leu Ser Tyr
 1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic CDR-H3 derived from YC374 clone

<400> SEQUENCE: 28

Asp Asn Trp Leu Thr Tyr
 1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic CDR-L1 derived from L1-1 clone

<400> SEQUENCE: 29

Lys Ser Ser His Ser Leu Leu Ala Ser Gly Asn Gln Asn Asn Tyr Leu
 1               5                  10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic CDR-L1 derived from L1-3 clone

<400> SEQUENCE: 30

Lys Ser Ser Arg Ser Leu Leu Ser Ser Gly Asn His Lys Asn Tyr Leu
 1               5                  10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic CDR-L1 derived from L1-4 clone

<400> SEQUENCE: 31

Lys Ser Ser Lys Ser Leu Leu Ala Ser Gly Asn Gln Asn Asn Tyr Leu
```

<210> SEQ ID NO 32
<211> LENGTH: 17
<212> TYPE: PRT
<213> ORGANISM: Artificial Sequence
<220> FEATURE:
<223> OTHER INFORMATION: Synthetic CDR-L1 derived from L1-12 clone

<400> SEQUENCE: 32

Lys Ser Ser Arg Ser Leu Leu Ala Ser Gly Asn Gln Asn Asn Tyr Leu
 1               5                   10                  15
Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic CDR-L1 derived from L1-22 clone

<400> SEQUENCE: 33

Lys Ser Ser His Ser Leu Leu Ala Ser Gly Asn Gln Asn Asn Tyr Leu
 1               5                   10                  15
Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic CDR-L2 derived from L2-9 clone

<400> SEQUENCE: 34

Trp Ala Ser Lys Arg Val Ser
 1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic CDR-L2 derived from L2-12 clone

<400> SEQUENCE: 35

Trp Gly Ser Thr Arg Val Ser
 1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic CDR-L2 derived from L2-16 clone

<400> SEQUENCE: 36

Trp Gly Ser Thr Arg Val Pro
 1               5

<210> SEQ ID NO 37
<211> LENGTH: 9
<212> TYPE: PRT
<213> ORGANISM: Artificial Sequence
<220> FEATURE:

<223> OTHER INFORMATION: Synthetic CDR-L3 derived from L3-32 clone

<400> SEQUENCE: 37

Gln Gln Ser Tyr Ser Lys Pro Phe Thr
 1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 38

```
gaattcgccg ccaccatgga atggagctgg gttttctcg taacactttt aaatggtatc      60
cagtgtgagg tgaagctggt ggagtctgga ggaggcttgg tacagcctgg ggttctctg     120 agactctcct gtgcaacttc tgggttcacc ttcactgatt actacatgag ctgggtccgc    180
cagcctccag aaaggcact tgagtggttg ggttttatta aaacaaagc taatggttac      240 acaacagagt acagtgcatc tgtgaagggt cggttcacca tctccagaga taattcccaa    300
agcatcctct atcttcaaat ggacaccctg agagctgagg acagtgccac ttattactgt    360
gcaagagata actggtttgc ttactgggc aagggactc tggtcactgt ctctgcagct      420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg gacccctgag    840
gtcacatgcg tggtggtgga cgtgagccca agaccctg aggtcaagtt caactggtac       900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
```

```
tacaagtgca aggtctccaa caaagccctc ccagcccca tcgagaaaac catctccaaa    1080 gccaagggc agccccgaga accacaggtg tacaccctgc ccccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga ctcgag                               1416
```

<210> SEQ ID NO 39
<211> LENGTH: 759
<212> TYPE: DNA
<213> ORGANISM: Artificial Sequence
<220> FEATURE:
<223> OTHER INFORMATION: Synthetic nucleotide sequence of light chain of chAbF46
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39

```
gaattcacta gtgattaatt cgccgccacc atggattcac aggcccaggt cctcatgttg     60
ctgctgctat cggtatctgg tacctgtgga gacattttga tgacccagtc tccatcctcc    120
ctgactgtgt cagcaggaga gaaggtcact atgagctgca agtccagtca gagtctttta    180
gctagtggca accaaaataa ctacttggcc tggcaccagc agaaaccagg acgatctcct    240
aaaatgctga taatttgggc atccactagg gtatctggag tccctgatcg cttcataggc    300
agtggatctg ggacggattt cactctgacc atcaacagtg tgcaggctga agatctggct    360
gtttattact gtcagcagtc ctacagcgct ccgctcacgt tcggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga aacacaaagt ctacgcctgc gaagtcaccc atcagggcct gagctcgccc    720
gtcacaaaga gcttcaacag gggagagtgt tgactcgag                            759
```

<210> SEQ ID NO 40
<211> LENGTH: 447
<212> TYPE: PRT
<213> ORGANISM: Artificial Sequence
<220> FEATURE:
<223> OTHER INFORMATION: Synthetic amino acid sequence of H1-heavy

<400> SEQUENCE: 40

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365
```

```
Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445
```

<210> SEQ ID NO 41
<211> LENGTH: 447
<212> TYPE: PRT
<213> ORGANISM: Artificial Sequence
<220> FEATURE:
<223> OTHER INFORMATION: Synthetic amino acid sequence of H3-heavy

<400> SEQUENCE: 41

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

```
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic amino acid sequence of H4-heavy

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic amino acid sequence of H1-light

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic amino acid sequence of H2-light

<400> SEQUENCE: 44

Asp Ile Val Met Thr Gln Thr Pro Leu Ser Leu Pro Val Thr Pro Gly
  1               5                  10                  15

Glu Pro Ala Ser Ile Ser Cys Lys Ser Ser Gln Ser Leu Leu Ala Ser
             20                  25                  30

Gly Asn Gln Asn Asn Tyr Leu Ala Trp His Leu Gln Lys Pro Gly Gln
         35                  40                  45

Ser Pro Gln Met Leu Ile Ile Trp Ala Ser Thr Arg Val Ser Gly Val
     50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Gln
                 85                  90                  95

Ser Tyr Ser Ala Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic amino acid sequence of H3-light

```
<400> SEQUENCE: 45

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Ala Ser
             20                  25                  30

Gly Asn Gln Asn Asn Tyr Leu Ala Trp Tyr Gln Gln Lys Pro Gly Gln
         35                  40                  45

Pro Pro Lys Leu Leu Ile Ile Trp Ala Ser Thr Arg Val Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
             85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 46
<211> LENGTH: 219
<212> TYPE: PRT
<213> ORGANISM: Artificial Sequence
<220> FEATURE:
<223> OTHER INFORMATION: Synthetic amino acid sequence of H4-light

<400> SEQUENCE: 46

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
             85                  90                  95

Ser Tyr Ser Ala Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
```

```
              130                 135                 140
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
    210                 215

<210> SEQ ID NO 47
<211> LENGTH: 1350
<212> TYPE: DNA
<213> ORGANISM: Artificial Sequence
<220> FEATURE:
<223> OTHER INFORMATION: Synthetic nucleotide sequence of H1-heavy

<400> SEQUENCE: 47
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg ggctggagtg gttgggcttt attagaaaca agctaacgg ttacaccaca      180 gaatacagtg cgtctgtgaa aggcagattc accatctcaa gagataattc aaagaactca    240
ctgtatctgc aaatgaacag cctgaaaacc gaggacacgg ccgtgtatta ctgtgctaga    300
gataactggt ttgcttactg gggtcaagga accctggtca ccgtctcctc ggctagcacc    360
aagggcccat cggtcttccc cctggcaccc tcctccaaga gcacctctgg ggcacagcg     420 gccctgggct gcctggtcaa ggactacttc cccgaaccgg tgacggtgtc gtggaactca    480
ggcgccctga ccagcggcgt gcacaccttc cggctgtcc tacagtcctc aggactctac     540
tccctcagca gcgtggtgac cgtgccctcc agcagcttgg gcacccagac ctacatctgc    600
aacgtgaatc acaagcccag caacaccaag gtggacaaga agttgagcc caaatcttgt    660 gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga tgaccaag     1080 aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca gagcaggtg gcagcagggg   1260 aacgtcttct catgctccgt gatgcatgag gctctgcaca accactacac gcagaagagc   1320 ctctcccctgt ctccgggtaa atgactcgag                                    1350

<210> SEQ ID NO 48
<211> LENGTH: 1350
<212> TYPE: DNA
<213> ORGANISM: Artificial Sequence
<220> FEATURE:
```

<223> OTHER INFORMATION: Synthetic nucleotide sequence of H3-heavy

<400> SEQUENCE: 48

```
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg ggctggagtg gttgggcttt attagaaaca aagctaacgg ttacaccaca     180
gaatacagtg cgtctgtgaa aggcagattc accatctcaa gagataattc aaagaactca     240
ctgtatctgc aaatgaacag cctgcgtgct gaggacacgg ccgtgtatta ctgtgctaga     300
gataactggt ttgcttactg gggtcaagga accctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagccc caaatcttgt     660
gacaaaactc acacatgccc accgtgccca gcacctgaac tcctgggggg accgtcagtc     720
ttcctcttcc cccaaaaccc aaggacaccc tcatgatctc ccggaccccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga tgaccaag     1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca gagcaggtg gcagcagggg    1260
aacgtcttct catgctccgt gatgcatgag gctctgcaca accactacac gcagaagagc    1320
ctctccctgt ctccgggtaa atgactcgag                                     1350
```

<210> SEQ ID NO 49
<211> LENGTH: 1350
<212> TYPE: DNA
<213> ORGANISM: Artificial Sequence
<220> FEATURE:
<223> OTHER INFORMATION: Synthetic nucleotide sequence of H4-heavy

<400> SEQUENCE: 49

```
gaggttcagc tggtggagtc tggcggtggc ctggtgcagc cagggggctc actccgtttg      60
tcctgtgcag cttctggctt caccttcact gattactaca tgagctgggt gcgtcaggcc     120
ccgggtaagg gcctggaatg gttgggtttt attagaaaca aagctaatgg ttacacaaca     180
gagtacagtg catctgtgaa gggtcgtttc actataagca gagataattc aaaaacaca     240
ctgtacctgc agatgaacag cctgcgtgct gaggacactg ccgtctatta ttgtgctaga     300
gataactggt ttgcttactg gggccaaggg actctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
```

```
aacgtgaatc acaagcccag caacaccaag gtggacaaga aagttgagcc caaatcttgt      660
gacaaaactc acacatgccc accgtgccca gcacctgaac tcctgggggg accgtcagtc      720
ttcctcttcc ccccaaaacc caaggacacc ctcatgatct cccggacccc tgaggtcaca      780
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaccatctc caaagccaaa     1020
gggcagcccc gagaaccaca ggtgtacacc ctgcccccat cccgggagga tgaccaag     1080
aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
gacggctcct tcttcctcta cagcaagctc accgtggaca agagcaggtg gcagcagggg     1260
aacgtcttct catgctccgt gatgcatgag gctctgcaca accactacac gcagaagagc     1320
ctctccctgt ctccgggtaa atgactcgag                                       1350

<210> SEQ ID NO 50
<211> LENGTH: 669
<212> TYPE: DNA
<213> ORGANISM: Artificial Sequence
<220> FEATURE:
<223> OTHER INFORMATION: Synthetic nucleotide sequence of H1-light

<400> SEQUENCE: 50
gacatcgtga tgacccagtc tccagactcc ctggctgtgt ctctgggcga gagggccacc       60
atcaactgca gtccagcca gagtctttta gctagcggca accaaaataa ctacttagct      120
tggcaccagc agaaaccagg acagcctcct aagatgctca tttatttggc atctacccgg      180
gtatccgggg tccctgaccg attcagtggc agcgggtctg ggacagattt cactctcacc      240
atcagcagcc tgcaggctga agatgtggca gtttattact gtcagcaatc ctatagtgct      300
cctctcacgt tcggaggcgg taccaaggtg gagatcaaac gtacggtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga aacacaaagt ctacgcctgc      600
gaagtcaccc atcagggcct gagctcgccc gtcacaaaga gcttcaacag gggagagtgt      660
tgactcgag                                                              669

<210> SEQ ID NO 51
<211> LENGTH: 669
<212> TYPE: DNA
<213> ORGANISM: Artificial Sequence
<220> FEATURE:
<223> OTHER INFORMATION: Synthetic nucleotide sequence of H2-light

<400> SEQUENCE: 51
gatattgtga tgacccagac tccactctcc ctgcccgtca cccctggaga gccggcctcc       60
atctcctgca gtccagtca gagtctttta gctagtggca accaaaataa ctacttggcc      120
tggcacctgc agaagccagg gcagtctcca cagatgctga tcatttgggc atccactagg      180
gtatctggag tcccagacag gttcagtggc agtgggtcag gcactgattt cacactgaaa      240
```

```
atcagcaggg tggaggctga ggatgttgga gtttattact gccagcagtc ctacagcgct    300
ccgctcacgt tcggacaggg taccaagctg gagctcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc    600 gaagtcaccc atcagggcct gagctcgccc gtcacaaaga gcttcaacag gggagagtgt    660
tgactcgag                                                            669
```

<210> SEQ ID NO 52
<211> LENGTH: 669
<212> TYPE: DNA
<213> ORGANISM: Artificial Sequence
<220> FEATURE:
<223> OTHER INFORMATION: Synthetic nucleotide sequence of H3-light

<400> SEQUENCE: 52

```
gacatcgtga tgacccagtc tccagactcc ctggctgtgt ctctgggcga gagggccacc     60
atcaactgca gtccagcca gagtcttta gctagcggca accaaaataa ctacttagct    120
tggtaccagc agaaaccagg acagcctcct aagctgctca ttatttgggc atctacccgg    180
gtatccgggg tccctgaccg attcagtggc agcgggtctg gacagattt cactctcacc    240 atcagcagcc tgcaggctga agatgtggca gtttattact gtcagcaatc ctatagtgct    300
cctctcacgt tcggaggcgg taccaaggtg gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc    600 gaagtcaccc atcagggcct gagctcgccc gtcacaaaga gcttcaacag gggagagtgt    660
tgactcgag                                                            669
```

<210> SEQ ID NO 53
<211> LENGTH: 669
<212> TYPE: DNA
<213> ORGANISM: Artificial Sequence
<220> FEATURE:
<223> OTHER INFORMATION: Synthetic nucleotide sequence of H4-light

<400> SEQUENCE: 53

```
gatatccaga tgacccagtc cccgagctcc ctgtccgcct ctgtgggcga tagggtcacc     60
atcacctgca gtccagtca gagtctttta gctagtggca accaaaataa ctacttggcc    120
tggcaccaac agaaaccagg aaaagctccg aaaatgctga ttatttgggc atccactagg    180
gtatctggag tcccttctcg cttctctgga tccgggtctg gacgagattt cactctgacc    240
atcagcagtc tgcagccgga agacttcgca acttattact gtcagcagtc ctacagcgct    300
ccgctcacgt tcggacaggg taccaaggtg gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc    600
```

```
gaagtcaccc atcagggcct gagctcgccc gtcacaaaga gcttcaacag gggagagtgt    660
tgactcgag                                                             669
```

<210> SEQ ID NO 54
<211> LENGTH: 23
<212> TYPE: PRT
<213> ORGANISM: Artificial Sequence
<220> FEATURE:
<223> OTHER INFORMATION: Synthetic linker between VH and VL

<400> SEQUENCE: 54

Gly Leu Gly Gly Leu Gly Gly Gly Ser Gly Gly Gly Gly Ser Gly
1               5                   10                  15

Gly Ser Ser Gly Val Gly Ser
            20

<210> SEQ ID NO 55
<211> LENGTH: 1088
<212> TYPE: DNA
<213> ORGANISM: Artificial Sequence
<220> FEATURE:
<223> OTHER INFORMATION: Synthetic polynucleotide encoding scFv of
      huAbF46 antibody

<400> SEQUENCE: 55

```
gctagcgttt tagcagaagt tcaattggtt gaatctggtg gtggtttggt tcaaccaggt     60
ggttctttga gattgtcttg tgctgcttct ggttttactt tcaccgatta ttacatgtcc    120
tgggttagac aagctccagg taaaggtttg aatggttgg gtttcattag aaacaaggct    180
aacggttaca ctaccgaata ttctgcttct gttaaggta gattcaccat ttctagagac    240
aactctaaga caccttgta cttgcaaatg aactccttga gagctgaaga tactgctgtt    300
tattactgcg ctagagataa ttggtttgct tattggggtc aaggtacttt ggttactgtt    360
tcttctggcc tcgggggcct cggaggagga ggtagtggcg gaggaggctc cggtggatcc    420
agcggtgtgg gttccgatat tcaaatgacc caatctccat cttctttgtc tgcttcagtt    480
ggtgatagag ttaccattac ttgtaagtcc tcccaatctt tgttggcttc tggtaatcag    540
aacaattact ggcttggca tcaacaaaaa ccaggtaaag ctccaaagat gttgattatt    600
tgggcttcta ccagagtttc tggtgttcca tctagatttt ctggttctgg ttccggtact    660
gatttacttt tgaccatttc atccttgcaa ccagaagatt tcgctactta ctactgtcaa    720
caatcttact ctgctccatt gacttttggt caaggtacaa aggtcgaaat caagagagaa    780
ttcggtaagc ctatccctaa ccctctcctc ggtctcgatt ctacgggtgg tggtggatct    840
ggtggtggtg gttctggtgg tggtggttct caggaactga caactatatg cgagcaaatc    900
ccctcaccaa ctttagaatc gacgccgtac tctttgtcaa cgactactat tttggccaac    960
gggaaggcaa tgcaaggagt ttttgaatat acaaatcag taacgtttgt cagtaattgc   1020
ggttctcacc cctcaacaac tagcaaaggc agccccataa acacacagta tgttttttga   1080
gtttaaac                                                             1088
```

<210> SEQ ID NO 56
<211> LENGTH: 5597
<212> TYPE: DNA
<213> ORGANISM: Artificial Sequence
<220> FEATURE:
<223> OTHER INFORMATION: Synthetic expression vector including
      polynucleotide encoding scFv of huAbF46 antibody
<220> FEATURE:

```
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg tttttcaata ttttctgtta ttgctagcgt tttagcagaa gttcaattgg     600
ttgaatctgg tggtggtttg gttcaaccag gtggttcttt gagattgtct tgtgctgctt     660
ctggttttac tttcaccgat tattacatgt cctgggttag acaagctcca ggtaaaggtt     720
tggaatggtt gggtttcatt agaaacaagg ctaacggtta cactaccgaa tattctgctt     780
ctgttaaggg tagattcacc atttctagag acaactctaa gaacaccttg tacttgcaaa     840
tgaactcctt gagagctgaa gatactgctg tttattactg cgctagagat aattggtttg     900
cttattgggg tcaaggtact ttggttactg tttcttctgg cctcgggggc ctcggaggag     960
gaggtagtgg cggaggaggc tccgtggat ccagcggtgt gggttccgat attcaaatga    1020
cccaatctcc atcttctttg tctgcttcag ttggtgatag agttaccatt acttgtaagt    1080
cctcccaatc tttgttggct tctggtaatc agaacaatta cttggcttgg catcaacaaa    1140
```

```
aaccaggtaa agctccaaag atgttgatta tttgggcttc taccagagtt tctggtgttc    1200
catctagatt ttctggttct ggttccggta ctgattttac tttgaccatt tcatccttgc    1260
aaccagaaga tttcgctact tactactgtc aacaatctta ctctgctcca ttgacttttg    1320
gtcaaggtac aaaggtcgaa atcaagagag aattcggtaa gcctatccct aaccctctcc    1380
tcggtctcga ttctacgggt ggtggtggat ctggtggtgg tggttctggt ggtggtggtt    1440
ctcaggaact gacaactata tgcgagcaaa tccccctcacc aactttagaa tcgacgccgt    1500
actctttgtc aacgactact attttggcca acgggaaggc aatgcaagga gttttttgaat   1560 attacaaatc agtaacgttt gtcagtaatt gcggttctca cccctcaaca actagcaaag    1620
gcagccccat aaacacacag tatgttttt gagtttaaac ccgctgatct gataacaaca     1680
gtgtagatgt aacaaaatcg actttgttcc cactgtactt ttagctcgta caaaatacaa    1740 tatactttc atttctccgt aaacaacatg ttttcccatg taatatcctt ttctattttt     1800
cgttccgtta ccaactttac acatacttta tatagctatt cacttctata cactaaaaaa   1860
ctaagacaat tttaattttg ctgcctgcca tatttcaatt tgttataaat tcctataatt    1920
tatcctatta gtagctaaaa aaagatgaat gtgaatcgaa tcctaagaga attgggcaag    1980
tgcacaaaca atacttaaat aaatactact cagtaataac ctatttctta gcattttttga  2040 cgaaatttgc tattttgtta gagtctttta caccatttgt ctccacacct ccgcttacat    2100
caacaccaat aacgccattt aatctaagcg catcaccaac attttctggc gtcagtccac    2160
cagctaacat aaaatgtaag ctctcggggc tctcttgcct tccaacccag tcagaaatcg    2220
agttccaatc caaaagttca cctgtcccac ctgcttctga atcaaacaag ggaataaacg    2280
aatgaggttt ctgtgaagct gcactgagta gtatgttgca gtcttttgga aatacgagtc    2340
ttttaataac tggcaaaccg aggaactctt ggtattcttg ccacgactca tctccgtgca    2400
gttggacgat atcaatgccg taatcattga ccagagccaa aacatcctcc ttaggttgat    2460
tacgaaacac gccaaccaag tatttcggag tgcctgaact attttttata gcttttacaa    2520
gacttgaaat tttccttgca ataaccgggt caattgttct cttttctattg ggcacacata   2580 taatacccag caagtcagca tcggaatcta gagcacattc tgcggcctct gtgctctgca    2640
agccgcaaac tttcaccaat ggaccagaac tacctgtgaa attaataaca gacatactcc    2700
aagctgcctt tgtgtgctta atcacgtata ctcacgtgct caatagtcac caatgccctc    2760
cctcttggcc ctctccttttt cttttttcga ccgaatttct tgaagacgaa agggcctcgt    2820
gatacgccta ttttttatagg ttaatgtcat gataataatg gtttcttagg acggatcgct    2880
tgcctgtaac ttacacgcgc ctcgtatctt ttaatgatgg aataatttgg gaatttactc    2940
tgtgtttatt tattttatg ttttgtattt ggatttttaga aagtaaataa agaaggtaga    3000
agagttacgg aatgaagaaa aaaaataaa caaaggttta aaaaatttca acaaaaagcg    3060
tactttacat atatatttat tagacaagaa aagcagatta aatagatata cattcgatta    3120
acgataagta aaatgtaaaa tcacaggatt ttcgtgtgtg gtcttctaca cagacaagat    3180
gaaacaattc ggcattaata cctgagagca ggaagagcaa gataaaaggt agtatttgtt    3240
ggcgatcccc ctagagtctt ttacatcttc ggaaaacaaa aactatttt tctttaattt     3300 cttttttttac tttctatttt taatttatat atttatatta aaaaatttaa attataatta   3360
tttttatagc acgtgatgaa aaggaccag gtggcacttt tcggggaaat gtgcgcggaa    3420
cccctatttg tttattttc taaatacatt caaatatgta tccgctcatg agacaataac    3480
```

```
cctgataaat gcttcaataa tattgaaaaa ggaagagtat gagtattcaa catttccgtg    3540
tcgcccttat tcccttttt gcggcatttt gccttcctgt ttttgctcac ccagaaacgc    3600
tggtgaaagt aaaagatgct gaagatcagt tgggtgcacg agtgggttac atcgaactgg    3660
atctcaacag cggtaagatc cttgagagtt ttcgccccga agaacgtttt ccaatgatga    3720 gcactttta agttctgcta tgtggcgcgg tattatcccg tgttgacgcc gggcaagagc    3780
aactcggtcg ccgcatacac tattctcaga atgacttggt tgagtactca ccagtcacag    3840
aaaagcatct tacggatggc atgacagtaa gagaattatg cagtgctgcc ataaccatga    3900
gtgataacac tgcggccaac ttacttctga acgatcgg aggaccgaag gagctaaccg     3960
cttttttgca caacatgggg gatcatgtaa ctcgccttga tcgttgggaa ccggagctga    4020
atgaagccat accaaacgac gagcgtgaca ccacgatgcc tgtagcaatg gcaacaacgt    4080
tgcgcaaact attaactggc gaactactta ctctagcttc ccggcaacaa ttaatagact    4140
ggatggaggc ggataaagtt gcaggaccac ttctgcgctc ggcccttccg gctggctggt    4200
ttattgctga taaatctgga gccggtgagc gtgggtctcg cggtatcatt gcagcactgg    4260
ggccagatgg taagccctcc cgtatcgtag ttatctacac gacgggcagt caggcaacta    4320
tggatgaacg aaatagacag atcgctgaga taggtgcctc actgattaag cattggtaac    4380
tgtcagacca gtttactca tatatacttt agattgattt aaaacttcat ttttaattta    4440
aaaggatcta ggtgaagatc ctttttgata atctcatgac caaaatccct aacgtgagt    4500 tttcgttcca ctgagcgtca gaccccgtag aaaagatcaa aggatcttct tgagatcctt    4560 ttttttctgcg cgtaatctgc tgcttgcaaa caaaaaaacc accgctacca gcggtggttt    4620
gtttgccgga tcaagagcta ccaactcttt ttccgaaggt aactggcttc agcagagcgc    4680
agataccaaa tactgtcctt ctagtgtagc cgtagttagg ccaccacttc aagaactctg    4740
tagcaccgcc tacatacctc gctctgctaa tcctgttacc agtggctgct gccagtggcg    4800
ataagtcgtg tcttaccggg ttggactcaa gacgatagtt accggataag gcgcagcggt    4860
cgggctgaac ggggggttcg tgcacacagc ccagcttgga gcgaacgacc tacaccgaac    4920
tgagatacct acagcgtgag cattgagaaa gcgccacgct tcccgaaggg agaaaggcgg    4980
acaggtatcc ggtaagcggc agggtcggaa caggagagcg cacgagggag cttccagggg    5040
ggaacgcctg gtatctttat agtcctgtcg ggtttcgcca cctctgactt gagcgtcgat    5100
ttttgtgatg ctcgtcaggg gggcgagcc tatggaaaaa cgccagcaac gcggcctttt    5160
tacggttcct ggccttttgc tggccttttg ctcacatgtt ctttcctgcg ttatcccctg    5220
attctgtgga taaccgtatt accgcctttg agtgagctga taccgctcgc cgcagccgaa    5280
cgaccgagcg cagcgagtca gtgagcgagg aagcggaaga gcgcccaata cgcaaaccgc    5340
ctctccccgc gcgttggccg attcattaat gcagctggca cgacaggttt cccgactgga    5400
aagcgggcag tgagcgcaac gcaattaatg tgagttacct cactcattag gcaccccagg    5460
ctttacactt tatgcttccg gctcctatgt tgtgtggaat tgtgagcgga taacaatttc    5520
acacaggaaa cagctatgac catgattacg ccaagctcgg aattaaccct cactaaaggg    5580
aacaaaagct ggctagt                                                  5597
```

<210> SEQ ID NO 57
<211> LENGTH: 13
<212> TYPE: PRT
<213> ORGANISM: Artificial Sequence
<220> FEATURE:
<223> OTHER INFORMATION: Synthetic U6-HC7 hinge

<400> SEQUENCE: 57

Glu Pro Lys Ser Cys Asp Cys His Cys Pro Pro Cys Pro
 1               5                   10

<210> SEQ ID NO 58
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-1 clone

<400> SEQUENCE: 58

```
gaattcacta gtgattaatt cgccgccacc atggattcac aggcccaggt cctcatgttg    60
ctgctgctat cggtatctgg tacctgtgga gatatccaga tgacccagtc cccgagctcc   120
ctgtccgcct ctgtgggcga tagggtcacc atcacctgca agtccagtca gagtctttta   180
gctagtggca accaaaataa ctacttggcc tggcaccaac agaaaccagg aaaagctccg   240
aaaatgctga ttatttgggc atccactagg gtatctggag tcccttctcg cttctctgga   300
tccgggtctg ggacggattt cactctgacc atcagcagtc tgcagccgga agacttcgca   360
acttattact gtcagcagtc ctacagccgc ccgtacacgt tcggacaggg taccaaggtg   420
gagatcaaac gtacg                                                    435
```

<210> SEQ ID NO 59
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-2 clone

<400> SEQUENCE: 59

```
gaattcacta gtgattaatt cgccgccacc atggattcac aggcccaggt cctcatgttg    60
ctgctgctat cggtatctgg tacctgtgga gatatccaga tgacccagtc cccgagctcc   120
ctgtccgcct ctgtgggcga tagggtcacc atcacctgca agtccagtca gagtctttta   180
gctagtggca accaaaataa ctacttggcc tggcaccaac agaaaccagg aaaagctccg   240
aaaatgctga ttatttgggc atccactagg gtatctggag tcccttctcg cttctctgga   300
tccgggtctg ggacggattt cactctgacc atcagcagtc tgcagccgga agacttcgca   360
acttattact gtgggcagtc ctacagccgt ccgctcacgt tcggacaggg taccaaggtg   420
gagatcaaac gtacg                                                    435
```

<210> SEQ ID NO 60
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-3 clone

<400> SEQUENCE: 60

```
gaattcacta gtgattaatt cgccgccacc atggattcac aggcccaggt cctcatgttg    60
ctgctgctat cggtatctgg tacctgtgga gatatccaga tgacccagtc cccgagctcc   120
ctgtccgcct ctgtgggcga tagggtcacc atcacctgca agtccagtca gagtctttta   180
gctagtggca accaaaataa ctacttggcc tggcaccaac agaaaccagg aaaagctccg   240
```

```
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtgcacagtc ctacagccat ccgttctctt tcggacaggg taccaaggtg    420
gagatcaaac gtacg                                                     435
```

<210> SEQ ID NO 61
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-5 clone

<400> SEQUENCE: 61

```
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca gtccagtca gagtctttta    180 gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtcagcagtc ctacagccgc ccgtttacgt tcggacaggg taccaaggtg    420
gagatcaaac gtacg                                                     435
```

<210> SEQ ID NO 62
<211> LENGTH: 462
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, U6-HC7 hinge and constant region of human IgG1

<400> SEQUENCE: 62

```
Met Glu Trp Ser Trp Val Phe Leu Val Thr Leu Leu Asn Gly Ile Gln
  1               5                  10                  15

Cys Glu Val Gln Leu Val Glu Ser Gly Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175
```

```
Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
        210                 215                 220

Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
            355                 360                 365

Ser Arg Glu Glu Met Thr Lys Asn Gln Val Ser Leu Thr Cys Leu Val
        370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
        450                 455                 460

<210> SEQ ID NO 63
<211> LENGTH: 1410
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, U6-HC7
      hinge and constant region of human IgG1

<400> SEQUENCE: 63
gaattcgccg ccaccatgga atggagctgg gttttctcg taacactttt aaatggtatc      60
cagtgtgagg ttcagctggt ggagtctggc ggtggcctgg tgcagccagg gggctcactc     120
cgtttgtcct gtgcagcttc tggcttcacc ttcactgatt actacatgag ctgggtgcgt     180
caggccccgg gtaagggcct ggaatggttg gttttattaa gaaacaaagc taatggttac     240
acaacagagt acagtgcatc tgtgaagggt cgtttcacta taagcagaga taattccaaa     300
aacacactgt acctgcagat gaacagcctg cgtgctgagg acactgccgt ctattattgt     360
gctagagata actggtttgc ttactggggc caagggactc tggtcaccgt ctcctcggct     420
```

```
agcaccaagg gcccatcggt cttccccctg gcaccctcct ccaagagcac ctctgggggc      480
acagcggccc tgggctgcct ggtcaaggac tacttccccg aaccggtgac ggtgtcgtgg      540
aactcaggcg ccctgaccag cggcgtgcac accttcccgg ctgtcctaca gtcctcagga      600
ctctactccc tcagcagcgt ggtgaccgtg ccctccagca gcttgggcac ccagacctac      660
atctgcaacg tgaatcacaa gcccagcaac accaaggtgg acaagaaagt tgagcccaaa      720
agctgcgatt gccactgtcc tccatgtcca gcacctgaac tcctgggggg accgtcagtc      780
ttcctcttcc ccccaaaacc caaggacacc ctcatgatct cccggacccc tgaggtcaca      840
tgcgtggtgg tggacgtgag ccacgaagac cctgaggtca agttcaactg gtacgtggac      900
ggcgtggagg tgcataatgc caagacaaag ccgcgggagg agcagtacaa cagcacgtac      960
cgtgtggtca gcgtcctcac cgtcctgcac caggactggc tgaatggcaa ggagtacaag     1020
tgcaaggtct ccaacaaagc cctcccagcc cccatcgaga aaaccatctc caaagccaaa     1080
gggcagcccc gagaaccaca ggtgtacacc ctgcccccat cccgggagga gatgaccaag     1140
aaccaggtca gcctgacctg cctggtcaaa ggcttctatc ccagcgacat cgccgtggag     1200
tgggagagca atgggcagcc ggagaacaac tacaagacca cgcctcccgt gctggactcc     1260
gacggctcct tcttcctcta cagcaagctc accgtggaca agagcaggtg gcagcagggg     1320
aacgtcttct catgctccgt gatgcatgag gctctgcaca accactacac gcagaagagc     1380
ctctccctgt ctccgggtaa atgactcgag                                      1410
```

<210> SEQ ID NO 64
<211> LENGTH: 461
<212> TYPE: PRT
<213> ORGANISM: Artificial Sequence
<220> FEATURE:
<223> OTHER INFORMATION: Synthetic polypeptide consisting of heavy chain
     of huAbF46-H4-A1, human IgG2 hinge and constant region of human
     IgG1

<400> SEQUENCE: 64

```
Met Glu Trp Ser Trp Val Phe Leu Val Thr Leu Leu Asn Gly Ile Gln
  1               5                  10                  15

Cys Glu Val Gln Leu Val Glu Ser Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175
```

Ser Gly Ala Leu Thr Ser Gly Val His Thr Phe Pro Ala Val Leu Gln
            180                 185                 190

Ser Ser Gly Leu Tyr Ser Leu Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 65
<211> LENGTH: 1407
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2
      hinge and constant region of human IgG1

<400> SEQUENCE: 65
gaattcgccg ccaccatgga atggagctgg gttttttctcg taacactttt aaatggtatc    60
cagtgtgagg ttcagctggt ggagtctggc ggtggcctgg tgcagccagg gggctcactc   120
cgtttgtcct gtgcagcttc tggcttcacc ttcactgatt actacatgag ctgggtgcgt   180
caggccccgg gtaagggcct ggaatggttg ggttttatta gaaacaaagc taatggttac   240
acaacagagt acagtgcatc tgtgaagggt cgtttcacta taagcagaga taattccaaa   300
aacacactgt acctgcagat gaacagcctg cgtgctgagg acactgccgt ctattattgt   360

```
gctagagata actggtttgc ttactggggc aagggactc tggtcaccgt ctcctcggct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagaggaag    720
tgctgtgtgg agtgcccccc ctgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaagggg   1080
cagccccgag aaccacaggt gtacaccctg cccccatccc gggaggagat gaccaagaac   1140
caggtcagcc tgacctgcct ggtcaaaggc ttctatccca gcgacatcgc cgtggagtgg   1200
gagagcaatg ggcagccgga gaacaactac aagaccacgc tcccgtgct ggactccgac   1260 ggctccttct tcctctacag caagctcacc gtggacaaga gcaggtggca gcagggaac    1320 gtcttctcat gctccgtgat gcatgaggct ctgcacaacc actacacgca gaagagcctc   1380
tccctgtctc cgggtaaatg actcgag                                         1407
```

<210> SEQ ID NO 66
<211> LENGTH: 460
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, human IgG2 hinge and constant region of human
      IgG2

<400> SEQUENCE: 66

```
Met Glu Trp Ser Trp Val Phe Leu Val Thr Leu Leu Asn Gly Ile Gln
 1               5                  10                  15

Cys Glu Val Gln Leu Val Glu Ser Gly Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
```

```
              165                 170                 175
Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 67
<211> LENGTH: 1404
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2
      hinge and constant region of human IgG2

<400> SEQUENCE: 67
gaattcgccg ccaccatgga atggagctgg gttttctcg taacactttt aaatggtatc      60
cagtgtgagg ttcagctggt ggagtctggc ggtggcctgg tgcagccagg ggctcactc    120 cgtttgtcct gtgcagcttc tggcttcacc ttcactgatt actacatgag ctgggtgcgt   180
caggccccgg gtaagggcct ggaatggttg ggttttatta gaaacaaagc taatggttac   240
acaacagagt acagtgcatc tgtgaagggg cgtttcacta agcagaga taattccaaa     300 aacacactgt acctgcagat gaacagcctg cgtgctgagg acactgccgt ctattattgt   360
```

```
gctagagata actggtttgc ttactggggc caagggactc tggtcaccgt ctcctcggct    420
agcaccaagg gcccatcggt cttcccctg gcgccctgct ccaggagcac ctccgagagc     480
acagcggccc tgggctgcct ggtcaaggac tacttcccg aaccggtgac ggtgtcgtgg    540
aactcaggcg ctctgaccag cggcgtgcac accttcccag ctgtcctaca gtcctcagga    600
ctctactccc tcagcagcgt ggtgaccgtg ccctccagca acttcggcac ccagacctac    660
acctgcaacg tagatcacaa gcccagcaac accaaggtgg acaagacagt tgagcgcaaa    720
tgttgtgtcg agtgcccacc gtgcccagca ccacctgtgg caggaccgtc agtcttcctc    780 ttcccccca aacccaagga caccctcatg atctcccgga ccctgaggt cacgtgcgtg      840 gtggtggacg tgagccacga agaccccgag gtccagttca actggtacgt ggacggcgtg    900
gaggtgcata atgccaagac aaagccacgg gaggagcagt tcaacagcac gttccgtgtg    960
gtcagcgtcc tcaccgttgt gcaccaggac tggctgaacg gcaaggagta caagtgcaag   1020
gtctccaaca aaggcctccc agcccccatc gagaaaacca tctccaaaac caaagggcag   1080
ccccgagaac cacaggtgta caccctgccc ccatcccggg aggagatgac caagaaccag   1140
gtcagcctga cctgcctggt caaaggcttc taccccagcg acatcgccgt ggagtgggag   1200
agcaatgggc agccggagaa caactacaag accacgcctc ccatgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaatgact cgag                                         1404

<210> SEQ ID NO 68
<211> LENGTH: 240
<212> TYPE: PRT
<213> ORGANISM: Artificial Sequence
<220> FEATURE:
<223> OTHER INFORMATION: Synthetic polypeptide consisting of light chain
      of huAbF46-H4-A1(H36Y) and human kappa constant region

<400> SEQUENCE: 68

Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp Tyr Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
```

```
                165                 170                 175
Asp Asn Ala Leu Gln Ser Gly Asn Ser Gln Glu Ser Val Thr Glu Gln
                    180                 185                 190

Asp Ser Lys Asp Ser Thr Tyr Ser Leu Ser Ser Thr Leu Thr Leu Ser
                195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 69
<211> LENGTH: 758
<212> TYPE: DNA
<213> ORGANISM: Artificial Sequence
<220> FEATURE:
<223> OTHER INFORMATION: Synthetic polynucleotide encoding polypeptide
      consisting of light chain of huAbF46-H4-A1(H36Y) and
      human kappa constant region

<400> SEQUENCE: 69
aattcactag tgattaattc gccgccacca tggattcaca ggcccaggtc ctcatgttgc     60
tgctgctatc ggtatctggt acctgtggag atatccagat gacccagtcc ccgagctccc    120
tgtccgcctc tgtgggcgat agggtcacca tcacctgcaa gtccagtcag agtcttttag    180
ctagtggcaa ccaaaataac tacttggcct ggtaccaaca gaaaccagga aaagctccga    240
aaatgctgat tatttgggca tccactaggg tatctggagt ccctgctcgc ttctctggat    300
ccgggtctgg gacggatttc actctgacca tcagcagtct gcagccggaa gacttcgcaa    360
cttattactg tcagcagtcc tacagccgcc cgtacacgtt cggacagggt accaaggtgg    420
agatcaaacg tacggtggct gcaccatctg tcttcatctt cccgccatct gatgagcagt    480
tgaaatctgg aactgcctct gttgtgtgcc tgctgaataa cttctatccc agagaggcca    540
aagtacagtg gaaggtggat aacgcccctc aatcgggtaa ctcccaggag agtgtcacag    600
agcaggacag caaggacagc acctacagcc tcagcagcac cctgacgctg agcaaagcag    660
actacgagaa acacaaagtc tacgcctgcg aagtcaccca tcagggcctg agctcgcccg    720
tcacaaagag cttcaacagg ggagagtgtt gactcgag                            758

<210> SEQ ID NO 70
<211> LENGTH: 240
<212> TYPE: PRT
<213> ORGANISM: Artificial Sequence
<220> FEATURE:
<223> OTHER INFORMATION: Synthetic polypeptide consisting of light chain
      of huAbF46-H4-A1 and human kappa constant region

<400> SEQUENCE: 70

Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
                20                  25                  30

Ala Ser Val Gly Asp Arg Val Thr Ile Thr Cys Lys Ser Ser Gln Ser
            35                  40                  45

Leu Leu Ala Ser Gly Asn Gln Asn Asn Tyr Leu Ala Trp His Gln Gln
        50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
```

```
                    85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 71
<211> LENGTH: 19
<212> TYPE: PRT
<213> ORGANISM: Artificial Sequence
<220> FEATURE:
<223> OTHER INFORMATION: Synthetic epitope in SEMA domain of c-Met

<400> SEQUENCE: 71

Phe Ser Pro Gln Ile Glu Glu Pro Ser Gln Cys Pro Asp Cys Val Val
  1               5                  10                  15

Ser Ala Leu

<210> SEQ ID NO 72
<211> LENGTH: 10
<212> TYPE: PRT
<213> ORGANISM: Artificial Sequence
<220> FEATURE:
<223> OTHER INFORMATION: Synthetic epitope in SEMA domain of c-Met

<400> SEQUENCE: 72

Pro Gln Ile Glu Glu Pro Ser Gln Cys Pro
  1               5                  10

<210> SEQ ID NO 73
<211> LENGTH: 5
<212> TYPE: PRT
<213> ORGANISM: Artificial Sequence
<220> FEATURE:
<223> OTHER INFORMATION: Synthetic epitope in SEMA domain of c-Met

<400> SEQUENCE: 73

Glu Glu Pro Ser Gln
  1               5

<210> SEQ ID NO 74
<211> LENGTH: 117
<212> TYPE: PRT
<213> ORGANISM: Artificial Sequence
<220> FEATURE:
<223> OTHER INFORMATION: Synthetic heavy chain variable region of anti-
      c-Met antibody (AbF46 or huAbF46-H1)
```

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
            85                  90                  95

Tyr Cys Ala Arg Asp Asn Trp Phe Ala Tyr Trp Gly Gln Gly Thr Leu
        100                 105                 110

Val Thr Val Ser Ser
            115

<210> SEQ ID NO 75
<211> LENGTH: 114
<212> TYPE: PRT
<213> ORGANISM: Artificial Sequence
<220> FEATURE:
<223> OTHER INFORMATION: Synthetic light chain variable region of anti-
      c-Met antibody (AbF46 or huAbF46-H1)

<400> SEQUENCE: 75

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Ser Tyr Ser Ala Pro Leu Thr Phe Gly Gly Gly Thr Lys Val Glu Ile
        100                 105                 110

Lys Arg

<210> SEQ ID NO 76
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      anti-c-Met antibody (AbF46 or huAbF46-H1)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)

<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 76

```
gaattcgccg ccaccatgga atggagctgg gttttctctg taacactttt aaatggtatc      60
cagtgtgagg tgaagctggt ggagtctgga ggaggcttgg tacagcctgg gggttctctg     120
agactctcct gtgcaacttc tgggttcacc ttcactgatt actacatgag ctgggtccgc     180
cagcctccag aaaggcact tgagtggttg gtttttatta aaacaaagc taatggttac      240
acaacagagt acagtgcatc tgtgaagggt cggttcacca tctccagaga taattcccaa     300
agcatcctct atcttcaaat ggacaccctg agagctgagg acagtgccac ttattactgt     360
gcaagagata ctggtttgc ttactggggc caagggactc tggtcactgt ctctgcagct     420
agcaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gaccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga ctcgag                              1416
```

<210> SEQ ID NO 77
<211> LENGTH: 759
<212> TYPE: DNA
<213> ORGANISM: Artificial Sequence
<220> FEATURE:
<223> OTHER INFORMATION: Synthetic nucleotide sequence of light chain of anti-c-Met antibody (AbF46 or huAbF46-H1)
<220> FEATURE:
<221> NAME/KEY: misc_difference
<222> LOCATION: (1)..(6)

<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77

```
gaattcacta gtgattaatt cgccgccacc atgattcac aggcccaggt cctcatgttg      60
ctgctgctat cggtatctgg tacctgtgga gacattttga tgacccagtc tccatcctcc    120
ctgactgtgt cagcaggaga aaggtcact atgagctgca agtccagtca gagtctttta    180
gctagtggca accaaaataa ctacttggcc tggcaccagc agaaaccagg acgatctcct    240
aaaatgctga taattgggc atccactagg gtatctggag tccctgatcg cttcataggc    300
agtggatctg ggacggattt cactctgacc atcaacagtg tgcaggctga agatctggct    360
gtttattact gtcagcagtc ctacagcgct ccgctcacgt tcggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga aacacaaagt ctacgcctgc gaagtcaccc atcagggcct gagctcgccc    720
gtcacaaaga gcttcaacag gggagagtgt tgactcgag                          759
```

<210> SEQ ID NO 78
<211> LENGTH: 4170
<212> TYPE: DNA
<213> ORGANISM: Artificial Sequence
<220> FEATURE:
<223> OTHER INFORMATION: Synthetic polynucleotide encoding c-Met protein

<400> SEQUENCE: 78

```
atgaaggccc ccgctgtgct tgcacctggc atcctcgtgc tcctgtttac cttggtgcag    60
aggagcaatg gggagtgtaa agaggcacta gcaaagtccg agatgaatgt gaatatgaag    120
tatcagcttc ccaacttcac cgcggaaaca cccatccaga atgtcattct acatgagcat    180
cacattttcc ttggtgccac taactacatt tatgttttaa atgaggaaga ccttcagaag    240
gttgctgagt acaagactgg gcctgtgctg gaacacccag attgtttccc atgtcaggac    300
tgcagcagca agccaatttt atcaggaggt gtttggaaag ataacatcaa catggctcta    360
gttgtcgaca cctactatga tgatcaactc attagctgtg gcagcgtcaa cagagggacc    420
tgccagcgac atgtctttcc ccacaatcat actgctgaca tacagtcgga ggttcactgc    480
```

```
atattctccc cacagataga agagcccagc cagtgtcctg actgtgtggt gagcgccctg      540
ggagccaaag tcctttcatc tgtaaaggac cggttcatca acttctttgt aggcaatacc      600
ataaattctt cttatttccc agatcatcca ttgcattcga tatcagtgag aaggctaaag      660
gaaacgaaag atggttttat gttttgacg gaccagtcct acattgatgt tttacctgag       720
ttcagagatt cttaccccat taagtatgtc catgcctttg aaagcaacaa ttttatttac      780
ttcttgacgg tccaaaggga aactctagat gctcagactt ttcacacaag aataatcagg      840
ttctgttcca taaactctgg attgcattcc tacatggaaa tgcctctgga gtgtattctc      900
acagaaaaga gaaaaagag atccacaaag aaggaagtgt taatatact tcaggctgcg       960 tatgtcagca agcctggggc ccagcttgct agacaaatag gagccagcct gaatgatgac     1020
attcttttcg gggtgttcgc acaaagcaag ccagattctg ccgaaccaat ggatcgatct     1080
gccatgtgtg cattccctat caaatatgtc aacgacttct caacaagat cgtcaacaaa     1140 aacaatgtga gatgtctcca gcattttac ggacccaatc atgagcactg ctttaatagg      1200
acacttctga gaaattcatc aggctgtgaa gcgcgccgtg atgaatatcg aacagagttt     1260
accacagctt tgcagcgcgt tgacttattc atgggtcaat cagcgaagt cctcttaaca     1320 tctatatcca ccttcattaa aggagacctc accatagcta atcttgggac atcagagggt     1380
cgcttcatgc aggttgtggt ttctcgatca ggaccatcaa cccctcatgt gaattttctc     1440
ctggactccc atccagtgtc tccagaagtg attgtggagc atacattaaa ccaaaatggc     1500
tacacactgg ttatcactgg gaagaagatc acgaagatcc cattgaatgg cttgggctgc     1560
agacatttcc agtcctgcag tcaatgcctc tctgccccac cctttgttca gtgtggctgg     1620
tgccacgaca aatgtgtgcg atcggaggaa tgcctgagcg ggacatggac tcaacagatc     1680
tgtctgcctg caatctacaa ggttttccca aatagtgcac cccttgaagg agggacaagg     1740
ctgaccatat gtggctggga ctttggattt cggaggaata taaatttga tttaaagaaa      1800 actagagttc tccttggaaa tgagagctgc accttgactt aagtgagag cacgatgaat     1860 acattgaaat gcacagttgg tcctgccatg aataagcatt tcaatatgtc cataattatt     1920
tcaaatggcc acgggacaac acaatacagt acattctcct atgtggatcc tgtaataaca     1980
agtatttcgc cgaaatacgg tcctatggct ggtggcactt tacttacttt aactggaaat     2040
tacctaaaca gtgggaattc tagacacatt tcaattggtg gaaaacatg tactttaaaa      2100 agtgtgtcaa acagtattct tgaatgttat accccagccc aaaccatttc aactgagttt     2160
gctgttaaat tgaaaattga cttagccaac cgagagacaa gcatcttcag ttaccgtgaa     2220
gatcccattg tctatgaaat tcatccaacc aaatctttta ttagtggtgg agcacaata      2280 acaggtgttg gaaaaacct gaattcagtt agtgtcccga aatggtcat aaatgtgcat      2340 gaagcaggaa ggaactttac agtggcatgt caacatcgct ctaattcaga gataatctgt     2400
tgtaccactc cttccctgca acagctgaat ctgcaactcc ccctgaaaac caaagccttt     2460
ttcatgttag atgggatcct ttccaaatac tttgatctca tttatgtaca taatcctgtg     2520
tttaagcctt ttgaaaagcc agtgatgatc tcaatgggca atgaaaatgt actggaaatt     2580
aagggaaatg atattgaccc tgaagcagtt aaaggtgaag tgttaaaagt tggaaataag     2640
agctgtgaga atatacactt acattctgaa gccgttttat gcacggtccc caatgacctg     2700
ctgaaattga acagcgagct aaatatagag tggaagcaag caatttcttc aaccgtcctt     2760
ggaaaagtaa tagttcaacc agatcagaat ttcacaggat tgattgctgg tgttgtctca     2820
```

```
atatcaacag cactgttatt actacttggg tttttcctgt ggctgaaaaa gagaaagcaa    2880
attaaagatc tgggcagtga attagttcgc tacgatgcaa gagtacacac tcctcatttg    2940
gataggcttg taagtgcccg aagtgtaagc ccaactacag aaatggtttc aaatgaatct    3000
gtagactacc gagctacttt tccagaagat cagtttccta attcatctca gaacggttca    3060
tgccgacaag tgcagtatcc tctgacagac atgtccccca tcctaactag tggggactct    3120
gatatatcca gtccattact gcaaaatact gtccacattg acctcagtgc tctaaatcca    3180
gagctggtcc aggcagtgca gcatgtagtg attgggccca gtagcctgat tgtgcatttc    3240
aatgaagtca taggaagagg gcattttggt tgtgtatatc atgggacttt gttggacaat    3300
gatggcaaga aaattcactg tgctgtgaaa tccttgaaca gaatcactga cataggagaa    3360
gtttcccaat ttctgaccga gggaatcatc atgaaagatt ttagtcatcc caatgtcctc    3420
tcgctcctgg gaatctgcct gcgaagtgaa gggtctccgc tggtggtcct accatacatg    3480
aaacatggag atcttcgaaa tttcattcga aatgagactc ataatccaac tgtaaaagat    3540
cttattggct ttggtcttca agtagccaaa ggcatgaaat atcttgcaag caaaaagttt    3600
gtccacagag acttggctgc aagaaactgt atgctggatg aaaaattcac agtcaaggtt    3660
gctgattttg gtcttgccag agacatgtat gataaagaat actatagtgt acacaacaaa    3720
acaggtgcaa agctgccagt gaagtggatg gctttggaaa gtctgcaaac tcaaaagttt    3780
accaccaagt cagatgtgtg gtcctttggc gtgctcctct gggagctgat gacaagagga    3840
gccccacctt atcctgacgt aaacaccttt gatataactg tttacttgtt gcaagggaga    3900
agactcctac aacccgaata ctgcccagac cccttatatg aagtaatgct aaaatgctgg    3960
caccctaaag ccgaaatgcg cccatccttt tctgaactgg tgtcccggat atcagcgatc    4020
ttctctactt tcattgggga gcactatgtc catgtgaacg ctacttatgt gaacgtaaaa    4080
tgtgtcgctc cgtatccttc tctgttgtca tcagaagata cgctgatga tgaggtggac    4140 acacgaccag cctccttctg ggagacatca                                     4170
```

<210> SEQ ID NO 79
<211> LENGTH: 444
<212> TYPE: PRT
<213> ORGANISM: Artificial Sequence
<220> FEATURE:
<223> OTHER INFORMATION: Synthetic SEMA domain of c-Met

<400> SEQUENCE: 79

```
Leu His Glu His His Ile Phe Leu Gly Ala Thr Asn Tyr Ile Tyr Val
  1               5                  10                  15

Leu Asn Glu Glu Asp Leu Gln Lys Val Ala Glu Tyr Lys Thr Gly Pro
             20                  25                  30

Val Leu Glu His Pro Asp Cys Phe Pro Cys Gln Asp Cys Ser Ser Lys
         35                  40                  45

Ala Asn Leu Ser Gly Gly Val Trp Lys Asp Asn Ile Asn Met Ala Leu
     50                  55                  60

Val Val Asp Thr Tyr Tyr Asp Asp Gln Leu Ile Ser Cys Gly Ser Val
 65                  70                  75                  80

Asn Arg Gly Thr Cys Gln Arg His Val Phe Pro His Asn His Thr Ala
                 85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125
```

```
Leu Ser Ser Val Lys Asp Arg Phe Ile Asn Phe Val Gly Asn Thr
    130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
                180                 185                 190

Tyr Val His Ala Phe Glu Ser Asn Asn Phe Ile Tyr Phe Leu Thr Val
            195                 200                 205

Gln Arg Glu Thr Leu Asp Ala Gln Thr Phe His Thr Arg Ile Ile Arg
    210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Lys Arg Ser Thr Lys Lys Glu
                245                 250                 255

Val Phe Asn Ile Leu Gln Ala Ala Tyr Val Ser Lys Pro Gly Ala Gln
                260                 265                 270

Leu Ala Arg Gln Ile Gly Ala Ser Leu Asn Asp Asp Ile Leu Phe Gly
            275                 280                 285

Val Phe Ala Gln Ser Lys Pro Asp Ser Ala Glu Pro Met Asp Arg Ser
    290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
    355                 360                 365

Gln Arg Val Asp Leu Phe Met Gly Gln Phe Ser Glu Val Leu Leu Thr
    370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Val Ser Arg Ser Gly Pro
                405                 410                 415

Ser Thr Pro His Val Asn Phe Leu Leu Asp Ser His Pro Val Ser Pro
                420                 425                 430

Glu Val Ile Val Glu His Thr Leu Asn Gln Asn Gly
            435                 440

<210> SEQ ID NO 80
<211> LENGTH: 451
<212> TYPE: PRT
<213> ORGANISM: Artificial Sequence
<220> FEATURE:
<223> OTHER INFORMATION: Synthetic PSI-IPT domain of c-Met

<400> SEQUENCE: 80

Tyr Thr Leu Val Ile Thr Gly Lys Lys Ile Thr Lys Ile Pro Leu Asn
1               5                   10                  15

Gly Leu Gly Cys Arg His Phe Gln Ser Cys Ser Gln Cys Leu Ser Ala
                20                  25                  30

Pro Pro Phe Val Gln Cys Gly Trp Cys His Asp Lys Cys Val Arg Ser
            35                  40                  45
```

```
Glu Glu Cys Leu Ser Gly Thr Trp Thr Gln Gln Ile Cys Leu Pro Ala
 50                  55                  60
Ile Tyr Lys Val Phe Pro Asn Ser Ala Pro Leu Glu Gly Gly Thr Arg
 65                  70                  75                  80
Leu Thr Ile Cys Gly Trp Asp Phe Gly Phe Arg Arg Asn Asn Lys Phe
                 85                  90                  95
Asp Leu Lys Lys Thr Arg Val Leu Leu Gly Asn Glu Ser Cys Thr Leu
             100                 105                 110
Thr Leu Ser Glu Ser Thr Met Asn Thr Leu Lys Cys Thr Val Gly Pro
         115                 120                 125
Ala Met Asn Lys His Phe Asn Met Ser Ile Ile Ile Ser Asn Gly His
         130                 135                 140
Gly Thr Thr Gln Tyr Ser Thr Phe Ser Tyr Val Asp Pro Val Ile Thr
145                 150                 155                 160
Ser Ile Ser Pro Lys Tyr Gly Pro Met Ala Gly Gly Thr Leu Leu Thr
                 165                 170                 175
Leu Thr Gly Asn Tyr Leu Asn Ser Gly Asn Ser Arg His Ile Ser Ile
             180                 185                 190
Gly Gly Lys Thr Cys Thr Leu Lys Ser Val Ser Asn Ser Ile Leu Glu
         195                 200                 205
Cys Tyr Thr Pro Ala Gln Thr Ile Ser Thr Glu Phe Ala Val Lys Leu
         210                 215                 220
Lys Ile Asp Leu Ala Asn Arg Glu Thr Ser Ile Phe Ser Tyr Arg Glu
225                 230                 235                 240
Asp Pro Ile Val Tyr Glu Ile His Pro Thr Lys Ser Phe Ile Ser Thr
                 245                 250                 255
Trp Trp Lys Glu Pro Leu Asn Ile Val Ser Phe Leu Phe Cys Phe Ala
             260                 265                 270
Ser Gly Gly Ser Thr Ile Thr Gly Val Gly Lys Asn Leu Asn Ser Val
         275                 280                 285
Ser Val Pro Arg Met Val Ile Asn Val His Glu Ala Gly Arg Asn Phe
         290                 295                 300
Thr Val Ala Cys Gln His Arg Ser Asn Ser Glu Ile Ile Cys Cys Thr
305                 310                 315                 320
Thr Pro Ser Leu Gln Gln Leu Asn Leu Gln Leu Pro Leu Lys Thr Lys
                 325                 330                 335
Ala Phe Phe Met Leu Asp Gly Ile Leu Ser Lys Tyr Phe Asp Leu Ile
             340                 345                 350
Tyr Val His Asn Pro Val Phe Lys Pro Phe Glu Lys Pro Val Met Ile
         355                 360                 365
Ser Met Gly Asn Glu Asn Val Leu Glu Ile Lys Gly Asn Asp Ile Asp
         370                 375                 380
Pro Glu Ala Val Lys Gly Glu Val Leu Lys Val Gly Asn Lys Ser Cys
385                 390                 395                 400
Glu Asn Ile His Leu His Ser Glu Ala Val Leu Cys Thr Val Pro Asn
                 405                 410                 415
Asp Leu Leu Lys Leu Asn Ser Glu Leu Asn Ile Glu Trp Lys Gln Ala
             420                 425                 430
Ile Ser Ser Thr Val Leu Gly Lys Val Ile Val Gln Pro Asp Gln Asn
         435                 440                 445
Phe Thr Gly
    450
```

<210> SEQ ID NO 81
<211> LENGTH: 313
<212> TYPE: PRT
<213> ORGANISM: Artificial Sequence
<220> FEATURE:
<223> OTHER INFORMATION: Synthetic TyrKc domain of c-Met

<400> SEQUENCE: 81

```
Val His Phe Asn Glu Val Ile Gly Arg Gly His Phe Gly Cys Val Tyr
 1               5                  10                  15

His Gly Thr Leu Leu Asp Asn Asp Gly Lys Lys Ile His Cys Ala Val
            20                  25                  30

Lys Ser Leu Asn Arg Ile Thr Asp Ile Gly Glu Val Ser Gln Phe Leu
        35                  40                  45

Thr Glu Gly Ile Ile Met Lys Asp Phe Ser His Pro Asn Val Leu Ser
    50                  55                  60

Leu Leu Gly Ile Cys Leu Arg Ser Glu Gly Ser Pro Leu Val Val Leu
65                  70                  75                  80

Pro Tyr Met Lys His Gly Asp Leu Arg Asn Phe Ile Arg Asn Glu Thr
                85                  90                  95

His Asn Pro Thr Val Lys Asp Leu Ile Gly Phe Gly Leu Gln Val Ala
            100                 105                 110

Lys Gly Met Lys Tyr Leu Ala Ser Lys Lys Phe Val His Arg Asp Leu
        115                 120                 125

Ala Ala Arg Asn Cys Met Leu Asp Glu Lys Phe Thr Val Lys Val Ala
    130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
        195                 200                 205

Asp Val Asn Thr Phe Asp Ile Thr Val Tyr Leu Leu Gln Gly Arg Arg
    210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270

Val His Val Asn Ala Thr Tyr Val Asn Val Lys Cys Val Ala Pro Tyr
        275                 280                 285

Pro Ser Leu Leu Ser Ser Glu Asp Asn Ala Asp Asp Glu Val Asp Thr
    290                 295                 300

Arg Pro Ala Ser Phe Trp Glu Thr Ser
305                 310
```

<210> SEQ ID NO 82
<211> LENGTH: 1332
<212> TYPE: DNA
<213> ORGANISM: Artificial Sequence
<220> FEATURE:
<223> OTHER INFORMATION: Synthetic polynucleotide encoding SEMA domain
      of c-Met

<400> SEQUENCE: 82

```
ctacatgagc atcacatttt ccttggtgcc actaactaca tttatgtttt aaatgaggaa      60
gaccttcaga aggttgctga gtacaagact gggcctgtgc tggaacaccc agattgtttc     120
ccatgtcagg actgcagcag caaagccaat ttatcaggag gtgtttggaa agataacatc     180
aacatggctc tagttgtcga cacctactat gatgatcaac tcattagctg tggcagcgtc     240
aacagaggga cctgccagcg acatgtcttt ccccacaatc atactgctga catacagtcg     300
gaggttcact gcatattctc cccacagata aagagccca gccagtgtcc tgactgtgtg      360
gtgagcgccc tgggagccaa agtcctttca tctgtaaagg accggttcat caacttcttt     420
gtaggcaata ccataaattc ttcttatttc ccagatcatc cattgcattc gatatcagtg     480
agaaggctaa aggaaacgaa agatggtttt atgtttttga cggaccagtc ctacattgat     540
gttttacctg agttcagaga ttcttacccc attaagtatg tccatgcctt tgaaagcaac     600
aattttattt acttcttgac ggtccaaagg gaaactctag atgctcagac ttttcacaca     660
agaataatca ggttctgttc cataaactct ggattgcatt cctacatgga aatgcctctg     720
gagtgtattc tcacagaaaa gagaaaaaag agatccacaa agaaggaagt gtttaatata     780
cttcaggctg cgtatgtcag caagcctggg gcccagcttg ctagacaaat aggagccagc     840
ctgaatgatg acattctttt cggggtgttc gcacaaagca agccagattc tgccgaacca     900
atggatcgat ctgccatgtg tgcattccct atcaaatatg tcaacgactt cttcaacaag     960
atcgtcaaca aaacaatgt gagatgtctc cagcattttt acggacccaa tcatgagcac    1020
tgctttaata ggacacttct gagaaattca tcaggctgtg aagcgcgccg tgatgaatat    1080
cgaacagagt ttaccacagc tttgcagcgc gttgactat tcatgggtca attcagcgaa    1140
gtcctcttaa catctatatc caccttcatt aaaggagacc tcaccatagc taatcttggg    1200
acatcagagg gtcgcttcat gcaggttgtg gtttctcgat caggaccatc aaccccctcat    1260
gtgaatttc tcctggactc ccatccagtg tctccagaag tgattgtgga gcatacatta    1320
aaccaaaatg gc                                                         1332
```

<210> SEQ ID NO 83
<211> LENGTH: 1299
<212> TYPE: DNA
<213> ORGANISM: Artificial Sequence
<220> FEATURE:
<223> OTHER INFORMATION: Synthetic polynucleotide encoding PSI-IPT
      domain of c-Met

<400> SEQUENCE: 83

```
tacacactgg ttatcactgg gaagaagatc acgaagatcc cattgaatgg cttgggctgc      60
agacatttcc agtcctgcag tcaatgcctc tctgccccac cctttgttca gtgtggctgg     120
tgccacgaca atgtgtgcg atcggaggaa tgcctgagcg ggacatggac tcaacagatc     180
tgtctgcctg caatctacaa ggttttccca aatagtgcac cccttgaagg agggacaagg     240
ctgaccatat gtggctggga ctttggattt cggaggaata taaatttga tttaaagaaa     300
actagagttc tccttggaaa tgagagctgc accttgactt aagtgagag cacgatgaat     360
acattgaaat gcagttgg tcctgccatg aataagcatt caatatgtc cataattatt        420
tcaaatggcc acgggacaac acaatacagt acattctcct atgtggatcc tgtaataaca    480
agtatttcgc cgaaatacgg tcctatggct ggtggcactt acttactttt aactggaaat    540
tacctaaaca gtgggaattc tagacacatt tcaattggtg gaaaaacatg tactttaaaa    600
```

| | | |
|---|---|---|
| agtgtgtcaa acagtattct tgaatgttat accccagccc aaaccatttc aactgagttt | 660 | |
| gctgttaaat tgaaaattga cttagccaac cgagagacaa gcatcttcag ttaccgtgaa | 720 | |
| gatcccattg tctatgaaat tcatccaacc aaatctttta ttagtggtgg gagcacaata | 780 | |
| acaggtgttg ggaaaaacct gaattcagtt agtgtcccga gaatggtcat aaatgtgcat | 840 | |
| gaagcaggaa ggaactttac agtggcatgt caacatcgct ctaattcaga gataatctgt | 900 | |
| tgtaccactc cttccctgca acagctgaat ctgcaactcc ccctgaaaac caaagccttt | 960 | |
| ttcatgttag atgggatcct ttccaaatac tttgatctca tttatgtaca taatcctgtg | 1020 | |
| tttaagcctt ttgaaaagcc agtgatgatc tcaatgggca atgaaaatgt actggaaatt | 1080 | |
| aagggaaatg atattgaccc tgaagcagtt aaaggtgaag tgttaaaagt tggaaataag | 1140 | |
| agctgtgaga atatacactt acattctgaa gccgttttat gcacggtccc caatgacctg | 1200 | |
| ctgaaattga acagcgagct aaatatagag tggaagcaag caatttcttc aaccgtcctt | 1260 | |
| ggaaaagtaa tagttcaacc agatcagaat ttcacagga | 1299 | |

<210> SEQ ID NO 84
<211> LENGTH: 939
<212> TYPE: DNA
<213> ORGANISM: Artificial Sequence
<220> FEATURE:
<223> OTHER INFORMATION: Synthetic polynucleotide encoding TyrKc domain of c-Met

<400> SEQUENCE: 84

| | | |
|---|---|---|
| gtgcatttca atgaagtcat aggaagaggg cattttggtt gtgtatatca tgggactttg | 60 | |
| ttggacaatg atggcaagaa aattcactgt gctgtgaaat ccttgaacag aatcactgac | 120 | |
| ataggagaag tttcccaatt tctgaccgag ggaatcatca tgaaagattt tagtcatccc | 180 | |
| aatgtcctct cgctcctggg aatctgcctg cgaagtgaag gtctccgct ggtggtccta | 240 | |
| ccatacatga acatggaga tcttcgaaat tcattcgaa atgagactca taatccaact | 300 | |
| gtaaaagatc ttattggctt tggtcttcaa gtagccaaag gcatgaaata tcttgcaagc | 360 | |
| aaaaagtttg tccacagaga cttggctgca agaaactgta tgctggatga aaaattcaca | 420 | |
| gtcaaggttg ctgattttgg tcttgccaga gacatgtatg ataaagaata ctatagtgta | 480 | |
| cacaacaaaa caggtgcaaa gctgccagtg aagtggatgg ctttggaaag tctgcaaact | 540 | |
| caaaagttta ccaccaagtc agatgtgtgg tcctttggcg tgctcctctg ggagctgatg | 600 | |
| acaagaggag ccccacctta tcctgacgta aacacctttg atataactgt ttacttgttg | 660 | |
| caagggagaa gactcctaca acccgaatac tgcccagacc ccttatatga agtaatgcta | 720 | |
| aaatgctggc accctaaagc cgaaatgcgc ccatcctttt ctgaactggt gtcccggata | 780 | |
| tcagcgatct tctctacttt cattgggag cactatgtcc atgtgaacgc tacttatgtg | 840 | |
| aacgtaaaat gtgtcgctcc gtatccttct ctgttgtcat cagaagataa cgctgatgat | 900 | |
| gaggtggaca cacgaccagc ctccttctgg gagacatca | 939 | |

<210> SEQ ID NO 85
<211> LENGTH: 13
<212> TYPE: PRT
<213> ORGANISM: Artificial Sequence
<220> FEATURE:
<223> OTHER INFORMATION: Synthetic heavy chain CDR3 of anti-c-Met antibody

<400> SEQUENCE: 85

Asp Asn Trp Phe Ala Tyr Trp Gly Gln Gly Thr Leu Val

<210> SEQ ID NO 86
<211> LENGTH: 10
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 86

Leu Thr Phe Gly Ala Gly Thr Lys Leu Glu
 1               5                  10

<210> SEQ ID NO 87
<211> LENGTH: 117
<212> TYPE: PRT
<213> ORGANISM: Artificial Sequence
<220> FEATURE:
<223> OTHER INFORMATION: Synthetic heavy chain variable region of
      monoclonal antibody AbF46

<400> SEQUENCE: 87

Glu Val Lys Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115

<210> SEQ ID NO 88
<211> LENGTH: 114
<212> TYPE: PRT
<213> ORGANISM: Artificial Sequence
<220> FEATURE:
<223> OTHER INFORMATION: Synthetic light chain variable region of anti-
      c-Met antibody

<400> SEQUENCE: 88

Asp Ile Leu Met Thr Gln Ser Pro Ser Ser Leu Thr Val Ser Ala Gly
 1               5                  10                  15

Glu Lys Val Thr Met Ser Cys Lys Ser Ser Gln Ser Leu Leu Ala Ser
            20                  25                  30

Gly Asn Gln Asn Asn Tyr Leu Ala Trp His Gln Gln Lys Pro Gly Arg
        35                  40                  45

Ser Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Gln
                85                  90                  95

Ser Tyr Ser Ala Pro Leu Thr Phe Gly Ala Gly Thr Lys Leu Glu Leu
                100                 105                 110

Lys Arg

<210> SEQ ID NO 89
<211> LENGTH: 17
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 89

Gln Gln Ser Tyr Ser Ala Pro Leu Thr Phe Gly Ala Gly Thr Lys Leu
 1               5                  10                  15

Glu

<210> SEQ ID NO 90
<211> LENGTH: 117
<212> TYPE: PRT
<213> ORGANISM: Artificial Sequence
<220> FEATURE:
<223> OTHER INFORMATION: Synthetic heavy chain variable region of AT-VH1

<400> SEQUENCE: 90

Glu Val Lys Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: Synthetic heavy chain variable region of AT-VH2

<400> SEQUENCE: 91

Glu Val Lys Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr

```
                65                  70                  75                  80
Leu Tyr Leu Gln Met Asn Ser Leu Arg Ala Glu Asp Thr Ala Thr Tyr
                    85                  90                  95

Tyr Cys Ala Arg Asp Asn Trp Phe Ala Tyr Trp Gly Gln Gly Thr Leu
                100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Synthetic heavy chain variable region of AT-VH3

<400> SEQUENCE: 92

Glu Val Gln Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
                 20                  25                  30

Tyr Met Ser Trp Val Arg Gln Pro Pro Gly Lys Gly Leu Glu Trp Leu
             35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Ser Thr
 65                  70                  75                  80

Leu Tyr Leu Gln Met Asn Ser Leu Arg Ala Glu Asp Thr Ala Thr Tyr
                 85                  90                  95

Tyr Cys Ala Arg Asp Asn Trp Phe Ala Tyr Trp Gly Gln Gly Thr Leu
                100                 105                 110

Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: Synthetic heavy chain variable region of AT-VH4

<400> SEQUENCE: 93

Glu Val Gln Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
                 20                  25                  30

Tyr Met Ser Trp Val Arg Gln Pro Pro Gly Lys Gly Leu Glu Trp Leu
             35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Thr Tyr
                 85                  90                  95

Tyr Cys Ala Arg Asp Asn Trp Phe Ala Tyr Trp Gly Gln Gly Thr Leu
                100                 105                 110

Val Thr Val Ser Ser
        115
```

<210> SEQ ID NO 94
<211> LENGTH: 117
<212> TYPE: PRT
<213> ORGANISM: Artificial Sequence
<220> FEATURE:
<223> OTHER INFORMATION: Synthetic heavy chain variable region of AT-VH5

<400> SEQUENCE: 94

```
Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115
```

<210> SEQ ID NO 95
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 95

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg
```

<210> SEQ ID NO 96
<211> LENGTH: 113
<212> TYPE: PRT
<213> ORGANISM: Artificial Sequence
<220> FEATURE:
<223> OTHER INFORMATION: Synthetic light chain variable region of AT-Vk1

<400> SEQUENCE: 96

```
Asp Ile Leu Met Thr Gln Ser Pro Ser Ser Leu Thr Ala Ser Val Gly
```

```
                1               5                   10                  15
Asp Arg Val Thr Met Thr Cys Lys Ser Ser Gln Ser Leu Leu Ala Ser
                    20                  25                  30

Gly Asn Gln Asn Asn Tyr Leu Ala Trp His Gln Gln Lys Pro Gly Lys
                35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
                100                 105                 110

Lys
```

<210> SEQ ID NO 97
<211> LENGTH: 113
<212> TYPE: PRT
<213> ORGANISM: Artificial Sequence
<220> FEATURE:
<223> OTHER INFORMATION: Synthetic light chain variable region of AT-Vk2

<400> SEQUENCE: 97

```
Asp Ile Leu Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
                35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
                100                 105                 110

Lys
```

<210> SEQ ID NO 98
<211> LENGTH: 113
<212> TYPE: PRT
<213> ORGANISM: Artificial Sequence
<220> FEATURE:
<223> OTHER INFORMATION: Synthetic light chain variable region of AT-Vk3

<400> SEQUENCE: 98

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
                35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80
```

```
Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 99
<211> LENGTH: 113
<212> TYPE: PRT
<213> ORGANISM: Artificial Sequence
<220> FEATURE:
<223> OTHER INFORMATION: Synthetic light chain variable region of AT-Vk4

<400> SEQUENCE: 99

Asp Ile Gln Met Thr Gln Ser Pro Ser Ser Leu Ser Ala Ser Val Gly
 1               5                  10                  15

Asp Arg Val Thr Ile Thr Cys Lys Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 100
<211> LENGTH: 13
<212> TYPE: PRT
<213> ORGANISM: Artificial Sequence
<220> FEATURE:
<223> OTHER INFORMATION: Synthetic modified hinge region(U7-HC6)

<400> SEQUENCE: 100

Glu Pro Ser Cys Asp Lys His Cys Cys Pro Pro Cys Pro
 1               5                  10

<210> SEQ ID NO 101
<211> LENGTH: 13
<212> TYPE: PRT
<213> ORGANISM: Artificial Sequence
<220> FEATURE:
<223> OTHER INFORMATION: Synthetic modified hinge region(U6-HC7)

<400> SEQUENCE: 101

Glu Pro Lys Ser Cys Asp Cys His Cys Pro Pro Cys Pro
 1               5                  10

<210> SEQ ID NO 102
<211> LENGTH: 12
<212> TYPE: PRT
<213> ORGANISM: Artificial Sequence
<220> FEATURE:
<223> OTHER INFORMATION: Synthetic modified hinge region(U3-HC9)

<400> SEQUENCE: 102

Glu Arg Lys Cys Cys Val Glu Cys Pro Pro Cys Pro
```

```
                1               5                  10

<210> SEQ ID NO 103
<211> LENGTH: 14
<212> TYPE: PRT
<213> ORGANISM: Artificial Sequence
<220> FEATURE:
<223> OTHER INFORMATION: Synthetic modified hinge region(U6-HC8)

<400> SEQUENCE: 103

Glu Pro Arg Asp Cys Gly Cys Lys Pro Cys Pro Pro Cys Pro
 1               5                  10

<210> SEQ ID NO 104
<211> LENGTH: 13
<212> TYPE: PRT
<213> ORGANISM: Artificial Sequence
<220> FEATURE:
<223> OTHER INFORMATION: Synthetic modified hinge region(U8-HC5)

<400> SEQUENCE: 104

Glu Lys Cys Asp Lys Thr His Thr Cys Pro Pro Cys Pro
 1               5                  10

<210> SEQ ID NO 105
<211> LENGTH: 15
<212> TYPE: PRT
<213> ORGANISM: Artificial Sequence
<220> FEATURE:
<223> OTHER INFORMATION: Synthetic human hinge region

<400> SEQUENCE: 105

Glu Pro Lys Ser Cys Asp Lys Thr His Thr Cys Pro Pro Cys Pro
 1               5                  10                  15

<210> SEQ ID NO 106
<211> LENGTH: 17
<212> TYPE: PRT
<213> ORGANISM: Artificial Sequence
<220> FEATURE:
<223> OTHER INFORMATION: Synthetic CDR-L1 of antibody L3-11Y

<400> SEQUENCE: 106

Lys Ser Ser Gln Ser Leu Leu Ala Trp Gly Asn Gln Asn Asn Tyr Leu
 1               5                  10                  15

Ala

<210> SEQ ID NO 107
<211> LENGTH: 114
<212> TYPE: PRT
<213> ORGANISM: Artificial Sequence
<220> FEATURE:
<223> OTHER INFORMATION: Synthetic amino acid sequence of light chain
      variable region of antibody L3-11Y

<400> SEQUENCE: 107

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Trp
                20                  25                  30

Gly Asn Gln Asn Asn Tyr Leu Ala Trp Tyr Gln Gln Lys Pro Gly Lys
            35                  40                  45

Ala Pro Lys Met Leu Ile Ile Trp Ala Ser Thr Arg Val Ser Gly Val
        50                  55                  60
```

```
Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110

Lys Arg

<210> SEQ ID NO 108
<211> LENGTH: 220
<212> TYPE: PRT
<213> ORGANISM: Artificial Sequence
<220> FEATURE:
<223> OTHER INFORMATION: Synthetic amino acid sequence of light chain
      of antibody L3-11Y

<400> SEQUENCE: 108

Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Trp
                 20                  25                  30

Gly Asn Gln Asn Asn Tyr Leu Ala Trp Tyr Gln Gln Lys Pro Gly Lys
             35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 109
<211> LENGTH: 20
<212> TYPE: DNA
<213> ORGANISM: Artificial Sequence
<220> FEATURE:
<223> OTHER INFORMATION: Synthetic TFF1 sense primer

<400> SEQUENCE: 109
cccctggtgc ttctatccta                                             20

<210> SEQ ID NO 110
<211> LENGTH: 23
```

```
<212> TYPE: DNA
<213> ORGANISM: Artificial Sequence
<220> FEATURE:
<223> OTHER INFORMATION: Synthetic TFF1 antisense primer

<400> SEQUENCE: 110
gatccctgca gaagtgtcta aaa                                            23

<210> SEQ ID NO 111
<211> LENGTH: 25
<212> TYPE: DNA
<213> ORGANISM: Artificial Sequence
<220> FEATURE:
<223> OTHER INFORMATION: Synthetic Probe for TFF1 gene

<400> SEQUENCE: 111
agacagagac gtgtacagtg gcccc                                          25

<210> SEQ ID NO 112
<211> LENGTH: 25
<212> TYPE: DNA
<213> ORGANISM: Artificial Sequence
<220> FEATURE:
<223> OTHER INFORMATION: Synthetic Probe for TFF1 gene

<400> SEQUENCE: 112 gcccccgtg aaagacagaa ttgtg                                           25

<210> SEQ ID NO 113
<211> LENGTH: 25
<212> TYPE: DNA
<213> ORGANISM: Artificial Sequence
<220> FEATURE:
<223> OTHER INFORMATION: Synthetic Probe for TFF1 gene

<400> SEQUENCE: 113
aattgtggtt ttcctggtgt cacgc                                          25

<210> SEQ ID NO 114
<211> LENGTH: 25
<212> TYPE: DNA
<213> ORGANISM: Artificial Sequence
<220> FEATURE:
<223> OTHER INFORMATION: Synthetic Probe for TFF1 gene

<400> SEQUENCE: 114
gtgtgcaaat aagggctgct gtttc                                          25

<210> SEQ ID NO 115
<211> LENGTH: 25
<212> TYPE: DNA
<213> ORGANISM: Artificial Sequence
<220> FEATURE:
<223> OTHER INFORMATION: Synthetic Probe for TFF1 gene

<400> SEQUENCE: 115
ccctggtgct tctatcctaa tacca                                          25

<210> SEQ ID NO 116
<211> LENGTH: 25
<212> TYPE: DNA
<213> ORGANISM: Artificial Sequence
<220> FEATURE:
<223> OTHER INFORMATION: Synthetic Probe for TFF1 gene

<400> SEQUENCE: 116
```
cttctatcct aataccatcg acgtc                                          25

<210> SEQ ID NO 117
<211> LENGTH: 25
<212> TYPE: DNA
<213> ORGANISM: Artificial Sequence
<220> FEATURE:
<223> OTHER INFORMATION: Synthetic Probe for TFF1 gene

<400> SEQUENCE: 117
gacgtccctc cagaagagga gtgtg                                          25

<210> SEQ ID NO 118
<211> LENGTH: 25
<212> TYPE: DNA
<213> ORGANISM: Artificial Sequence
<220> FEATURE:
<223> OTHER INFORMATION: Synthetic Probe for TFF1 gene

<400> SEQUENCE: 118
agacacttct gcagggatct gcctg                                          25

<210> SEQ ID NO 119
<211> LENGTH: 25
<212> TYPE: DNA
<213> ORGANISM: Artificial Sequence
<220> FEATURE:
<223> OTHER INFORMATION: Synthetic Probe for TFF1 gene

<400> SEQUENCE: 119
cacggtgatt agtcccagag ctcgg                                          25

<210> SEQ ID NO 120
<211> LENGTH: 25
<212> TYPE: DNA
<213> ORGANISM: Artificial Sequence
<220> FEATURE:
<223> OTHER INFORMATION: Synthetic Probe for TFF1 gene

<400> SEQUENCE: 120
cctcggctca caacacagat tgact                                          25

<210> SEQ ID NO 121
<211> LENGTH: 25
<212> TYPE: DNA
<213> ORGANISM: Artificial Sequence
<220> FEATURE:
<223> OTHER INFORMATION: Synthetic Probe for TFF1 gene

<400> SEQUENCE: 121
gattgactgc tctgactttg actac                                          25

<210> SEQ ID NO 122
<211> LENGTH: 335
<212> TYPE: DNA
<213> ORGANISM: Artificial Sequence
<220> FEATURE:
<223> OTHER INFORMATION: Synthetic Target sequence of TFF1 gene

<400> SEQUENCE: 122
agacagagac gtgtacagtg gccccccgtg aaagacagaa ttgtggtttt cctggtgtca    60
cgccctccca gtgtgcaaat aagggctgct gtttcgacga caccgttcgt ggggtcccct   120
ggtgcttcta tcctaatacc atcgacgtcc ctccagaaga ggagtgtgaa ttttagacac   180
ttctgcaggg atctgcctgc atcctgacgg ggtgccgtcc ccagcacggt gattagtccc   240

```
agagctcggc tgccacctcc accggacacc tcagacacgc ttctgcagct gtgcctcggc    300
tcacaacaca gattgactgc tctgactttg actac                               335
```

<210> SEQ ID NO 123
<211> LENGTH: 442
<212> TYPE: PRT
<213> ORGANISM: Artificial Sequence
<220> FEATURE:
<223> OTHER INFORMATION: Synthetic Heavy chain of anti-c-Met antibody
      LY2875358

<400> SEQUENCE: 123

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Arg Val Asn Pro Asn Arg Gly Thr Thr Tyr Asn Gln Lys Phe
    50                  55                  60

Glu Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                85                  90                  95

Ala Arg Ala Asn Trp Leu Asp Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335
```

-continued

```
Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440

<210> SEQ ID NO 124
<211> LENGTH: 215
<212> TYPE: PRT
<213> ORGANISM: Artificial Sequence
<220> FEATURE:
<223> OTHER INFORMATION: Synthetic Light chain of anti-c-Met antibody
      LY2875358

<400> SEQUENCE: 124

Asp Ile Gln Met Thr Gln Ser Pro Ser Ser Leu Ser Ala Ser Val Gly
 1               5                  10                  15

Asp Arg Val Thr Ile Thr Cys Ser Val Ser Ser Ser Val Ser Ser Ile
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Val Tyr Ser Gly Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Asp Cys
    210                 215

<210> SEQ ID NO 125
<211> LENGTH: 114
<212> TYPE: PRT
<213> ORGANISM: Artificial Sequence
```

```
<220> FEATURE:
<223> OTHER INFORMATION: Synthetic light chain variable region of anti
      c-Met antibody

<400> SEQUENCE: 125

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp Tyr Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
             100                 105                 110

Lys Arg
```

BIOMARKER TFF1 FOR PREDICTING EFFECT OF C-MET INHIBITOR

CROSS-REFERENCE TO RELATED APPLICATIONS

This application claims the benefit of Korean Patent Application No. 10-2014-0008733 filed on Jan. 24, 2014 in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: One 141,706 bytes ASCII (Text) file named "719249_ST25_revised.TXT" created Jun. 14, 2016.

BACKGROUND OF THE INVENTION

1. Field

Provided is biomarker TFF1 for predicting and/or monitoring an effect of a c-Met inhibitor, a composition for predicting an effect of a c-Met inhibitor and/or selecting a subject for application of a c-Met inhibitor including a TFF1 detecting substance, a composition for monitoring an effect of a c-Met inhibitor including a TFF1 detecting substance, a method of predicting an effect of a c-Met inhibitor and/or selecting a subject for application of a c-Met inhibitor using TFF1, a method of monitoring an effect of a c-Met inhibitor using TFF1, and a method of treating and/or preventing cancer including administering a c-Met inhibitor to the selected subject.

2. Description of the Related Art

A biomarker generally refers to a measured characteristic which may be used as an indicator of some change caused in an organism by an external factor. Active studies have recently been made to apply biomarkers to the diagnosis of diseases, such as cancer, stroke, dementia, etc., and the prediction or monitoring of therapeutic effects of some agents. Among biomarkers relevant to drug development are pharmacodynamic markers (PD markers) for indicating whether drugs are functionally effective in vivo, and predictive markers for indicating the likely responsiveness to particular drugs before administration. The use of such markers is helpful in establishing the clinical strategy of drugs. For example, a predictive marker, designed to indicate sensitivity or resistance to drug action, may be applied to the selection of patients to allow for more effective drug therapy while the action mode of a drug in individual patients can be monitored with a pharmacodynamic marker, which together can lead to the establishment of effective therapeutic strategies. Further, even in the absence of a predictive marker, a pharmacodynamic marker permits the early monitoring of responses to a drug, thus discriminating a drug-effective group from a drug-ineffective group in an early stage. Consequentially, more effective and successful drug therapies can be established. In addition, when applied to the monitoring of responsiveness to a drug as a function of concentration, a pharmacodynamic marker can be an index for calculating suitable doses of the drug.

To date, cancer is one of the leading causes of death. Although the development of medical techniques has brought about a remarkable progress in cancer therapy, the 5-year survival rate has only improved by 10% over the past two decades. This is because cancer characteristics, such as rapid growth, metastasis, etc., make it difficult to diagnose and treat within a suitable time. The introduction of suitable biomarkers to cancer therapy would identify the characteristics of cancer to increase the opportunity of applying a suitable therapeutic in an optimal time, whereby cancer treatment could reach high success rates. For example, patients with lung cancer may differ from each other in cancer classification, genotype, and protein secretion, and thus must be treated with different, proper therapeutics. For chemotherapy using a specific drug, a corresponding biomarker, if present, would reduce the number of erroneous trials and increase possibility of success. In this regard, it is very important to explore biomarkers for predicting or monitoring the effect of anti-cancer therapeutics. A proper biomarker, if successfully exploited, can make a great contribution to the utility and value of anti-cancer drugs and the success rate of treatment with them.

c-Met is a hepatocyte growth factor (HGF) receptor. Hepatocyte growth factor (HGF) acts as a multi-functional cytokine which binds to the extracellular domain of the c-Met receptor to regulate cell division, cell motility, and morphogenesis in various normal and tumor cells. The c-Met receptor is a membrane receptor that possesses tyrosine kinase activity. c-Met is a proto-oncogene, per se, that encodes the representative receptor tyrosine kinase. Occasionally, it takes part in a variety of mechanisms responsible for the development of cancer, such as oncogenesis, cancer metastasis, the migration and invasion of cancer cells, angiogenesis, etc., irrespectively of the ligand HGF, and thus has attracted intensive attention as a target for anti-cancer therapy. Actually, targeted therapies, such as antibodies against c-Met, have been continuously developed.

A therapy with a developed c-Met targeting drug might be more effective treating cancer, with an elevated probability of success if there is a biomarker that is capable of predicting and monitoring the therapeutic effect of the drug to select patients suitable for the drug therapy and to monitor patient responses to the drug. Given, the biomarker could be applied to the establishment of effective therapeutic strategies.

BRIEF SUMMARY OF THE INVENTION

An embodiment provides a biomarker for predicting an effect of a c-Met inhibitor and/or selecting a subject for application of a c-Met inhibitor, including at least one selected from the group consisting of TFF1 and genes encoding TFF1.

Another embodiment provides a biomarker for monitoring an effect of a c-Met inhibitor, including at least one selected from the group consisting of TFF1 and genes encoding TFF1.

Another embodiment provides a composition and a kit for predicting an effect of a c-Met inhibitor and/or selecting a subject for application of a c-Met inhibitor, including a material interacting with at least one selected from the group consisting of TFF1 and genes encoding TFF1.

Another embodiment provides a composition and a kit for monitoring an effect of a c-Met inhibitor, including a material interacting with at least one selected from the group consisting of TFF1 and genes encoding TFF1.

Another embodiment provides a method of predicting an effect of a c-Met inhibitor and/or selecting a subject for application of a c-Met inhibitor, including measuring presence, level and/or mutation of at least one selected from the group consisting of TFF1 and genes encoding TFF1 in a biological sample.

Another embodiment provides a method of monitoring an effect of a c-Met inhibitor, including measuring presence, level and/or mutation of at least one selected from the group consisting of TFF1 and genes encoding TFF1 in a biological sample.

Another embodiment provides a pharmaceutical composition for combination therapy including a c-Met inhibitor and a TFF1 inhibitor. The pharmaceutical composition for combination therapy may be used for treating and/or preventing cancer.

Another embodiment provides a method of treating and/or preventing cancer in a subject, including co-administering a c-Met inhibitor and a TFF1 inhibitor to the subject.

DETAILED DESCRIPTION OF THE INVENTION

Figure 1:
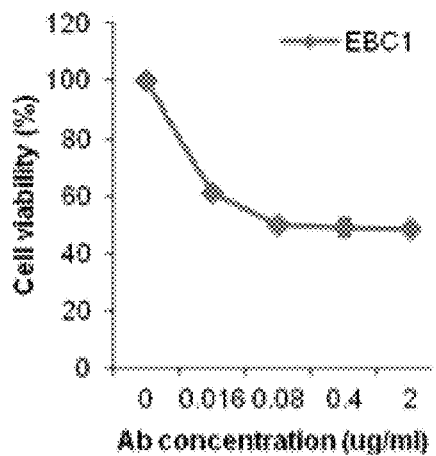
FIG. 1 is a set of graphs showing the proliferation level (cell viability) of lung cancer cell lines, when treated with an anti-c-Met antibody.
Figure 1:
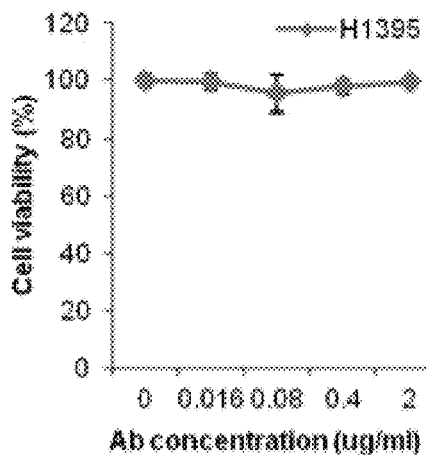
Figure 1:
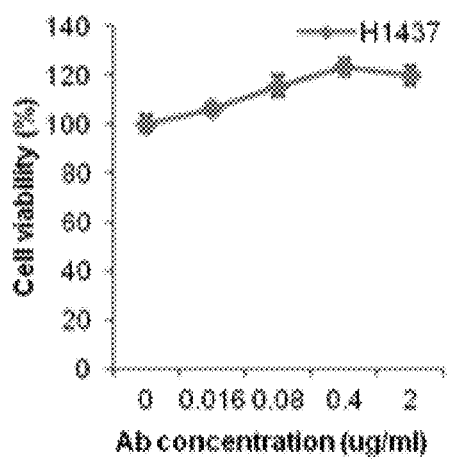
Figure 1:
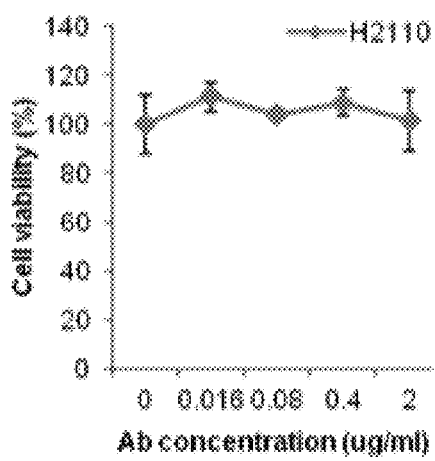
Figure 1:
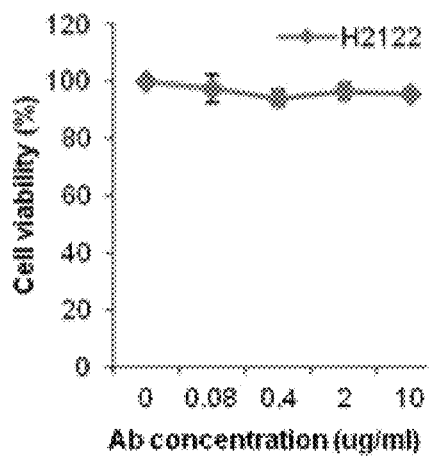
Figure 1:
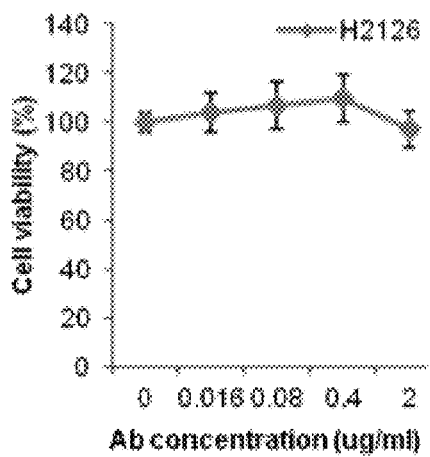

Provided is a use of Trefoil factor 1 (TFF1) protein or TFF1 gene, or both, in predicting the effect of a c-Met inhibitor in a subject, and/or monitoring induced resistance against a c-Met inhibitor administered to a subject.

Herein, the effect of a c-Met inhibitor may refer to the prevention, improvement, alleviation, and/or treatment of a c-Met related disease such as cancer. The effect of a c-Met inhibitor may refer to the effect of inhibiting proliferation of cancer cell or cancer tissue, killing cancer cells or cancer tissue, inhibiting migration and/or invasion of cancer cells, which is related to cancer metastasis, and the like.

TFF1 is expressed in and secreted from digestive organs. Without wishing to be bound to a particular theory or mechanism of action, it is believed that the responsiveness of a c-Met related disease to a c-Met inhibitor differs depending on the TFF1 expression level in the diseased cells. Also, it is believed that the changing profile between TFF1 expression levels in cells with and without treatment with a c-Met inhibitor or before and after treatment with a c-Met inhibitor differs depending on the responsiveness of the cells to a c-Met inhibitor. In particular, when the level of TFF1 or TFF1 gene in a biological sample is low, it can be confirmed that a c-Met inhibitor such as an anti-c-Met antibody can successfully exhibit its effect on the biological sample or a subject from which the biological sample is obtained. In addition, when resistance to a c-Met inhibitor such as an anti-c-Met antibody is induced, it can be observed that the level of TFF1 or TFF1 gene is increased. Thus, TIFF1 expression can be used both to select a disease or patient suitable for treatment with a c-Met inhibitor, and to monitor the potential build-up of resistance to the c-Met inhibitor during treatment.

That is, by measuring the TFF1 expression level in a biological sample, the effect of a c-Met inhibitor can be predicted, whereby a subject suitable for the application of the c-Met inhibitor can be selected. In addition, by measuring the change in the TFF1 expression level before and after treatment with a c-Met inhibitor, the induction of resistance to the c-Met inhibitor and/or the effect of the c-Met inhibitor on the treated subject/disease can be monitored, whereby it can be determined whether the application of the c-Met inhibitor should be continued or stopped. Based thereon, the use of TFF1 as a biomarker for predicting and/or monitoring an effect of a c-Met inhibitor is suggested.

The TFF1 may be originated from any mammal such as a primate (e.g., human, monkey), a rodent (e.g., mouse, rat), and the like. For example, the TFF1 may be selected from the group consisting of human TFF1 (e.g., NP_003216.1), mouse TFF1 (e.g., NP_033388.1), rat TFF1 (e.g., NP_476470.1), and any combination thereof. TFF1 gene (mRNA) (encoding TFF1 protein) may be selected from the group consisting of human TFF1 gene (e.g., NM_003225.2), mouse TFF1 gene (e.g., NM_009362.2), rat TFF1 gene (e.g., NM_057129.1), and any combination thereof, but not be limited thereto.

One embodiment provides a biomarker for predicting an effect of a c-Met inhibitor and/or selecting a subject for application of a c-Met inhibitor, the biomarker comprising at least one selected from the group consisting of TFF1 proteins and TFF1 genes.

Another embodiment provides a biomarker for monitoring an effect of a c-Met inhibitor, the biomarker comprising at least one selected from the group consisting of TFF1 proteins and TFF1 genes.

Another embodiment provides a composition and a kit for predicting an effect of a c-Met inhibitor and/or selecting a subject for application of a c-Met inhibitor, the composition and kit comprising a material interacting with at least one selected from the group consisting of TFF1 proteins and TFF1 genes.

Another embodiment provides a composition and a kit for monitoring an effect of a c-Met inhibitor, the composition and kit comprising a material interacting with at least one selected from the group consisting of TFF1 proteins and TFF1 genes.

Another embodiment provides a method of predicting an effect of a c-Met inhibitor and/or selecting a subject for application of a c-Met inhibitor, the method comprising measuring the level of at least one selected from the group consisting of TFF1 proteins and TFF1 genes in a biological sample.

Another embodiment provides a method of monitoring an effect of a c-Met inhibitor, comprising measuring the level of at least one selected from the group consisting of TFF1 proteins and TFF1 genes in a biological sample.

Another embodiment provides a method for preventing and/or treating cancer in a subject, comprising administering a c-Met inhibitor (e.g., an anti-c-Met antibody) to the subject, wherein the level of TFF1 protein or TFF1 gene in a biological sample (such as a cell, a tissue, body fluid, etc.) from the subject is low (wherein the term "low" is more specifically defined below), or the level of TFF1 protein or TFF1 gene in a biological sample (such as a cell, a tissue, body fluid, etc.) from the subject after treatment with the c-Met inhibitor is equal to or less than that before the treatment.

As used herein, the term "efficacy" of a c-Met inhibitor refers to a c-Met inhibitory effect and/or the pharmaceutical activity of a c-Met inhibitor resulting in the prevention, amelioration, reduction or treatment of a c-Met-related disease, for instance, a cancer. As regards cancer the efficacy refers to an anticancer effect, for example, an ability to induce the reduction or death of cancer cells or tissues, and the suppression of cancer cell migration and/or invasion responsible for cancer metastasis. In other word, the efficacy may refer to responsiveness of a subject, who is administered with a c-Met inhibitor, to the c-Met inhibitor.

As used herein, the term "predicting an efficacy of a c-Met inhibitor" may refer to determining whether or not or how much the c-Met inhibitor exhibits its desired efficacy (e.g., an antitumor or anticancer efficacy) on a subject who is treated therewith.

As used herein, the wording "a subject suitable for the application of the c-Met inhibitor" may refer to "a subject suitable for administration or treatment with a c-Met inhibitor" or "a subject with a disease (e.g., cancer) that is likely to respond to a c-Met inhibitor".

As used herein, the term "gene" refers to any nucleic acid encoding the protein (TFF1), whether genomic DNA, cDNA, or RNA (mRNA).

In this description, the term "monitoring an effect of a c-Met inhibitor" may refer to monitoring, evaluating, or verifying the effect of a c-Met inhibitor in a subject who is administered with the c-Met inhibitor. The term may refer to monitoring whether or not a c-Met inhibitor successfully exhibits its effect and/or whether or not resistance to a c-Met inhibitor is induced, after the c-Met inhibitor is administered to a subject.

In the method of predicting an effect of a c-Met inhibitor or a method of selecting a subject for application of a c-Met inhibitor, when the level of at least one selected from the group consisting of TFF1 proteins and TFF1 genes in a biological sample is low, it may be determined (predicted) that the c-Met inhibitor will successfully exhibit its effect in the biological sample or a subject from which the biological sample is obtained, or it may be determined that the biological sample or a subject from which the biological sample is obtained is suitable for the application of the c-Met inhibitor.

In this description, the term "TFF1 level" may refer to TFF1 expression level as measured by any suitable technique, such as mRNA expression of TFF1 gene, TFF1 protein amount, or TFF1 protein activity.

Therefore, the method of predicting an effect of a c-Met inhibitor may further comprise a step of determining (predicting) that the c-Met inhibitor will successfully exhibit its effect in a biological sample or a subject from which the biological sample is obtained, when the level of at least one selected from the group consisting of TFF1 proteins and TFF1 genes in the biological sample is low. In addition, the method of selecting a subject for application of a c-Met inhibitor may further comprise a step of determining that a biological sample or a subject from which the biological sample is obtained is suitable for the application of the c-Met inhibitor, when the level of at least one selected from the group consisting of TFF1 proteins and TFF1 genes in the biological sample is low.

As used herein, a "low" level of a TFF1 protein and/or TFF1 gene in a biological sample may refer to the absence of TFF1 protein and/or TFF1 gene expression (e.g., (e.g., based on DNA, cDNA, or mRNA levels) in the biological sample, or an amount of TFF1 protein and/or TFF1 gene expression (e.g., based on DNA, cDNA, or mRNA levels) in the biological sample (test sample) is lower than that of a reference sample, wherein the reference sample may refer to a biological sample (e.g., cells, tissues, body fluid, etc.) on which the c-Met inhibitor to be administered does not exhibit its effect (for example, an anticancer effect such as inhibiting of cancer cell proliferation, migration (metastasis), or invasion, or inducing cancer cell apoptosis, etc.), or a biological sample (e.g., cells, tissues, body fluid, etc.) separated (obtained) from a subject on which the c-Met inhibitor to be administered does not exhibit its effect (for example, an anticancer effect such as inhibiting of cancer cell proliferation, migration (metastasis), or invasion, or inducing cancer cell apoptosis, etc.).

In an embodiment, if the expression level of TFF1 gene (mRNA) is about 8.41 or less, for example, from about 0 to about 8.41, wherein the mRNA expression level may be measured by Affymetrix U133 Plus 2.0 array and expressed by intensity of a label (such as, fluorescent material) used in the assay, it can be determined (predicted) that the c-Met inhibitor will successfully exhibit its effect in a biological sample or a subject from which the biological sample is obtained.

The above expression level of TFF1 gene (mRNA) may be measured by Affymetrix U133 Plus 2.0 array (Affymetrix, Inc., Santa Clara, Calif.) according to a manufacturer's manual (e.g., "GeneChip 3' IVT PLUS Reagent Kit User Manual", the entire disclosure of which is hereby incorporated by reference). The expression level measured by Affymetrix U133 Plus 2.0 array is merely to illustrate the invention. The expression levels may also be measured any other general means for the gene expression level measurement (e.g., at least one selected from the group consisting of by polymerase chain reaction (PCR; e.g, qPCR, RT-PCR, RT-qPCR), fluorescent in situ hybridization (FISH), microarray assay (e.g., mRNA microarray, Illumina BeadArray microarray, RNA-seq array), northern blotting, or SAGE, and the like) using a primer, a probe, or an aptamer, which is capable of hybridizing with the gene or a part thereof (target sequence).

For example, when the gene expression level is measured by the means other than Affymetrix U133 Plus 2.0 array, the obtained result may be converted so that it corresponds to the result measured by the Affymetrix U133 Plus 2.0 array, to be applied to the method of predicting an effect of a c-Met inhibitor as described above. The term "conversion of the result so that it corresponds to the result measured by the Affymetrix U133 Plus 2.0 array" may be clear to a person of skilled in the relevant field.

In addition, the effect of a c-Met inhibitor can also be predicted by comparing the mRNA expression level of TFF1 gene to mRNA expression level of another gene. For example:

i) if the average mRNA expression level of TFF1 gene in a biological sample compared to that of GAPDH gene in the biological sample (average mRNA expression level of TFF1 gene/average mRNA expression level of GAPDH gene) is about 0.59 or less (e.g., about 0 to about 0.59), it can be predicted that the that the c-Met inhibitor will successfully exhibit its effect in the biological sample or a subject from which the biological sample is obtained;

ii) if the average mRNA expression level of TFF1 gene in a biological sample compared to that of HPRT1 gene in the biological sample (average mRNA expression level of TFF1 gene/average mRNA expression level of HPRT1 gene) is about 1.24 or less (e.g., about 0 to about 1.24), it can be predicted that the that the c-Met inhibitor will successfully exhibit its effect in the biological sample or a subject from which the biological sample is obtained; or iii) if the average mRNA expression level of TFF1 gene in a biological sample compared to that of 10 genes (EEF1A1, RPL23A, TPT1, HUWE1, MATR3, SRSF3, HNRNPC, SMARCA4, WDR90, and TUT1 genes) in the biological sample (average mRNA expression level of TFF1 gene/average mRNA expression level of the 10 genes) is about 0.72 or less (e.g., about 0 to about 0.72), it can be predicted that the that the c-Met inhibitor will successfully exhibit its effect in the biological sample or a subject from which the biological sample is obtained.

Therefore, all the methods described herein may further comprise measuring the mRNA level of at least one reference gene selected from the group consisting of GAPDH gene, HPRT1 gene, and 10 genes (EEF1A1, RPL23A, TPT1, HUWE1, MATR3, SRSF3, HNRNPC, SMARCA4, WDR90, and TUT1 genes) and comparing the mRNA levels of TFF1 gene and the reference gene.

All the above mRNA expression levels may be measured any general means for the gene expression level measurement (e.g., at least one selected from the group consisting of by polymerase chain reaction (PCR; e.g, qPCR, RT-PCR, RT-qPCR), fluorescent in situ hybridization (FISH), microarray assay (e.g., mRNA microarray, Illumina BeadArray microarray, RNA-seq array), northern blotting, or SAGE, and the like) using a primer, a probe, or an aptamer, which is capable of hybridizing with the gene or a part thereof (target sequence). For example, the above mRNA expression levels of the genes may be measured by Affymetrix U133 Plus 2.0 array (Affymetrix, Inc., Santa Clara, Calif.) according to a manufacturer's manual (e.g., "GeneChip 3' IVT PLUS Reagent Kit User Manual", the entire disclosure of which is hereby incorporated by reference). The expression levels measured by Affymetrix U133 Plus 2.0 array are merely to illustrate the invention.

For example, the level of a gene (e.g., full length DNA, cDNA, or mRNA) of interest may be measured by but not be limited to:

extracting RNA from a biological (or reference) sample;
synthesizing cDNA from the extracted RNA;
amplifying a DNA fragment (comprising target sequence; for example, in length of about 5 to about 1000 nucleotides (nt), e.g., about 10 to about 500 nt, about 20 to about 500 nt, about 20 to about 400 nt, about 20 to about 300 nt, about 20 to about 200 nt, about 50 to about 500 nt, about 50 to about 400 nt, about 50 to about 300 nt, or about 50 to about 200 nt) of the cDNA with a primer pair (e.g., a sense primer and an antisense primer), wherein each primer of the primer set is in length of about 5 to about 100 nt (e.g., about 5 to about 50 nt, about 5 to about 30 nt, about 10 to 30 nt, or about 10 to 25 nt) and capable of hybridizing with (complementary to) 3'- or 5'-terminus region (in size of about 5 to about 100 nt (e.g., about 5 to about 50 nt, about 5 to about 30 nt, about 10 to about 30 nt, or about 10 to 25 nt)) of the DNA fragment;

reacting (contacting) the DNA fragment and a probe or an aptamer in length of about 5 to about 100 nt, about 5 to about 50 nt, about 5 to about 30 nt, or about 5 to about 25 nt, which is labeled with a general label (such as, a fluorescent or luminescent material, a coloring substance (dye), etc.) and capable of hybridizing with (or complementary to) the DNA fragment or a part of the DNA fragment in length of about 5 to about 100 nt, about 5 to about 50 nt, about 5 to about 30 nt, or about 5 to about 25 nt; and measuring the level of the label (e.g., an intensity of the used label. such as, a fluorescent or luminescent material, a coloring substance (dye), etc.), to quantify the gene (e.g., full length DNA, cDNA, or mRNA) of interest.

In another embodiment, a method of monitoring (evaluating, or verifying) an effect of a c-Met inhibitor is provided, wherein the method comprises a step of measuring the level of at least one selected from the group consisting of TFF1 proteins and TFF1 genes in a biological sample. As described above, the method of monitoring an effect of a c-Met inhibitor may comprise confirming whether or not resistance to a c-Met inhibitor is induced.

In the method of monitoring an effect of a c-Met inhibitor, the levels of at least one selected from the group consisting of TFF1 proteins and TFF1 genes in a biological sample obtained from a subject who is treated (administered) with a c-Met inhibitor and in a biological sample obtained from a subject who is not treated (administered) with a c-Met inhibitor are respectively measured and compared to each other. When the level of at least one selected from the group consisting of TFF1 proteins and TFF1 genes in a biological sample obtained from a subject who is administered with the c-Met inhibitor (in the case of post-administration of c-Met inhibitor) is maintained or decreased compared to that of a biological sample obtained from a subject who is not administered with the c-Met inhibitor (in the case of pre-administration of c-Met inhibitor), it can be determined that the c-Met inhibitor exhibits its effect well in the subject who is administered with the c-Met inhibitor. When the level of at least one selected from the group consisting of TFF1 proteins and TFF1 genes in a biological sample obtained from a subject who is administered with the c-Met inhibitor (in the case of post-administration of c-Met inhibitor) is higher (increased) compared to that of a biological sample obtained from a subject who is not administered with the c-Met inhibitor (in the case of pre-administration of c-Met inhibitor), it is determined that the c-Met inhibitor does not exert its efficacy in the subject to whom the c-Met inhibitor was administered, or that the patient (or disease of the patient) is resistant to the c-Met inhibitor.

Alternatively, in the method of monitoring an effect of a c-Met inhibitor, the levels of at least one selected from the group consisting of TFF1 proteins and TFF1 genes in biological samples obtained from a subject before and after a c-Met inhibitor is treated (administered) are respectively measured and compared to each other. When the level of at least one selected from the group consisting of TFF1 proteins and TFF1 genes in a biological sample obtained from a subject after the c-Met inhibitor is treated is increased compared to that of a biological sample obtained from a subject before the c-Met inhibitor is treated, it can be determined that resistance to the c-Met inhibitor is induced in the subject by administration with the c-Met inhibitor.

Therefore, the method of monitoring an effect of a c-Met inhibitor may further comprise, after the step of measuring the level of TFF1 protein and/or TFF1 gene, 1) comparing the levels of at least one selected from the group consisting of TFF1 proteins and TFF1 genes i) in a biological sample (c-Met inhibitor-treated biological sample) obtained from a subject who is administered with a c-Met inhibitor (or after administration with a c-Met inhibitor) and ii) in a biological sample (c-Met inhibitor-untreated biological sample) obtained from a subject who is not administered with a c-Met inhibitor (or before administration with a c-Met inhibitor), to each other; and/or 2) determining that the c-Met inhibitor exhibits its effect well in the subject after administered with the c-Met inhibitor, when the level of at least one selected from the group consisting of TFF1 proteins and TFF1 genes of the c-Met inhibitor-treated biological sample (or after administration with a c-Met inhibitor) is maintained or decreased compared to that of the c-Met inhibitor-untreated biological sample (or before administration with a c-Met inhibitor) (in this case, it may be determined to maintain (continue) the administration of a c-Met inhibitor to the subject); and/or 3) determining that the c-Met inhibitor does not exert its efficacy or a resistance to the c-Met inhibitor occurs (or is induced) in the biological sample-derived subject when the level of at least one selected from the group consisting of TFF1 proteins and TFF1 genes in the c-Met inhibitor-treated biological sample is increased (in this case, it may be determined to stop the administration of a c-Met inhibitor to the subject). The c-Met inhibitor may be an anti-c-Met antibody.

In the method of monitoring an effect of a c-Met inhibitor, the c-Met inhibitor-treated sample and c-Met inhibitor-untreated sample may respectively refer to a whole biological sample after (treated sample) and before (c-Met inhibitor-untreated sample) the c-Met inhibitor is treated, or respectively refer to a part (treated sample) of a biological sample which is administered (treated) with the c-Met inhibitor and a part (c-Met inhibitor-untreated sample) of the biological sample which is not administered (treated) with the c-Met inhibitor (e.g., treated with a vehicle only). As used herein, unless stated otherwise, the c-Met inhibitor-treated sample and the biological sample treated with the c-Met inhibitor (or post-treatment biological sample) may be understood to share the same meaning with each other, and the c-Met inhibitor-untreated sample and the biological sample prior to treatment with the c-Met inhibitor (or pre-treatment biological sample) may also be understood to share the same meaning with each other.

The method of monitoring an effect of a c-Met inhibitor may be applied to determining whether the administration of the c-Met inhibitor can be continued or should be stopped, and/or to determining the proper administration conditions (e.g., dosage, interval of administration interval, the number of administration, and the like) of the c-Met inhibitor. For example, if the level of at least one selected from the group consisting of TFF1 proteins and TFF1 genes in a c-Met inhibitor-treated sample and a biological sample after treated with a c-Met inhibitor is decreased compared to that of the c-Met inhibitor-untreated sample and the biological sample before treated with a c-Met inhibitor (for example, if the level of at least one selected from the group consisting of TFF1 proteins and TFF1 genes in a c-Met inhibitor-treated sample and a biological sample after treated with a c-Met inhibitor is about 0 to about 80 wt %, about 0 to about 70 wt %, about 0 to about 60 wt %, about 0 to about 50 wt %, about 0 to about 40 wt %, about 0 to about 30 wt %, about 0 to about 20 wt %, or about 0 to about 10 wt %, compared to that of the c-Met inhibitor-untreated sample and the biological sample before treated with a c-Met inhibitor), it can be determined that the c-Met inhibitor can be continuously administered to a subject from which the sample is obtained. In addition, the administration condition of a c-Met inhibitor, wherein the level of at least one selected from the group consisting of TFF1 proteins and TFF1 genes in a c-Met inhibitor-treated sample and a biological sample after treated with a c-Met inhibitor is decreased compared to that of the c-Met inhibitor-untreated sample and the biological sample before treated with a c-Met inhibitor (for example, if the level of at least one selected from the group consisting of TFF1 proteins and TFF1 genes in a c-Met inhibitor-treated sample and a biological sample after treated with a c-Met inhibitor is about 0 to about 80 wt %, about 0 to about 70 wt %, about 0 to about 60 wt %, about 0 to about 50 wt %, about 0 to about 40 wt %, about 0 to about 30 wt %, about 0 to about 20 wt %, or about 0 to about 10 wt %, compared to that of the c-Met inhibitor-untreated sample and the biological sample before treated with a c-Met inhibitor), can be determined as a suitable administration condition of the c-Met inhibitor to the individual subject. The administration condition may be at least one selected from the group consisting of administration dosage, administration interval, the number of administration, and the like, or any combination thereof.

In the method of predicting an effect of a c-Met inhibitor, selecting a subject for the application of a c-Met inhibitor, and/or monitoring an effect of a c-Met inhibitor, the step of measuring the level of at least one selected from the group consisting of TFF1 proteins and TFF1 genes may comprise ii) applying (adding, treating, reacting, or contacting) a material interacting with the at least one selected from the group consisting of TFF1 proteins and TFF1 genes to a biological sample to allow reacting; and iii) quantitatively analyzing (quantifying) the at least one selected from the group consisting of TFF1 proteins and TFF1 genes in the resulting reaction mixture to determine (measure) a level of at least one selected from the group consisting of TFF1 proteins and TFF1 genes. The method may further comprise i) providing the biological sample before step ii). The step i) of providing the biological sample may comprise obtaining (isolating) a biological sample from a subject. In step ii), as will be further elucidated below, the interacting material may be at least one selected from the group consisting of a chemical (small molecular chemical; including general label such as a fluorescent, a dye, etc.), a protein (antibodies, aptamers, etc.), a peptide, a polynucleotide, and an oligonucleotide (DNA, RNA, etc.), which all (specifically) bind to all or a part of TFF1 proteins or TFF1 genes, and optionally, may be conjugated with a label, such as a fluorescent or a coloring substance (dye), a secondary antibody, a bead (e.g., a magnetic bead or polystyrene bead), or any combination thereof. For example, the interacting material may be at least one selected from the group consisting of a chemical (small molecule) specifically binding to TFF1 protein or TFF1 gene, an antibody against a TFF1 protein or a TFF1 gene, an aptamer against TFF1 protein or TFF1 gene, a primer or a primer pair specifically binding to a part or entirety of a TFF1 gene, and a probe specifically binding to a part or entirety of a TFF1 gene. The step ii) may be configured to form a complex of an interacting material and a TFF1 protein or TFF1 gene in a biological sample by applying (adding) the interacting material to the biological sample. In step iii), the reaction mixture obtained from step ii) may comprise a complex resulting from interaction (binding) between at least one selected from the group consisting of TFF1 proteins and TFF1 genes and the interacting material. The quantitatively analyzing step may comprise quantifying a) the complex formed in step ii), b) a label conjugated to the complex, and/or c) the TFF1 protein or TFF1 gene which is separated (isolated) from the complex after separating (isolating) the complex from the biological sample.

The quantification of the TFF1 protein may be conducted by any general method for protein quantification, such as ELISA and the like, and the quantification of the TFF1 gene may be conducted by any general method for gene (DNA or RNA) quantification, such as PCR (e.g., qPCR, RT-PCR, RT-qPCR), microarray (e.g., mRNA microarray, Illumina BeadArray microarray, RNA-seq array), Northern blotting, SAGE, and the like, but not be limited thereto.

Levels of TFF1 protein and/or TFF1 genes may be measured by any general protein or gene assay using a material interacting with the proteins or the genes. The material interacting with TFF1 protein and/or TFF1 genes may be a chemical (any small molecule except proteins and nucleic acid), an antibody, or an aptamer, a polynucleotide (e.g., a primer, a probe, an aptamer), which specifically bind to a part or entirety of TFF1 protein or TFF1 gene, or any combination thereof. For example, the levels of TFF1 protein may be measured by detecting enzymatic reactions, fluorescence, luminescence, and/or radioactivity using a chemical, an antibody, and/or an aptamer, which specifically bind to TFF1 protein.

In detail, the level of TFF1 protein may be determined (measured) using an analysis technique selected from the group consisting of, but not limited to, immunochromatography, immunohistochemistry (IHC), immunohistochemical staining, enzyme linked immunosorbent assay (ELISA), radioimmunoassay (RIA), enzyme immunoassay (EIA), fluorescence immunoassay (FIA), luminescence immunoassay (LIA), Western blotting, microarray, flow cytometry assay (e.g., Cytometric Bead Array (CBA) assay (BD biosciences), Intracellular staining, etc.), Luminex assay, surface plasmon resonance (SPR), and the like. For example the TFF1 protein may be quantified by measuring value of a proper parameter (e.g., absorbance at certain wavelength, intensity of used fluorescent material, darkness or width of obtained band, etc.) proper to the used assay and determining the amount (concentration) of TFF1 protein corresponding to the value of parameter using a reference curve provided in the used assay.

In addition, the level of a gene (DNA, cDNA, or mRNA) encoding TFF1 may be measured by any general gene assay using a primer, a probe, or an aptamer, which is capable of hybridizing with the gene, for example, by polymerase chain reaction (PCR; e.g, qPCR, RT-PCR, RT-qPCR), fluorescent in situ hybridization (FISH), microarray assay (e.g., mRNA microarray, Illumina BeadArray microarray, RNA-seq array), Northern blotting, or SAGE, but not be limited thereto. In one embodiment, the primer may be designed to detect a fragment of contiguous base pairs with the gene encoding TFF1 (full-length DNA, cDNA or mRNA), for example, a fragment of about 5 to about 1000 bp, e.g., about 10 to about 500 bp, about 20 to about 500 bp, about 20 to about 400 bp, about 20 to about 300 bp, about 20 to about 200 bp, about 50 to about 500 bp, about 50 to about 400 bp, about 50 to about 300 bp, or about 50 to about 200 bp, and may be a pair of primers comprising or consisting essentially of nucleotide sequences which are respectively capable of hybridizing with (e.g., complementary to) 3'- and 5'-terminal regions ranging in size from about 5 to about 100 bp, e.g., about 5 to about 50 bp, about 5 to about 30 bp, about 10 to about 30 bp or about 10 to 25 bp. The probe or the aptamer capable of hybridizing with the gene may comprise or consist essentially of a nucleotide sequence with a size of from about 5 to about 100 bp, from about 5 to about 50 bp, from about 5 to about 30 bp, or from about 5 to about 25 bp, which is capable of hybridizing with (or complementary to) a fragment (about 5 to about 100 bp, about 5 to about 50 bp, about 5 to about 30 bp, or about 5 to about 25 bp) of the TFF1-encoding gene (full-length DNA, cDNA or mRNA). As used herein, the term "capable of hybridizing" may refer to complementarily binding to a specific region of the gene, with a sequence complementarity of 80% or higher, e.g., 90% or higher, 95% or higher, 98% or higher, 99% or higher, or 100% between the primer, probe or aptamer and the gene region. The examples of primers and probes are illustrated in Tables 1 and 2, but not limited thereto.

For example, the level of TFF1 gene (e.g., full length DNA, cDNA, or mRNA) may be measured by but not be limited to:

extracting RNA from a biological (or reference) sample;
synthesizing cDNA from the extracted RNA;
amplifying a DNA fragment (comprising target sequence; for example, in length of about 5 to about 1000 nucleotides (nt), e.g., about 10 to about 500 nt, about 20 to about 500 nt, about 20 to about 400 nt, about 20 to about 300 nt, about 20 to about 200 nt, about 50 to about 500 nt, about 50 to about 400 nt, about 50 to about 300 nt, or about 50 to about 200 nt) of the cDNA with a primer pair (e.g., a sense primer and an antisense primer), wherein each primer of the primer set is in length of about 5 to about 100 nt (e.g., about 5 to about 50 nt, about 5 to about 30 nt, about 10 to 30 nt, or about 10 to 25 nt) and capable of hybridizing with (complementary to) 3'- or 5'-terminus region (in size of about 5 to about 100 nt (e.g., about 5 to about 50 nt, about 5 to about 30 nt, about 10 to about 30 nt, or about 10 to 25 nt)) of the DNA fragment;

reacting (contacting) the DNA fragment and a probe or an aptamer in length of about 5 to about 100 nt, about 5 to about 50 nt, about 5 to about 30 nt, or about 5 to about 25 nt, which is labeled with a general label (such as, a fluorescent or luminescent material, a coloring substance (dye), etc.) and capable of hybridizing with (or complementary to) the DNA fragment or a part of the DNA fragment in length of about 5 to about 100 nt, about 5 to about 50 nt, about 5 to about 30 nt, or about 5 to about 25 nt; and measuring the level of the label (e.g., an intensity of the used label. such as, a fluorescent or luminescent material, a coloring substance (dye), etc.), to quantify the TFF1 gene (e.g., full length DNA, cDNA, or mRNA).

For example, the expression level of human TFF1 gene (full length DNA, cDNA, or mRNA) may be measured using at least one selected from the following probes (SEQ ID NOs: 111-121) and/or primers (SEQ ID NOs: 109 and 110), as summarized in Tables 1 and 2:

TABLE 1

Target Sequence of human TFF1 gene (mRNA: NM_003225.2) and Probes therefor

Target Sequence
(SEQ ID NO: 122)
agacagagacgtgtacagtggcccccgtgaaagacagaattgtggttttcctggtgtcacgccctcccagtg
tgcaaataagggctgctgtttcgacgacaccgttcgtggggtccctggtgcttctatcctaataccatcgac
gtccctccagaagaggagtgtgaattttagacacttctgcagggatctgcctgcatcctgacggggtgccgtc
cccagcacggtgattagtcccagagctcggctgccacctccaccggacacctcagacacgcttctgcagctgt
gcctcggctcacaacacagattgactgctctgactttgactac

| Probe Sequence (5'-3') | SEQ ID NO | Probe X | Probe Y | Probe Interrrogation Position | Target Strandedness |
| --- | --- | --- | --- | --- | --- |
| AGACAGAGACGTGTACAGTGGCCCC | 111 | 881 | 121 | 132 | Antisense |
| GCCCCCCGTGAAAGACAGAATTGTG | 112 | 110 | 485 | 152 | Antisense |
| AATTGTGGTTTTCCTGGTGTCACGC | 113 | 357 | 291 | 170 | Antisense |
| GTGTGCAAATAAGGGCTGCTGTTTC | 114 | 767 | 781 | 202 | Antisense |
| CCCTGGTGCTTCTATCCTAATACCA | 115 | 1043 | 427 | 248 | Antisense |
| CTTCTATCCTAATACCATCGACGTC | 116 | 499 | 361 | 256 | Antisense |
| GACGTCCCTCCAGAAGAGGAGTGTG | 117 | 692 | 617 | 275 | Antisense |
| AGACACTTCTGCAGGGATCTGCCTG | 118 | 459 | 121 | 306 | Antisense |
| CACGGTGATTAGTCCCAGAGCTCGG | 119 | 1064 | 315 | 356 | Antisense |
| CCTCGGCTCACAACACAGATTGACT | 120 | 771 | 445 | 425 | Antisense |
| GATTGACTGCTCTGACTTTGACTAC | 121 | 863 | 693 | 442 | Antisense |

TABLE 2

Primer for human TFF1 gene

| | | |
| --- | --- | --- |
| Sense Primer | 5'-cccctggtgcttctatccta-3' | SEQ ID NO: 109 |
| Antisense Primer | 5'-gatccctgcagaagtgtctaaaa-3' | SEQ ID NO: 110 |

Figure 10:
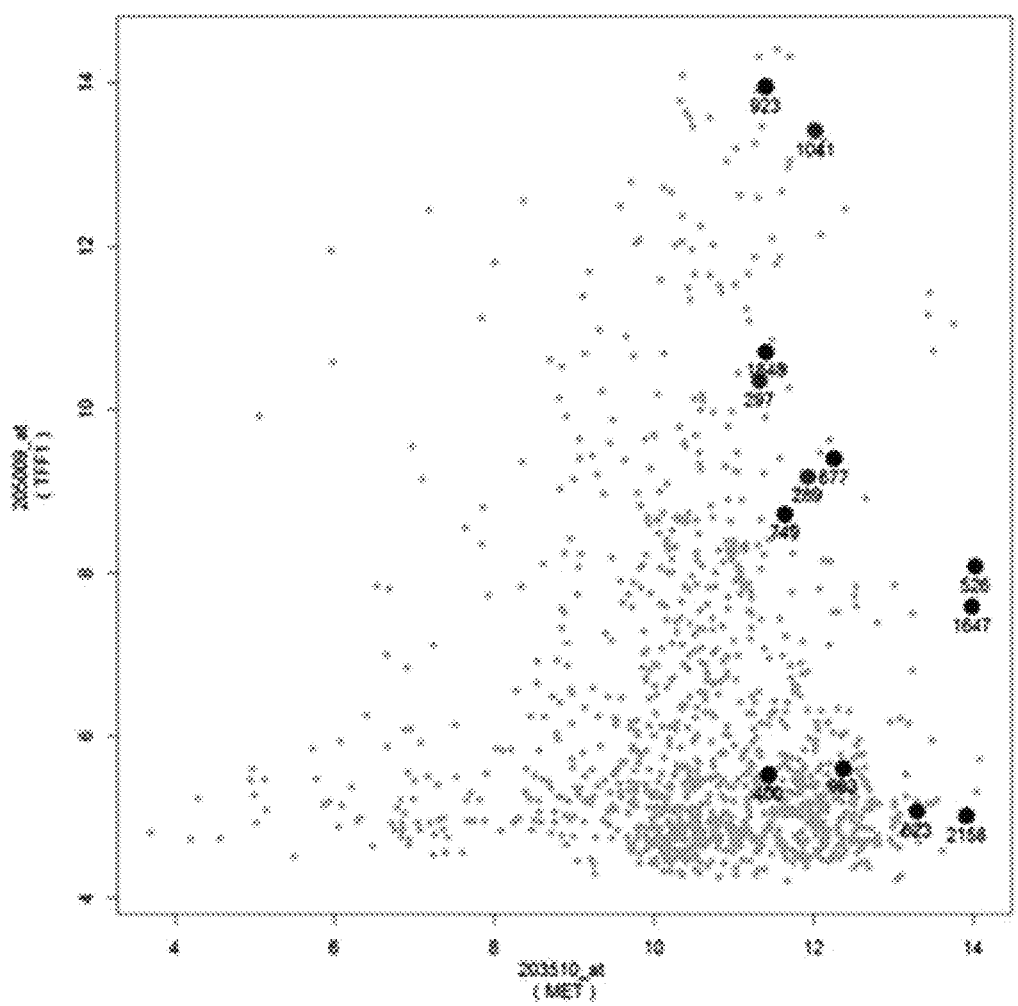
FIG. 10 is a graph showing the level of c-Met mRNA (Y-axis) and the level of TFF1 mRNA (X-axis) in anti-c-Met antibody efficient groups (spots 526, 1647, 623, and 2158) and anti-c-Met antibody non-efficient groups (the other spots).

Considering the characteristics of therapy using a c-Met inhibitor such as an anti-c-Met antibody, a c-Met expression of a certain level or more may be a prerequisite for exhibition of an effect of a c-Met inhibitor (see FIG. 10). Therefore, c-Met or a gene encoding c-Met can be used as a marker for predicting or monitoring an effect of a c-Met inhibitor, or selecting a subject for application of a c-Met inhibitor, alone or in combination with TFF1 or TFF1 gene.

Accordingly, the composition or kit for predicting or monitoring an effect of a c-Met inhibitor, or selecting a subject for application of a c-Met inhibitor may further comprise a material capable of interacting with at least one selected from the group consisting of c-Met and genes encoding c-Met in addition to a material interacting with the at least one selected from the group consisting of TFF1 proteins and TFF1 genes. The "material interacting with c-Met or genes encoding c-Met" may be a chemical (any small molecule except proteins and nucleic acid), an antibody, or an aptamer, a polynucleotide (e.g., a primer, a probe, an aptamer), which specifically bind to a part or entirety of TFF1 protein or TFF1 gene, or any combination thereof, and optionally, may be conjugated with a label, such as a fluorescent or a coloring substance (dye).

In addition, the method of predicting or monitoring an effect of a c-Met inhibitor, or selecting a subject for application of a c-Met inhibitor may further comprise measuring the level of c-Met protein and/or c-Met gene (e.g., full-length DNA, cDNA, mRNA) in a biological sample obtained from a subject, wherein the biological sample may be the same with that used in measuring the level of TFF1 protein and/or TFF1 gene. Details of the measuring step are as described above. The steps of measuring the level of TFF1 protein and/or TFF1 gene and the level of c-Met protein and/or c-Met gene are performed simultaneously or subsequently in any order. For example, a western blotting technique may be employed. In this regard, when a predetermined amount (e.g., 10 µg) of intracellular proteins obtained from a biological sample (e.g., cancer cells or cancer tissues) is loaded and exposed on the membrane for a certain time (e.g., 30 sec), the detection of a band may indicate that a prerequisite so that a c-Met inhibitor can exhibit its effect is established (satisfied). In another embodiment, when a biological sample is found to have a c-Met mRNA level of about 13.5 or higher, about 13.6 or higher, or about 13.78 or higher, as measured by Affymetrix array according to a manufacturer's manual, it can be determined that a prerequisite for the c-Met inhibitor therapy may be established. Cancer cells characterized by a high expression level of c-Met may comprise cells from lung cancer, breast cancer, brain cancer, stomach cancer, liver cancer, and kidney cancer. However, any other cancer cell, although obtained from different kind of cancer, may be a target of the c-Met inhibitor therapy if it expresses a high level of c-Met depending on individual subject.

In another embodiment, a biological sample used in the method of predicting or monitoring an effect of a c-Met inhibitor, or selecting a subject for application of a c-Met inhibitor may be a tissue, a cell or body fluid (blood, plasma, serum, urine, saliva, etc.) which shows a high expression level of c-Met, for example, a c-Met level of about 13.5 or higher, about 13.6 or higher, or about 13.78 or higher, as measured by Affymetrix array.

The subject to be administered with a c-Met inhibitor may be anyone who is suitable for application of the c-Met inhibitor, and may be any mammal such as a primate (e.g., human, monkey, etc.), a rodent (e.g., rat, mouse, etc.), or any other mammal. The subject may be a cancer patient. The biological sample may be at least one selected from the group consisting of a cell, a tissue, body fluid (blood, plasma, serum, urine, saliva, etc.), and the like, for example blood or serum, which is separated (isolated) from the subject or artificially cultured.

The method of predicting, monitoring, or selecting may further comprise administering a c-Met inhibitor to a subject, who is selected by the selecting method, or who is predicted or monitored that a c-Met inhibitor exerts its efficacy therein.

Another embodiment provides a method of inhibiting c-Met, comprising administering a c-Met inhibitor to a subject who has a low level of TFF1 protein and/or TFF1 gene (wherein the high level is defined above) and/or shows an equal or decreased level of TFF1 protein and/or TFF1 gene after administration of a c-Met inhibitor (compared to before administration of the c-Met inhibitor). The subject may be 1) selected by the above method for selecting a subject suitable for the application of a c-Met inhibitor or 2) determined by the above method of monitoring efficacy of a c-Met inhibitor as a subject wherein a c-Met inhibitor exerts its efficacy thereon.

Another embodiment provides a method of preventing and/or treating cancer, comprising a c-Met inhibitor to a subject who has a low level of TFF1 protein and/or TFF1 gene (wherein the high level is defined above) and/or shows an equal or decreased level of TFF1 protein and/or TFF1 gene after administration of a c-Met inhibitor (compared to before administration of the c-Met inhibitor). The subject may be 1) selected by the above method for selecting a subject suitable for the application of a c-Met inhibitor or 2) determined by the above method of monitoring efficacy of a c-Met inhibitor as a subject wherein a c-Met inhibitor exert its efficacy thereon.

The method of inhibiting c-Met or the method of preventing and/treating cancer may further comprise selecting a subject for application of a c-Met inhibitor, prior to the administering step. Details of the selection are as described above. The c-Met inhibitor may be an anti-c-Met antibody.

In an embodiment, the method of inhibiting c-Met or preventing and/or treating cancer may comprise:
identifying a subject for application of a c-Met inhibitor; and
administering a c-Met inhibitor to the subject.

The c-Met inhibitor may be administered in a pharmaceutically effect amount.

In another embodiment, the method of inhibiting c-Met or preventing and/or treating cancer may comprise:
selecting a subject for application of a c-Met inhibitor by measuring the level of TFF1 protein and/or TFF1 gene in a biological sample obtained from a subject; and
administering a c-Met inhibitor to the selected subject for application of a c-Met inhibitor.

The c-Met inhibitor may be administered in a pharmaceutically effect amount.

The administration condition, such as administration dosage, administration interval, and/or the number of administration, may be a suitable condition which is determined in a method of monitoring an effect of a c-Met inhibitor, as described above.

Figure 5:
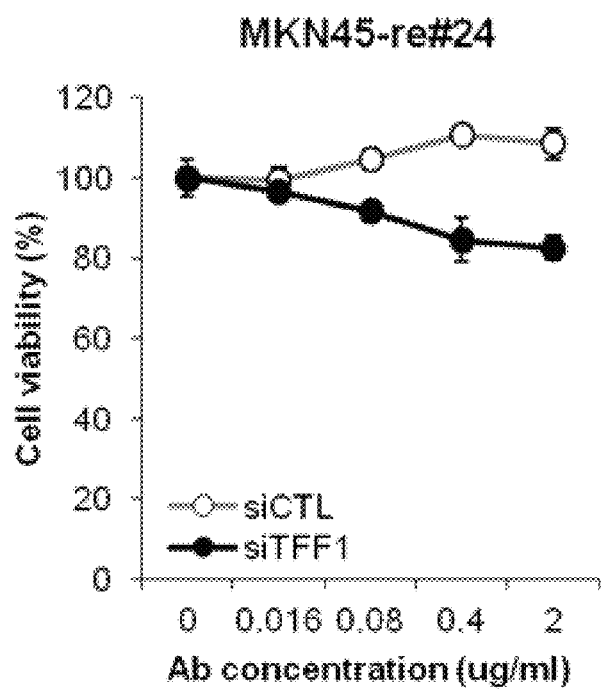
FIG. 5 is a graph showing the proliferation level (cell viability) of anti-c-Met antibody resistance-induced MKN45 cells when the expression of TFF1 in the cells is inhibited.
Figure 8:
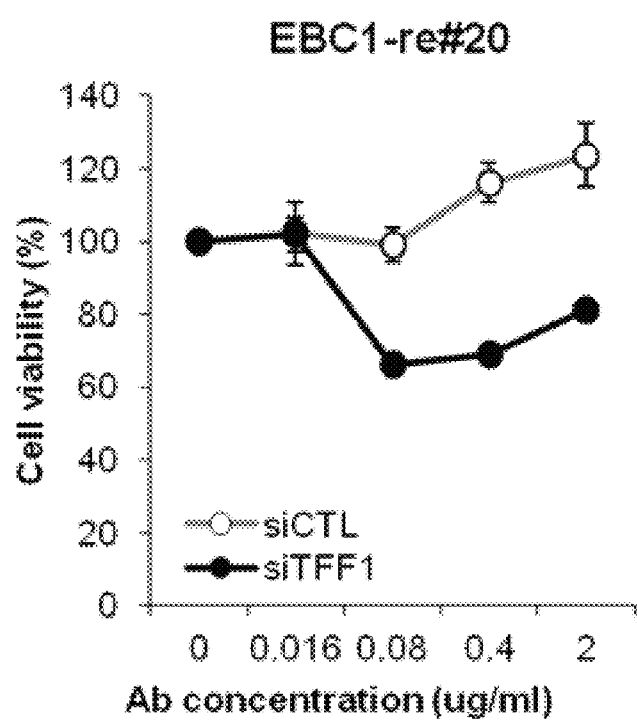
FIG. 8 is a graph showing the proliferation level (cell viability) of anti-c-Met antibody resistance-induced EBC1 cells when the expression of TFF1 in the cells is inhibited.

When c-Met and TFF1 are inhibited together, a cancer therapeutic effect, for example a therapeutic effect on a c-Met inhibitor resistant cancer, is increased compared to the case that c-Met is inhibited alone (see FIGS. 5 and 8).

Therefore, another embodiment provides a pharmaceutical composition for combination administration for preventing and/or treating cancer comprising a c-Met inhibitor and a TFF1 inhibitor.

In one embodiment, the pharmaceutical composition for combination administration may be in a form for simultaneous administration of two drugs comprising a mixture of a c-Met inhibitor and a TFF1 inhibitor. In another embodiment, the pharmaceutical composition for combination administration may be in a form of simultaneous or sequential administration of a c-Met inhibitor and a TFF1 inhibitor being individually formulated. In this case, the pharmaceutical composition for combination administration may be a pharmaceutical composition for combination administration for simultaneous or sequential administration comprising a first pharmaceutical composition containing a pharmaceutically effective amount of an anti-c-Met antibody and a second pharmaceutical composition containing a pharmaceutically effective amount of an inhibitor against the target substance. In the case of sequential administration, it can be performed in any order. The c-Met inhibitor and TFF1 inhibitor may be respectively used in amounts that are pharmaceutically effective when combined, which amount may be determined by the skilled medical practitioner or medical researcher.

Another embodiment provides a kit useful for preventing and/or treating a cancer, comprising a first pharmaceutical composition comprising a c-Met inhibitor as an active ingredient, a second pharmaceutical composition comprising a TFF1 inhibitor as an active ingredient, and a package container. The c-Met inhibitor and TFF1 inhibitor may be used in amounts that are pharmaceutically effective when combined, which amount may be determined by the skilled medical practitioner or medical researcher. The package container can be any container that holds or otherwise links the two compositions in individual containers together in a single unit (e.g., a box that holds both containers, or plastic wrap that binds both containers together), or the package container may be a single, divided container having at least two chambers that each hold one of the two compositions.

A method of combination therapy for preventing and/or treating a cancer also is provided. The method may comprise co-administering a c-Met inhibitor and a TFF1 inhibitor to a subject in need of the prevention and/or treatment of cancer. The c-Met inhibitor and TFF1 inhibitor may be administered in amounts that are pharmaceutically effective when combined, which amount may be determined by the skilled medical practitioner or medical researcher. The method may further comprise, prior to the co-administration step, a step of identifying a subject in need of the prevention and/or treatment of cancer. The step of identifying may be conducted by any manners and/or methods known to relevant field for identifying whether or not a subject needs the prevention and/or treatment of cancer. For example, the step of identifying may include diagnosing a subject to have a cancer, or identifying a subject who is diagnosed as a cancer patient.

In one embodiment, the co-administration may be conducted by administering a mixed formulation of a c-Met inhibitor and a TFF1 inhibitor, as described herein. In another embodiment, the co-administration may be conducted by a first step of administering a c-Met inhibitor, and a second step of administering a TFF1 inhibitor, wherein the first and the second administration steps may be conducted simultaneously or sequentially. In case of the sequential administration, the first step and the second step may be performed in any order. The c-Met inhibitor and TFF1 inhibitor may be administered in amounts that are pharmaceutically effective when combined, which amount may be determined by the skilled medical practitioner or medical researcher.

In an embodiment, the TFF1 inhibitor may be any agent that inhibits the expression and/or function of TFF1 protein and/or TFF1 gene, and for example, may be at least one selected from the group consisting of a chemical, a protein, a peptide, a polynucleotide, and an oligonucleotide, wherein the agent specifically binds to TFF1 protein and/or TFF1 gene. For example, the TFF1 inhibitor may be at least one selected from the group consisting of an antibody, an aptamer, a chemical (small molecule), an antisense oligonucleotide, small interfering RNA (siRNA), small hairpin RNA (shRNA), and microRNA (miRNA), which specifically bind to TFF1 protein and/or TFF1 gene, or any combination thereof.

In all the methods described herein, the term "c-Met inhibitor" may refer to any agent capable of inhibiting activity and/or expression of c-Met, or blocking c-Met signaling by inhibiting a ligand of c-Met. In an particular embodiment, the c-Met inhibitor may be at least one selected from the group consisting of an anti-c-Met antibody or an antigen-binding fragment thereof, crizotinib (PF-02341066; 3-((R)-1-(2,6-dichloro-3-fluorophenyl)ethoxy)-5-(1-(piperidin-4-yl)-1H-pyrazol-4-yl)pyridin-2-amine), cabozantinib (XL-184; N-(4-(6,7-dimethoxyquinolin-4-yloxy)phenyl)-N-(4-fluorophenyl)cyclopropane-1,1-dicarboxamide), foretinib (N-(3-fluoro-4-(6-methoxy-7-(3-morpholinopropoxyl) quinolin-4-yloxy)phenyl)-N-(4-fluorophenyl)cyclopropane-1,1-dicarboxamide), PHA-665752((R,Z)-5-(2,6-dichlorobenzylsulfonyl)-3-((3,5-dimethyl-4-(2-(pyrrolidin-1-ylmethyl)pyrrolidine-1-carbonyl)-1H-pyrrol-2-yl) methylene)indolin-2-one), SU11274((Z)—N-(3-chlorophenyl)-3-((3,5-dimethyl-4-(1-methylpiperazine-4-carbonyl)-1H-pyrrol-2-yl)methylene)-N-methyl-2-oxoindoline-5-sulfonamide), SGX-523(6-(6-(1-methyl-1H-pyrazol-4-yl)-[1,2,4]triazolo[4,3-b]pyridazin-3-ylthio) quinoline), PF-04217903(2-(4-(3-(quinolin-6-ylmethyl)-3H-[1,2,3]triazolo[4,5-b]pyrazin-5-yl)-1H-pyrazol-1-yl) ethanol), EMD 1214063(Benzonitrile, 3-[1,6-Dihydro-1-[[3-[5-[(1-Methyl-4-Piperidinyl)Methoxy]-2-PyriMidinyl] Phenyl]Methyl]-6-Oxo-3-Pyridazinyl]), golvatinib (N-(2-fluoro-4-((2-(4-(4-methylpiperazin-1-yl)piperidine-1-carboxamido)pyridin-4-yl)oxy)phenyl)-N-(4-fluorophenyl) cyclopropane-1,1-dicarboxamide), INCB28060(2-fluoro-N-methyl-4-(7-(quinolin-6-ylmethyl)imidazo[1,2-b][1,2,4] triazin-2-yl)benzamide), MK-2461(N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl] sulfamide), tivantinib (ARQ 197; (3R,4R)-3-(5,6-Dihydro-4H-pyrrolo[3,2,1-ij]quinolin-1-yl)-4-(1H-indol-3-yl) pyrrolidine-2,5-dione), NVP-BVU972(6-[[6-(1-Methyl-1H-pyrazol-4-yl)imidazo[1,2-b]pyridazin-3-yl]methyl] quinoline), AMG458({1-(2-hydroxy-2-methylpropyl)-N-[5-(7-methoxyquinolin-4-yloxy)pyridin-2-yl]-5-methyl-3-oxo-2-phenyl-2,3-dihydro-1H-pyrazole-4-carboxamide}), BMS 794833(N-(4-((2-amino-3-chloropyridin-4-yl)oxy)-3-fluorophenyl)-5-(4-fluorophenyl)-4-oxo-1,4-dihydropyridine-3-carboxamide), BMS 777607(N-[4-[(2-Amino-3-chloropyridin-4-yl)oxy]-3-fluorophenyl]-4-ethoxy-1-(4-fluorophenyl)-2-oxo-1,2-dihydropyridine-3-carboxamide), MGCD-265 (N-(3-Fluoro-4-(2-(1-methyl-1-imidazol-4-yl) thieno[3,2-b]pyridin-7-yloxy)phenylcarbamothioyl)-2-phenylacetamide), AMG-208(7-Methoxy-4-[(6-phenyl-1,2,4-triazolo[4,3-b]pyridazin-3-yl)methoxy]quinoline), BMS-754807((2S)-1-[4-[(5-Cyclopropyl-1H-pyrazol-3-yl)amino] pyrrolo[2,1-f][1,2,4]triazin-2-yl]-N-(6-fluoro-3-pyridinyl)-2-methyl-2-pyrrolidinecarboxamide), JNJ-38877605(6-[Difluoro[6-(1-methyl-1H-pyrazol-4-yl)-1,2,4-triazolo[4,3-b]pyridazin-3-yl]methyl]quinoline), and pharmaceutically acceptable salts thereof, or any combination thereof.

The anti-c-Met antibody or an antigen-binding fragment thereof may be any antibody which specifically recognizes c-Met as an antigen and/or specifically binds to c-Met, or an antigen-binding fragment thereof. The antigen-binding fragment thereof may be at least one selected from the group consisting of scFv, (scFv)2, scFv-Fc, Fab, Fab', and F(ab')2 of an anti-c-Met antibody. For example, the anti-c-Met antibody may be any antibody that acts on c-Met to induce intracellular internalization and degradation of c-Met, or antigen-binding fragment thereof. The anti-c-Met antibody may recognize any specific region of c-Met, e.g., a specific region in the SEMA domain, as an epitope.

Herein, unless stated otherwise, the term "anti-c-Met antibody" may be intended to cover not only an anti-c-Met antibody in a complete form (e.g., an IgG form) but also its antigen-binding region.

"c-Met" or "c-Met protein" refers to a receptor tyrosine kinase (RTK) which binds hepatocyte growth factor (HGF). c-Met may be derived (obtained) from any species, particularly a mammal, for instance, primates such as human c-Met (e.g., GenBank Accession No. NP_000236), monkey c-Met (e.g., Macaca mulatta, GenBank Accession No. NP_001162100), or rodents such as mouse c-Met (e.g., GenBank Accession No. NP_032617.2), rat c-Met (e.g., GenBank Accession No. NP_113705.1), and the like. The c-Met protein may include a polypeptide encoded by the nucleotide sequence identified as GenBank Accession No. NM_000245, a polypeptide having the amino acid sequence identified as GenBank Accession No. NP_000236 or extracellular domains thereof. The receptor tyrosine kinase c-Met participates in various mechanisms, such as cancer incidence, metastasis, migration of cancer cells, invasion of cancer cells, angiogenesis, and the like.

c-Met, a receptor for hepatocyte growth factor (HGF), may be divided into three portions: extracellular, transmembrane, and intracellular. The extracellular portion is composed of an α-subunit and a β-subunit which are linked to each other through a disulfide bond, and includes a SEMA domain responsible for binding HGF, a PSI domain (plexin-semaphorins-integrin identity/homology domain) and an IPT domain (immunoglobulin-like fold shared by plexins and transcriptional factors domain). The SEMA domain of c-Met protein may have the amino acid sequence of SEQ ID NO: 79, and is an extracellular domain that functions to bind HGF. A specific region of the SEMA domain, that is, a region having the amino acid sequence of SEQ ID NO: 71, which corresponds to a range from amino acid residues 106 to 124 of the amino acid sequence of the SEMA domain (SEQ ID NO: 79), is a loop region between the second and the third propellers within the epitopes of the SEMA domain. This region acts as an epitope for the anti-c-Met antibody.

The term "epitope," as used herein, refers to an antigenic determinant, a part of an antigen recognized by an antibody. In one embodiment, the epitope may be a region including 5 or more contiguous (consecutive on primary, secondary (two-dimensional), or tertiary (three-dimensional) structure) amino acid residues within the SEMA domain (SEQ ID NO: 79) of c-Met protein, for instance, 5 to 19 contiguous amino acid residues within the amino acid sequence of SEQ ID NO: 71. For example, the epitope may be a polypeptide having 5 to 19 contiguous amino acids selected from among partial combinations of the amino acid sequence of SEQ ID NO: 71, wherein the polypeptide includes at least the amino acid sequence of SEQ ID NO: 73 (EEPSQ) which serves as an essential element for the epitope. For example, the epitope may be a polypeptide including, consisting essentially of, or consisting of the amino acid sequence of SEQ ID NO: 71, SEQ ID NO: 72, or SEQ ID NO: 73.

The epitope having the amino acid sequence of SEQ ID NO: 72 corresponds to the outermost part of the loop between the second and third propellers within the SEMA domain of a c-Met protein. The epitope having the amino acid sequence of SEQ ID NO: 73 is a site to which the antibody or antigen-binding fragment according to one embodiment most specifically binds.

Thus, the anti-c-Met antibody may specifically bind to an epitope which comprises 5 to 19 contiguous amino acids selected from among partial combinations of the amino acid sequence of SEQ ID NO: 71, including SEQ ID NO: 73 as an essential element. For example, the anti-c-Met antibody may specifically bind to an epitope comprising the amino acid sequence of SEQ ID NO: 71, SEQ ID NO: 72, or SEQ ID NO: 73.

In one embodiment, the anti-c-Met antibody or an antigen-binding fragment thereof may comprise or consist essentially of:

(i) at least one heavy chain complementarity determining region (CDR) selected from the group consisting of (a) a CDR-H1 comprising the amino acid sequence of SEQ ID NO: 4; (b) a CDR-H2 comprising the amino acid sequence of SEQ ID NO: 5, the amino acid sequence of SEQ ID NO: 2, or an amino acid sequence comprising 8-19 consecutive amino acids within the amino acid sequence of SEQ ID NO: 2 comprising amino acid residues from the $3^{rd}$ to $10^{th}$ positions of the amino acid sequence of SEQ ID NO: 2; and (c) a CDR-H3 comprising the amino acid sequence of SEQ ID NO: 6, the amino acid sequence of SEQ ID NO: 85, or an amino acid sequence comprising 6-13 consecutive amino acids within the amino acid sequence of SEQ ID NO: 85 comprising amino acid residues from the $1^{st}$ to $6^{th}$ positions of the amino acid sequence of SEQ ID NO: 85, or a heavy chain variable region comprising the at least one heavy chain complementarity determining region;

(ii) at least one light chain complementarity determining region (CDR) selected from the group consisting of (a) a CDR-L1 comprising the amino acid sequence of SEQ ID NO: 7, (b) a CDR-L2 comprising the amino acid sequence of SEQ ID NO: 8, and (c) a CDR-L3 comprising the amino acid sequence of SEQ ID NO: 9, the amino acid sequence of SEQ ID NO: 15, the amino acid sequence of SEQ ID NO: 86, or an amino acid sequence comprising 9-17 consecutive amino acids within the amino acid sequence of SEQ ID NO: 89 comprising amino acid residues from the $1^{st}$ to $9^{th}$ positions of the amino acid sequence of SEQ ID NO: 89, or a light chain variable region including the at least one light chain complementarity determining region;

(iii) a combination of the at least one heavy chain complementarity determining region and at least one light chain complementarity determining region; .or (iv) a combination of the heavy chain variable region and the light chain variable region.

Herein, the amino acid sequences of SEQ ID NOS: 4 to 9 are respectively represented by following Formulas I to VI, below:

$Xaa_1$-$Xaa_2$-Tyr-Tyr-Met-Ser (SEQ ID NO: 4),     Formula I wherein $Xaa_1$ is absent or Pro or Ser, and $Xaa_2$ is Glu or Asp, Arg-Asn-$Xaa_3$-$Xaa_4$-Asn-Gly-$Xaa_5$-Thr (SEQ ID NO: 5),     Formula II wherein $Xaa_3$ is Asn or Lys, $Xaa_4$ is Ala or Val, and $Xaa_5$ is Asn or Thr, Asp-Asn-Trp-Leu-$Xaa_6$-Tyr (SEQ ID NO: 6),     Formula III wherein $Xaa_6$ is Ser or Thr, Lys-Ser-Ser-$Xaa_7$-Ser-Leu-Leu-Ala-$Xaa_8$-Gly-Asn-$Xaa_9$-$Xaa_{10}$-Asn-Tyr-Leu-Ala (SEQ ID NO: 7),     Formula IV wherein $Xaa_7$ is His, Arg, Gln, or Lys, $Xaa_8$ is Ser or Trp, $Xaa_9$ is His or Gln, and $Xaa_{10}$ is Lys or Asn, Trp-$Xaa_{11}$-Ser-$Xaa_{12}$-Arg-Val-$Xaa_{13}$ (SEQ ID NO: 8),     Formula V wherein $Xaa_{11}$ is Ala or Gly, $Xaa_{12}$ is Thr or Lys, and $Xaa_{13}$ is Ser or Pro, and $Xaa_{14}$-Gln-Ser-Tyr-Ser-$Xaa_{15}$-Pro-$Xaa_{16}$-Thr (SEQ ID NO: 9),     Formula VI wherein $Xaa_{14}$ is Gly, Ala, or Gln, $Xaa_{15}$ is Arg, His, Ser, Ala, Gly, or Lys, and $Xaa_{16}$ is Leu, Tyr, Phe, or Met.

In one embodiment, the CDR-H1 may comprise an amino acid sequence selected from the group consisting of SEQ ID NO: 1, SEQ ID NO: 22, SEQ ID NO: 23, and SEQ ID NO: 24. The CDR-H2 may comprise an amino acid sequence selected from the group consisting of SEQ ID NO: 2, SEQ ID NO: 25, and SEQ ID NO: 26. The CDR-H3 may comprise an amino acid sequence selected from the group consisting of SEQ ID NO: 3, SEQ ID NO: 27, SEQ ID NO: 28, and SEQ ID NO: 85.

The CDR-L1 may comprise an amino acid sequence selected from the group consisting of SEQ ID NO: 10, SEQ ID NO: 29, SEQ ID NO: 30, SEQ ID NO: 31, SEQ ID NO: 32, SEQ ID NO: 33, and SEQ ID NO: 106. The CDR-L2 may comprise an amino acid sequence selected from the group consisting of SEQ ID NO: 11, SEQ ID NO: 34, SEQ ID NO: 35, and SEQ ID NO: 36. The CDR-L3 may comprise an amino acid sequence selected from the group consisting of SEQ ID NO: 12, SEQ ID NO: 13, SEQ ID NO: 14, SEQ ID NO: 15, SEQ ID NO: 16, SEQ ID NO: 37, SEQ ID NO: 86, and SEQ ID NO: 89.

In another embodiment, the anti-c-Met antibody or an antigen-binding fragment thereof may comprise or consisting essentially of:

a heavy variable region comprising or consisting essentially of a polypeptide (CDR-H1) comprising an amino acid sequence selected from the group consisting of SEQ ID NO: 1, SEQ ID NO: 22, SEQ ID NO: 23, and SEQ ID NO: 24, a polypeptide (CDR-H2) comprising an amino acid sequence selected from the group consisting of SEQ ID NO: 2, SEQ ID NO: 25, and SEQ ID NO: 26, and a polypeptide (CDR-H3) comprising an amino acid sequence selected from the group consisting of SEQ ID NO: 3, SEQ ID NO: 27, SEQ ID NO: 28, and SEQ ID NO: 85; and a light variable region comprising or consisting essentially of a polypeptide (CDR-L1) comprising an amino acid sequence selected from the group consisting of SEQ ID NO: 10, SEQ ID NO: 29, SEQ ID NO: 30, SEQ ID NO: 31, SEQ ID NO: 32, SEQ ID NO: 33, and SEQ ID NO: 106, a polypeptide (CDR-L2) comprising an amino acid sequence selected from the group consisting of SEQ ID NO: 11, SEQ ID NO: 34, SEQ ID NO: 35, and SEQ ID NO: 36, and a polypeptide (CDR-L3) comprising an amino acid sequence selected from the group consisting of SEQ ID NO: 12, SEQ ID NO: 13, SEQ ID NO: 14, SEQ ID NO: 15, SEQ ID NO: 16, SEQ ID NO: 37, SEQ ID NO: 86, and SEQ ID NO: 89.

In an embodiment, the anti-c-Met antibody or an antigen-binding fragment thereof may comprise or consist essentially of a heavy variable region comprising the amino acid sequence of SEQ ID NO: 17, SEQ ID NO: 74, SEQ ID NO: 87, SEQ ID NO: 90, SEQ ID NO: 91, SEQ ID NO: 92, SEQ ID NO: 93, or SEQ ID NO: 94, and a light variable region comprising the amino acid sequence of SEQ ID NO: 18, SEQ ID NO: 19, SEQ ID NO: 20, SEQ ID NO: 21, SEQ ID NO: 75, SEQ ID NO: 88, SEQ ID NO: 95, SEQ ID NO: 96, SEQ ID NO: 97, SEQ ID NO: 98, SEQ ID NO: 99, or SEQ ID NO: 107.

In another embodiment, the anti-c-Met antibody or an antigen-binding fragment may be Onartuzumab (MetMab), LY2875358 (Heavy chain: SEQ ID NO: 123; Light chain: SEQ ID NO: 124), Rilotumumab (AMG102), or an antigen-binding fragment thereof, and the like.

Animal-derived antibodies produced by immunizing non-immune animals with a desired antigen generally invoke immunogenicity when injected into humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

The most important thing in CDR grafting to produce humanized antibodies is choosing the optimized human antibodies for accepting CDRs of animal-derived antibodies. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The anti c-Met antibodies may be mouse-derived antibodies, mouse-human chimeric antibodies, humanized antibodies, or human antibodies. The antibodies or antigen-binding fragments thereof may be isolated from a living body or non-naturally occurring. The antibodies or antigen-binding fragments thereof may be recombinant or synthetic. The antibodies or antigen-binding fragments thereof may be monoclonal.

An intact antibody includes two full-length light chains and two full-length heavy chains, in which each light chain is linked to a heavy chain by disulfide bonds. The antibody includes a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2(γ2), gamma 3(γ3), gamma 4(γ4), alpha 1(α1), or alpha 2(α2). The light chain constant region is of either a kappa (κ) or lambda (λ) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDRs may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "antigen-binding fragment" used herein refers to fragments of an intact immunoglobulin including portions of a polypeptide including antigen-binding regions having the ability to specifically bind to the antigen. In one embodiment, the antigen-binding fragment may be selected from the group consisting of scFv, (scFv)$_2$, Fab, Fab', and F(ab')$_2$, but not be limited thereto.

Among the antigen-binding fragments, Fab that includes light chain and heavy chain variable regions, a light chain constant region, and a first heavy chain constant region $C_{H1}$, includes one antigen-binding site.

The Fab' fragment is different from the Fab fragment, in that Fab' includes a hinge region with at least one cysteine residue at the C-terminal of $C_{H1}$.

The F(ab')$_2$ antibody is formed through disulfide bridging of the cysteine residues in the hinge region of the Fab' fragment. Fv is the smallest antibody fragment with only a heavy chain variable region and a light chain variable region. Recombination techniques of generating the Fv fragment are widely known in the art.

Two-chain Fv includes a heavy chain variable region and a light chain region which are linked by a non-covalent bond. Single-chain Fv generally includes a heavy chain variable region and a light chain variable region which are linked by a covalent bond via a peptide linker or linked at the C-terminals to have a dimer structure like the two-chain Fv. The peptide linker may be a polypeptide comprising 1 to 100 or 2 to 50 amino acids, wherein the amino acids may be selected from any amino acids without limitation.

The antigen-binding fragments may be attainable using protease (for example, the Fab fragment may be obtained by restricted cleavage of a whole antibody with papain, and the F(ab')$_2$ fragment may be obtained by cleavage with pepsin), or may be prepared by using a genetic recombination technique.

In the anti-c-Met antibody, the portion of the light chain and the heavy chain portion other than the CDRs, the light chain variable region and the heavy chain variable region (e.g., the light chain constant region and the heavy chain constant region) may be from any subtype of immunoglobulin (e.g., IgA, IgD, IgE, IgG (IgG1, IgG2, IgG3, IgG4), IgM, etc.).

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin may be replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the anti-c-Met antibody or an antigen-binding fragment thereof may be modified by the deletion, insertion, addition, or substitution of at least one (e.g., two, three, four, five, six, seven, eight, nine, or ten) amino acid residue of the amino acid sequence of the hinge region so that it exhibits enhanced antigen-binding efficiency. For example, the antibody may include a hinge region including the amino acid sequence of SEQ ID NO: 100 (U7-HC6), 101 (U6-HC7), 102 (U3-HC9), 103 (U6-HC8), or 104 (U8-HC5), or a hinge region including the amino acid sequence of SEQ ID NO: 105 (non-modified human hinge). Preferably, the hinge region includes the amino acid sequence of SEQ ID NO: 100 or 101.

In one embodiment, the anti-c-Met antibody may be a monoclonal antibody. The monoclonal antibody may be produced by the hybridoma cell line deposited with the Korean Cell Line Research Foundation, an international depository authority located at Yungun-Dong, Jongno-Gu, Seoul, Korea, on Oct. 6, 2009, under Accession No. KCLRF-BP-00220, which binds specifically to the extracellular region of c-Met protein (refer to Korean Patent Publication No. 2011-0047698, the entire disclosure of which is incorporated herein by reference). The anti-c-Met antibody may include all the antibodies defined in Korean Patent Publication No. 2011-0047698.

By way of further example, the anti-c-Met antibody may comprise or consist essentially of:

(a) a heavy chain comprising an amino acid sequence selected from the group consisting of the amino acid sequence of SEQ ID NO: 62 (wherein the amino acid sequence from amino acid residues from the $1^{st}$ to $17^{th}$ positions is a signal peptide), the amino acid sequence from the $18^{th}$ to $462^{nd}$ positions of SEQ ID NO: 62, the amino acid sequence of SEQ ID NO: 64 (wherein the amino acid sequence from the $1^{st}$ to $17^{th}$ positions is a signal peptide), the amino acid sequence from the $18^{th}$ to $461^{st}$ positions of SEQ ID NO: 64, the amino acid sequence of SEQ ID NO: 66 (wherein the amino acid sequence from the $1^{st}$ to $17^{th}$ positions is a signal peptide), and the amino acid sequence from the $18^{th}$ to $460^{th}$ positions of SEQ ID NO: 66; and (b) a light chain comprising an amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of SEQ ID NO: 68, the amino acid sequence of SEQ ID NO: 70 (wherein the amino acid sequence from the $1^{st}$ to $20^{th}$ positions is a signal peptide), the amino acid sequence from the $21^{st}$ to $240^{th}$ positions of SEQ ID NO: 70, and the amino acid sequence of SEQ ID NO: 108.

For example, the anti-c-Met antibody may be selected from the group consisting of:

(i) an antibody comprising (a) a heavy chain comprising the amino acid sequence of SEQ ID NO: 62 or the amino acid sequence from the $18^{th}$ to $462^{nd}$ positions of SEQ ID NO: 62 and (b) a light chain comprising the amino acid sequence of SEQ ID NO: 68 or the amino acid sequence from the $21^{st}$ to $240^{th}$ positions of SEQ ID NO: 68;

(ii) an antibody comprising (a) a heavy chain comprising the amino acid sequence of SEQ ID NO: 64 or the amino acid sequence from the $18^{th}$ to $461^{st}$ positions of SEQ ID NO: 64 and (b) a light chain including the amino acid sequence of SEQ ID NO: 68 or the amino acid sequence from the $21^{st}$ to $240^{th}$ positions of SEQ ID NO: 68;

(iii) an antibody comprising (a) a heavy chain comprising the amino acid sequence of SEQ ID NO: 66 or the amino acid sequence from the $18^{th}$ to $460^{th}$ positions of SEQ ID NO: 66 and (b) a light chain comprising the amino acid sequence of SEQ ID NO: 68 or the amino acid sequence from the $21^{st}$ to $240^{th}$ positions of SEQ ID NO: 68;

(iv) an antibody comprising (a) a heavy chain comprising the amino acid sequence of SEQ ID NO: 62 or the amino acid sequence from the $18^{th}$ to $462^{nd}$ positions of SEQ ID NO: 62 and (b) a light chain including the amino acid sequence of SEQ ID NO: 70 or the amino acid sequence from the $21^{st}$ to $240^{th}$ positions of SEQ ID NO: 70;

(v) an antibody comprising a heavy chain comprising (a) the amino acid sequence of SEQ ID NO: 64 or the amino acid sequence from the $18^{th}$ to $461^{st}$ positions of SEQ ID NO: 64 and (b) a light chain comprising the amino acid sequence of SEQ ID NO: 70 or the amino acid sequence from the $21^{st}$ to $240^{th}$ positions of SEQ ID NO: 70;

(v) an antibody comprising (a) a heavy chain comprising the amino acid sequence of SEQ ID NO: 66 or the amino acid sequence from the $18^{th}$ to $460^{th}$ positions of SEQ ID NO: 66 and (b) a light chain comprising the amino acid sequence of SEQ ID NO: 70 or the amino acid sequence from the $21^{st}$ to $240^{th}$ positions of SEQ ID NO: 70;

(vi) an antibody comprising (a) a heavy chain comprising the amino acid sequence of SEQ ID NO: 62 or the amino acid sequence from the $18^{th}$ to $462^{nd}$ positions of SEQ ID NO: 62 and (b) a light chain comprising the amino acid sequence of SEQ ID NO: 108;

(vii) an antibody comprising (a) a heavy chain comprising the amino acid sequence of SEQ ID NO: 64 or the amino acid sequence from the $18^{th}$ to $461^{st}$ positions of SEQ ID NO: 64 and (b) a light chain comprising the amino acid sequence of SEQ ID NO: 108; and (viii) an antibody comprising (a) a heavy chain comprising the amino acid sequence of SEQ ID NO: 66 or the amino acid sequence from the $18^{th}$ to $460^{th}$ positions of SEQ ID NO: 66 and (b) a light chain comprising the amino acid sequence of SEQ ID NO: 108.

The polypeptide comprising the amino acid sequence of SEQ ID NO: 70 is a light chain including human kappa (κ) constant region, and the polypeptide comprising the amino acid sequence of SEQ ID NO: 68 is a polypeptide obtained by replacing histidine at position 62 (corresponding to position 36 of SEQ ID NO: 68 according to kabat numbering) of the polypeptide comprising the amino acid sequence of SEQ ID NO: 70 with tyrosine. The production yield of the antibodies may be increased by the replacement. The polypeptide comprising the amino acid sequence of SEQ ID NO: 108 is a polypeptide obtained by replacing serine at position 32 (position 27e according to kabat numbering in the amino acid sequence from amino acid residues 21 to 240 of SEQ ID NO: 68; positioned within CDR-L1) of SEQ ID NO: 108 with tryptophan. By such replacement, antibodies and antibody fragments including such sequences exhibit increased activities, such as c-Met biding affinity, c-Met degradation activity, Akt phosphorylation inhibition, and the like.

In another embodiment, the anti c-Met antibody may comprising a light chain complementarity determining region comprising the amino acid sequence of SEQ ID NO: 106, a light chain variable region comprising the amino acid sequence of SEQ ID NO: 107, or a light chain comprising the amino acid sequence of SEQ ID NO: 108.

The c-Met inhibitor may be applied (administered) together with a pharmaceutically acceptable carrier. The pharmaceutically acceptable carrier may be those commonly used for the formulation of the inhibitor (e.g., antibodies), which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. The c-Met inhibitor may further comprise one or more selected from the group consisting of a lubricant, a wetting agent, a sweetener, a flavor enhancer, an emulsifying agent, a suspension agent, and preservative.

The c-Met inhibitor may be administered orally or parenterally. The parenteral administration may selected from the group consisting of intravenous injection, subcutaneous injection, muscular injection, intraperitoneal injection, endothelial administration, local administration, intranasal administration, intrapulmonary administration, and rectal administration. Since oral administration leads to digestion of proteins or peptides, the c-Met inhibitor for oral administration must be coated or formulated to prevent digestion in stomach. In addition, the c-Met inhibitor may be administered using an optional device that enables an active substance to be delivered to target cells.

The term "the pharmaceutically effective amount" as used herein may refer to an amount of which the active ingredient can exert pharmaceutically significant effects. The pharmaceutically effective amount of the c-Met inhibitor for a single dose may be prescribed in a variety of ways, depending on factors such as formulation methods, administration manners, age of patients, body weight of patients, gender of patients, pathologic conditions of patients, diets, administration time, administration interval, administration route, excretion speed, and reaction sensitivity. For example, the pharmaceutically effective amount of the c-Met inhibitor for a single dose may be in ranges of 0.001 to 100 mg/kg, or 0.02 to 10 mg/kg, but not limited thereto. The pharmaceutically effective amount for the single dose may be formulated into a single formulation in a unit dosage form or formulated in suitably divided dosage forms, or it may be manufactured to be contained in a multiple dosage container.

The c-Met inhibitor may be used in the prevention and/or treatment of a cancer and/or metastasis of cancer. The cancer may be associated with over-expression and/or abnormal activation of c-Met. The cancer may be a solid cancer or a blood cancer. For example, the cancer may be, but not limited to, one or more selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastric cancer, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, and the like. The cancer may be a primary cancer or a metastatic cancer. The cancer may be a cancer (e.g., a solid cancer such as gastric cancer, lung cancer, etc.), which is resistant to a c-Met inhibitor (e.g., an existing c-Met inhibitor), such as an anti-c-Met antibody.

The prevention and/or treatment of cancer may be achieved by at least one effect of the c-Met inhibitor selected from cancer cell death, inhibition of cancer cell proliferation, inhibition of migration, invasion, or metastasis of cancer, improvement of symptoms associated with cancer, etc.

In this description, the following effects, for example, may be expected:

1) By measuring the expression level of TFF1 gene in cancer tissue of a subject, it can be predicted whether or not an anti-c-Met antibody can exhibit its anticancer effect on the subject. Therefore, TFF1 can be useful as a predictive marker and contribute to selection of a subject suitable for application of the anti-c-Met antibody thereby increasing the chance of clinical success. In a concept of individual-customized therapy, unnecessary treatment can be minimized and the therapeutic effect can be maximized, in c-Met targeting therapy.

2) It can be conformed whether or not an anti-c-Met antibody can exhibit its anticancer effect on a subject, by measuring the level of TFF1 in a blood sample. TFF1 is a secretory protein, and thus, it can be measured in a blood sample.

3) By periodic measurement of TFF1, it can also be monitored whether or not a resistance to an anti-c-Met antibody is induced in a subject. Through such monitoring of resistance, the administration strategy of the anti-c-Met antibody, such as administration interval, manner, and the like, can be properly regulated thereby increasing the efficiency of therapy using the antibody. T TFF1 is a secretory protein, and thus, it can be measured in a blood sample, which makes it possible to readily monitor the effect by other manner than biopsy.

4) When an anti-c-Met antibody is co-administered with a TFF1 inhibitor, a considerable anticancer effect can be achieved, even on a cancer on which an anti-c-Met antibody alone cannot exhibit anticancer effect due to resistance to the antibody, which suggests a manner to overcome resistance to an anti-c-Met antibody and/or to improve the efficacy of an anti-c-Met antibody.

EXAMPLES

Hereafter, the present disclosure will be described in detail by examples.

The following examples are intended merely to illustrate the invention and are not to be construed as restricting the invention.

Reference Example: Construction of Anti-C-Met Antibody 1.1. Production of "AbF46", a Mouse Antibody to c-Met
1.1.1. Immunization of Mice To obtain immunized mice necessary for the development of a hybridoma cell line, each of five BALB/c mice (Japan SLC, Inc.), 4 to 6 weeks old, was intraperitoneally injected with a mixture of 100 μg of human c-Met/Fc fusion protein (R&D Systems) and one volume of complete Freund's adjuvant. Two weeks after the injection, a second intraperitoneal injection was conducted on the same mice with a mixture of 50 μg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of a Hybridoma

Three days before cell fusion, BALB/c mice (Japan SLC, Inc.) were immunized with an intraperitoneal injection of a mixture of 50 μg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1 \times 10^8$ cells) were mixed with myeloma cells (Sp2/0) ($1 \times 10^8$ cells), followed by spinning to yield a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1\sim2 \times 10^5$ cells/mL in a selection medium (HAT medium). 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 μL, (2 μg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 μL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 6, 2009, with Accession No. KCLRF-BP-00220 according to the Budapest Treaty (refer to Korean Patent Laid-Open Publication No. 2011-0047698).

1.1.4. Production and Purification of a Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) FBS (fetal bovine serum) were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with a filter (Amicon). The antibody was stored in PBS before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Reference Example 1.1.4 by replacing the constant region, but not the variable region responsible for antibody specificity, with an amino sequence of the human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a vector from the pOptiVEC™-TOPO TA Cloning Kit enclosed in an OptiCHO™ Antibody Express Kit (Cat no. 12762-019, Invitrogen), and a vector from the pcDNA™3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/mL. After 24 hours, when the cell number reached to $1 \times 10^6$ cells/mL, the transient expression was performed. A transfection was performed by a liposomal reagent method using Freestyle™ MAX reagent (Invitrogen), wherein in a 15 mL tube, the DNA was provided in the mixture ratio of 1:1 (heavy chain DNA:light chain DNA) and mixed with 2 mL of OptiPro™ SFM (Invitrogen) (A). In another 15 mL tube, 100 μL of Freestyle™ MAX reagent and 2 mL of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST search (online via NCBI) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Hereupon, back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has an identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Hereupon, back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a BLAST search. As a result, VK2-40 was selected. VL and VK2-40 of the mouse antibody AbF46 were found to have a identity/homology of 61% at an amino acid level. CDR-L1, CDR-L2, and CDR-L3 of the mouse antibody were defined according to Kabat numbering and introduced into the framework of VK2-1. Back mutations were conducted at positions 36 (Y→H), 46 (L→M), and 49 (Y→I) on H3-light.

For use in designing H4-light (SEQ ID NO: 46), human antibody frameworks were analyzed. A BLAST search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Hereupon, back mutations were conducted at positions 36 (Y→H), 46 (L→M), and 49 (Y→I) on H4-light.

Thereafter, DNA fragments having the heavy chain nucleotide sequences (H1-heavy: SEQ ID NO: 47, H3-heavy: SEQ ID NO: 48, H4-heavy: SEQ ID NO: 49) and DNA fragments having the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a vector from the pOptiVEC™-TOPO TA Cloning Kit enclosed in an OptiCHO™ Antibody Express Kit (Cat no. 12762-019, Invitrogen) and a vector from the pcDNA™3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/mL, the transient expression was performed. A transfection was performed by a liposomal reagent method using Freestyle™ MAX reagent (Invitrogen), wherein in a 15 mL tube, the DNA was provided in the mixture ratio of 1:1 (heavy chain DNA:light chain DNA) and mixed with 2 mL of OptiPro™ SFM (invtrogen) (A). In another 15 mL tube, 100 μL of Freestyle™ MAX reagent and 2 mL of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples comprised a combination of H4-heavy (SEQ ID NO: 42) and H4-light (SEQ ID NO: 46).

1.4. Construction of scFV Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker comprising the amino acid sequence "GLGGLGGGGSGGGGSGGSSGVGS" (SEQ ID NO: 54). A polynucleotide sequence (SEQ ID NO: 55) encoding the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation

1.5.1. Selection of Target CDRs and Synthesis of Primers

The affinity maturation of huAbF46 was achieved. First, six complementary determining regions (CDRs) were defined according to Kabat numbering. The CDRs are given in Table 3 below.

TABLE 3

| CDR | Amino Acid Sequence |
| --- | --- |
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After maturation of the affinity of the constructed libraries for c-Met, the nucleotide sequence of scFv from each clone was analyzed. The nucleotide sequences thus obtained are summarized in Table 4 and were converted into IgG forms. Four antibodies which were respectively produced from clones L3-1, L3-2, L3-3, and L3-5 were used in the subsequent experiments.

TABLE 4

| Clone | Library constructed | CDR Sequence |
| --- | --- | --- |
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment comprising L3-1-derived CDR-L3: SEQ ID NO: 58, DNA fragment comprising L3-2-derived CDR-L3: SEQ ID NO: 59, DNA fragment comprising L3-3-derived CDR-L3: SEQ ID NO: 60, and DNA fragment comprising L3-5-derived CDR-L3: SEQ ID NO: 61) were digested with EcoRI (NEB, R0101S) and XhoI (NEB, R0146S) before cloning into a vector from the pOptiVEC™-TOPO TA Cloning Kit enclosed in an OptiCHO™ Antibody Express Kit (Cat no. 12762-019, Invitrogen) and a vector from the pcDNA™3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/mL. After 24 hours, when the cell number reached to $1 \times 10^6$ cells/mL, the transient expression was performed. A transfection was performed by a liposomal reagent method using Freestyle™ MAX reagent (Invitrogen), wherein in a 15 mL tube, the DNA was provided in the mixture ratio of 1:1 (heavy chain DNA:light chain DNA) and mixed with 2 mL of OptiPro™ SFM (Invitrogen) (A). I In another 15 mL tube, 100 µL of Freestyle™ MAX reagent and 2 mL of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain comprising the heavy chain variable region of huAbF46-H4-A1, U6-HC7 hinge, and the constant region of human IgG1 constant region, and a light chain comprising the light chain variable region of huAbF46-H4-A1 and human kappa constant region. The antibody huAbF46-H4-A1 (IgG2 hinge) was composed of a heavy chain comprising a heavy chain variable region, a human IgG2 hinge region, and a human IgG1 constant region, and a light chain comprising the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain comprising the light variable region of huAbF46-H4-A1 and a human kappa constant region. Hereupon, the histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 region, a polynucleotide (SEQ ID NO: 67) encoding a polypeptide (SEQ ID NO: 66) composed of the heavy chain variable region of huAbF46-H4-A1, a human IgG2 region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a vector from the pOptiVEC™-TOPO TA Cloning Kit enclosed in an OptiCHO™ Antibody Express Kit (Cat no. 12762-019, Invitrogen) while DNA fragments having light chain nucleotide sequences were inserted into a vector from the pcDNA™3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/mL. After 24 hours, when the cell number reached to $1 \times 10^6$ cells/mL, the transient expression was performed. A transfection was performed by a liposomal reagent method using Freestyle™ MAX reagent (Invitrogen), wherein in a 15 mL tube, the DNA was provided in the mixture ratio of 1:1 (heavy chain DNA:light chain DNA) and mixed with 2 mL of OptiPro™ SFM (Invitrogen) (A). In another 15 mL tube, 100 µL of Freestyle™ MAX reagent and 2 mL of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (IgG2 Fc) was representatively selected for the following examples, and referred as anti-c-Met antibody L3-1Y/IgG2.

Example 1: Measurement of Expression Level of TFF1 in Lung Cancer Cells and Anticancer Effect by an Anti-c-Met Antibody In order to examine the relation between the expression level of TFF1 and the effect of an anti-c-Met antibody in lung cancer cell line, CCLE database was analyzed, to select lung cancer cell lines exhibiting a high level of TFF1 expression. The selected lung cancer cell lines were NCI-H1437, NCI-H1395, NCI-H2110, NCI-H2122, and NCI-H2126. To measure the anticancer effect of an anti-c-Met antibody on the cell lines, 5000 cells of each of the selected cell lines NCI-H1395 (ATCC, CRL-5868), NCI-H1437 (ATCC, CRL-5872), HCI-H2110 (ATCC, CRL-5924), NCI-H2122 (ATCC, CRL-5985), and NCI-H2126 (ATCC, CCL-256), and EBC1 (JCRB, JCRB0820) on which is the anti-c-Met antibody has an anticancer effect, were seeded on 96-well plate and 24 hours after, the antibody L3-1Y/IgG2 was administered thereto at the amount of 0 μg/ml, 0.016 μg/ml, 0.08 μg/ml, 0.4 μg/ml, or 2 μg/ml. 72 hours after the administration of antibody, the cells were counted using CellTiter Glo assay (Promega, G7573), which is a method for measuring an amount of ATP that reflects metabolism of living cells. CellTiter Glo assay contains a substrate which emits luminescence when it reacts with ATP in a cell, and thus, by measuring the luminescence, the number of living cells can be counted. The obtained results are shown in FIG. 1. As shown in FIG. 1, L3-1Y/IgG2 cannot exhibit its anticancer effect on all the examined lung cancer cells, except EBC1 cells.

To examine the relation between such effect of the anti-c-Met antibody and TFF1 expression level, the TFF1 expression levels in EBC1 cell line which is found that L3-1Y/IgG2 has anticancer effect thereon and 5 kinds of lung cancer cell lines (NCI-H1395, NCI-H1437, NCI-H2110, NCI-H2122, and NCI-H2126) which is found that L3-1Y/IgG2 has no anticancer effect thereon, were measured. The measurement of the TFF1 expression level was conducted by measuring the mRNA level using the follow primers.

sense, 5'-cccctggtgcttctatccta-3' (SEQ ID NO: 109);

antisense, 5'-gatccctgcagaagtgtctaaaa-3' (SEQ ID NO: 110).

qPCR for measuring the expression level is conducted by the steps of cell seeding, RNA extraction, cDNA synthesis, and qPCR reaction. For RNA extraction, the cells were seeded on 60 mm dish at the amount of $10^6$ cells/plate and cultured for 2 days. 2 days after, RNA was extracted using RNeasy Mini kit (Qiagen, #74106), wherein the RNA extraction was conducted in 50 μl of RNase free DW. From the RNA extract, 2-3 μg of RNA was collected and cDNA was synthesized from the RNA using Transcriptor First Strand cDNA synthesis kit (Roche, #04 896 866 001). The cDNA synthesis was confirmed according to manufacturer's protocol. qPCR reaction was performed using LC480 SYBR Green I Master (Roche, #04 887 352 001) and LightCycler® 480 Real-Time PCR System (Roche). GAPDH was used as an internal control for correcting the RNA amount of a sample, and qPCR was conducted according to the following steps for all primers: Step1: 95° C., 10 min; Step2 (45 cycles): Step 2-1: 95° C., 10 sec; Step 2-2: 60° C., 20 sec; Step 2-3: 72° C., 20 sec; Step3: 95° C., 5 sec; Step4: 65° C., 1 min; Step5: 95° C., continuous (every 5° C.); Step6: 40° C., 10 sec.

Figure 2:
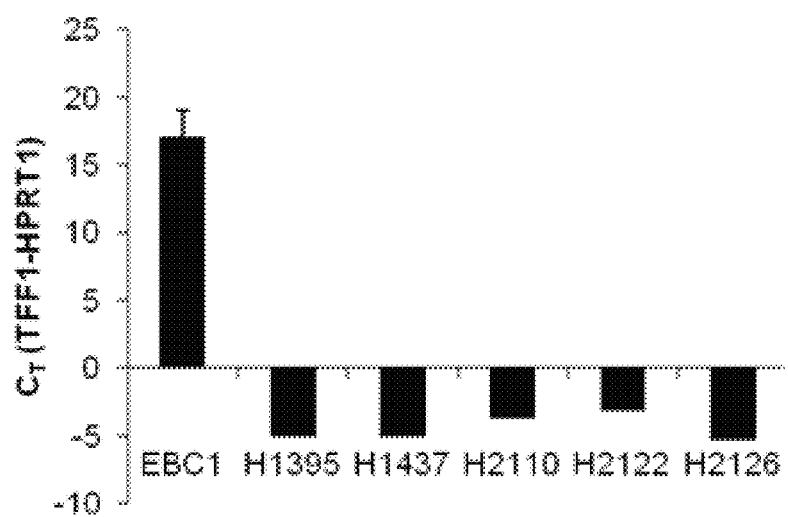
FIG. 2 is a graph showing the level of TFF1 transcript in lung cancer cell lines, which is measured by qPCR and expressed as the difference between $C_T$ values of TFF1 and HPRT1 ($C_T$ value of TFF1-$C_T$ value of HPRT1).

The obtained results are shown in FIG. 2. FIG. 2 shows TFF1 level measured by qPCR, wherein the case that the difference between the $C_T$ values of TFF1 and HPRT1 is great indicates that the TFF1 level is low. As shown in FIG. 2, the TFF1 level in the lung cancer cells on which L3-1Y/IgG2 does not exhibit its effect is considerably higher than that of EBC1 cells on which L3-1Y/IgG2 exhibit its effect.

Example 2: Measurement of TFF1 Expression Level in Anti-c-Met Antibody Resistance Gastric Cancer Cell and Cancer Cell Proliferation Inhibition by Anti-c-Met Antibody To measure the change of TFF1 expression level in a cell where a resistance to an anti-c-Met antibody is induced by repetitive administrations of the antibody, MKN45 gastric cancer cells where a resistance to L3-1Y/IgG2 antibody is induced by repetitive administrations of L3-1Y/IgG2 antibody, was used. The anti-c-Met antibody resistant MKN45 gastric cancer cells were prepared as follows: MKN45 cells (JCRB, JCRB0254) were treated with L3-1Y antibody for 3 months or more with increasing amount of the antibody. The treated amount of L3-1Y/IgG2 was increased starting from the initial concentration of 1 μg/ml to 10 μg/ml, until the resistance to L3-1Y/IgG2 antibody is acquired. To confirm the acquisition of the resistance to L3-1Y/IgG2 antibody, the clones having the acquired resistance to L3-1Y/IgG2 (L3-1Y/IgG2 resistant MKN45) were administered with L3-1Y/IgG2 antibody at the amount of 0 μg/ml, 0.016 μg/ml, 0.08 μg/ml, 0.4 μg/ml, or 2 μg/ml, and 72 hours after, the number of the cells was counted using CellTiter Glo assay (Promega, G7573).

Figure 3:
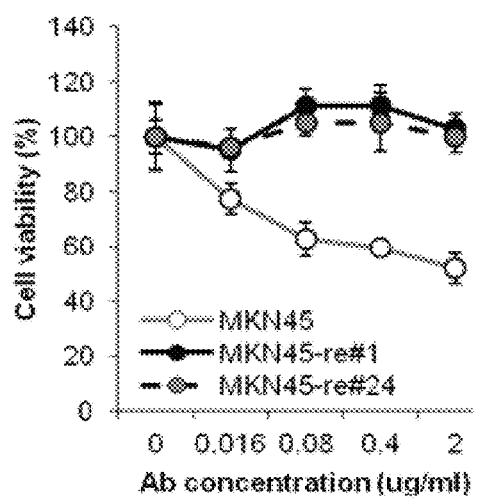
FIG. 3 provides graphs showing the proliferation level (cell viability) of MKN45 cells and anti-c-Met antibody resistance-induced MKN45 cells, when treated with an anti-c-Met antibody.
Figure 3:
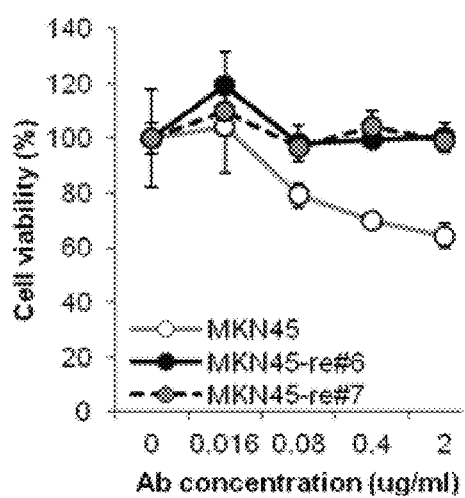

The obtained results are shown in FIG. 3. FIG. 3 includes graphs showing the effect (provided by cell viability) of L3-1Y/IgG2 antibody in MKN45 cells, L3-1Y/IgG2 resistant MKN45 clones #6, #7, #1 and #24 (hereinafter, indicated by MKN45-re#6, MKN45-re#7, MKN45-re#1, and MKN45-re#24, respectively), indicating that L3-1Y/IgG2 antibody exhibits efficacy on MKN45 cells, while it exhibits no efficacy on L3-1Y/IgG2 resistant MKN45 cells.

To examine the difference between TFF1 levels of a MKN45 cell and a L3-1Y/IgG2 resistant MKN45 clone, qPCR was performed. The experiment was carried out as described in Example 1.

Figure 4:
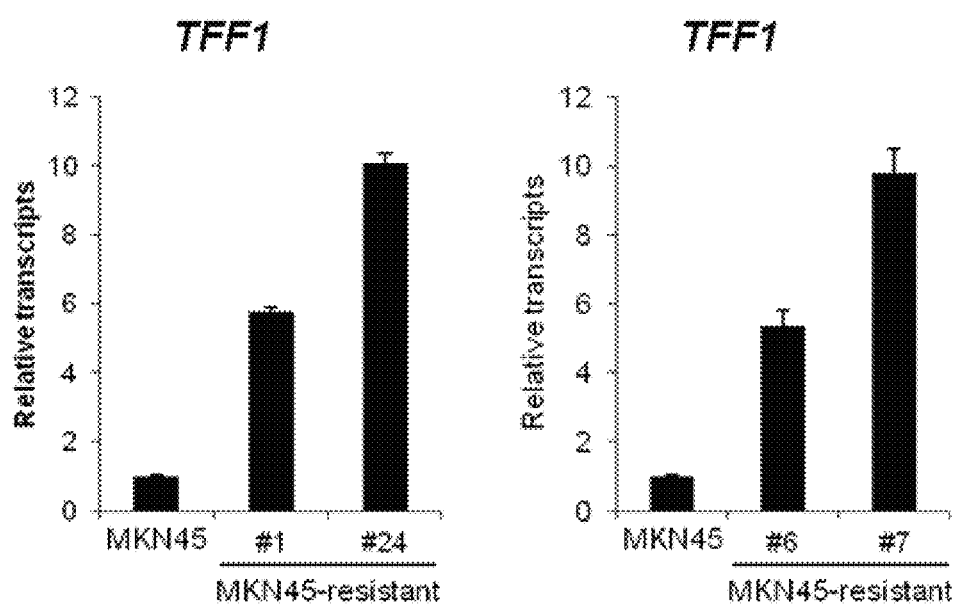
FIG. 4 provides graphs showing the level of TFF1 transcript in MKN45 cells and anti-c-Met antibody resistance-induced MKN45 cells.

The obtained results are shown in FIG. 4. FIG. 4 includes graphs showing the relative TFF1 transcript level of L3-1Y/IgG2 resistant MKN45 clones to that of MKN45 cell. As shown in FIG. 4, the TFF1 transcript level is considerably increased in the L3-1Y/IgG2 resistant MKN45-re-#6, #7, #1, and #24. These results indicate that the efficacy of L3-1Y/IgG2 can be predicted by the transcript level of TFF1.

In addition, to examine whether the resistance to an anti-c-Met antibody induced by repetitive treatment of the antibody can be overcome by treatment of TFF1 siRNA, MKN45-re#24 clone was treated with siRNA. GAPDH siRNA (Dharmacon, Cat. No. D-001830-01) was used as a control siRNA, and TFF1 siRNA (Dharmacon, Cat. No. L-003715-01-0005) was used as a target siRNA. 0.3 μl of RNAiMax (Lifetechnologies) and 40 nM of each siRNA were added to 96-well plate and incubated at room temperature for 15 minutes. The RNAiMax and siRNA were diluted in Opti-MEM so that the total volume reaches 25 μl. 80 μl of MKN45-re#24 cells diluted with 10% FBS supplemented RPMI1640 medium (GIBCO) were seeded in each 96 well, so that 5000 cells are added to each well. 24 hours after the transfection, the medium was removed and 100 μl of a fresh medium where L3-1Y/IgG2 antibody is diluted was treated to the cells. The amount of L3-1Y/IgG2 antibody treated was 0 μg/ml, 0.016 μg/ml, 0.08 μg/ml, 0.4 μg/ml, or 2 μg/ml. 72 hours after, the number of cells was counted using CellTiter Glo assay (Promega, G7573).

The obtained results are shown in FIG. 5. As shown in FIG. 5, when L3-1Y/IgG2 antibody and TFF1 siRNA were co-treated, the cancer cell growth inhibitory effect was observed, while such effect was not observed when L3-1Y/IgG2 antibody was treated alone. These results suggest that the acquired resistance to an anti-c-Met antibody can be overcome by inhibiting TFF1 expression.

Example 3: Measurement of TFF1 Expression Level in Anti-c-Met Antibody Resistance Lung Cancer Cell and Cancer Cell Proliferation Inhibition by Anti-c-Met Antibody To measure the change of TFF1 expression level in a cell where a resistance to an anti-c-Met antibody is induced by repetitive administrations of the antibody, EBC1 lung cancer cells (JCRB, JCRB0820) which were treated with L3-1Y/IgG2 antibody for 3 months or more to acquire a resistance to L3-1Y/IgG2 antibody, were used. The EBC1 lung cancer cells having acquired resistance to L3-1Y/IgG2 antibody were prepared according to Example 2. To confirm the acquisition of the resistance to L3-1Y/IgG2 antibody, the clones having the acquired resistance to L3-1Y/IgG2 (L3-1Y/IgG2 resistant EBC1) were administered with L3-1Y/IgG2 antibody at the amount of 0 µg/ml, 0.016 µg/ml, 0.08 µg/ml, 0.4 µg/ml, or 2 µg/ml, and 72 hours after, the number of the cells was counted using CellTiter Glo assay (Promega, G7573).

Figure 6:
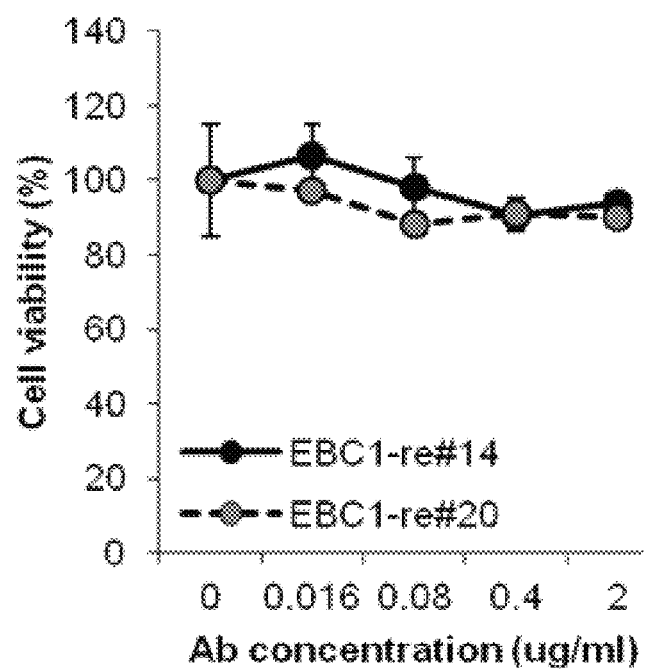
FIG. 6 is a graph showing the proliferation level (cell viability) of anti-c-Met antibody resistance-induced EBC1 cells when treated with an anti-c-Met antibody.

The obtained results are shown in FIG. 6. FIG. 6 is a graph showing the effect (provided by cell viability) of L3-1Y/IgG2 antibody in L3-1Y/IgG2 resistant EBC1 clone #14 and #20 (hereinafter, indicated by EBC1-re#14, and EBC1-re#20, respectively), indicating that L3-1Y/IgG2 antibody exhibits no efficacy on L3-1Y/IgG2 resistant EBC1 cells.

Figure 7:
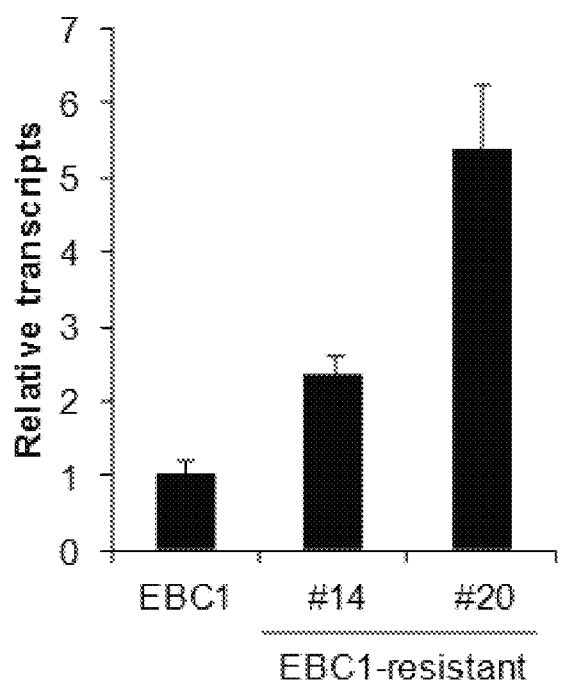
FIG. 7 is a graph showing the level of TFF1 transcript in EBC1 cells and anti-c-Met antibody resistant EBC1 cells.

In addition, referring to Examples 1 and 2, TFF1 mRNA was extracted from EBC1 cells and EBC1-re#14 and #20, and used for examining TFF1 level. The obtained results are shown in FIG. 7. FIG. 7 shows the relative TFF1 transcript level to that of EBC1 cell. As confirmed from FIG. 7, similarly to gastric cancer cells, lung cancer cell line EBC1 also exhibits increased TFF1 level when it acquires resistance to L3-1Y/IgG2.

In addition, to examine whether the resistance to an anti-c-Met antibody induced by repetitive treatment of the antibody can be overcome by treatment of TFF1 siRNA, EBC1-re#20 clone was co-treated with siRNA and an anti-c-Met antibody and the number of the EBC1-re#20 cells was counted referring to Example 2. The obtained results were shown in FIG. 8. Similarly to the results of Example 2, a cancer cell growth inhibitory effect can also be obtained on EBC1 lung cancer cells having acquired resistance to L3-1Y/IgG2 antibody, when L3-1Y/IgG2 and can TFF1 siRNA are co-treated, which is not observed when L3-1Y/IgG2 antibody is treated alone. These results suggest that the acquired resistance to an anti-c-Met antibody can be overcome by inhibiting TFF1 expression.

Example 4: Measurement of TFF1 Protein Level in Serum Using a Xenograft Mouse Model To examine whether TFF1 protein as well as TFF1 gene can act as a marker to an anti-c-Met antibody, TFF1 protein level was measured in serum.

For this experiment, a xenograft model, where lung cancer cells obtained from lung cancer patients (patient-derived lung cancer cells) were grafted, was used. Xenograft mouse models were prepared by grafting patient-derived lung cancer cells into a mouse which was requested to Oncotest GmbH (Freibrug Germany). Patient-derived lung cancer cells (NSCLC), LXFA289, LXFA 400, LXFA 1848, and LXFA 2158 cells were respectively grafted into NMRI nude mice (4-6 week old, female; Harlan) via s.c injection to prepared xenograft mouse models. The preparation of a xenograft mouse model was carried out according to "Subcutaneous implantation" of Oncotest SOP. 10 mice were used per each group.

When the tumor size reaches ~2000 mm$^3$, serum was collected from each mouse model and TFF1 protein level was measured. To minimize the individual difference between the mice, serum was collected from the individuals having median tumor size selected from each group, and used for ELISA. ELISA was conducted using Human Trefoil factor 1 ELISA kit (EIAab, E1049h). In the kit, 1 ml of sample diluent was added to standard, to prepare 10.0 ng/ml stock standard, and then, subjected to ½ dilution, to prepare a standard sample. Mouse serum was also subjected to ½ dilution using sample diluent. Each of the standard sample, blank sample, and the diluted serum sample was added to a well at the amount of 50 µl, and then, detection A solution was added thereto at the amount of 50 µl. The plate was sufficiently stirred so that the reacting materials are well mixed, and incubated at 37° C. for 1 hour. One hour after, a solution was removed and the remaining reacted product was washed three-times with wash buffer (contained in the ELISA kit (EIAab, E1049h)). The washing step was carried out by such manner that the wash buffer was added at the amount of about 300~400 µl, left for 1-2 minutes, and then, removed. Thereafter, detection reagent B solution was added at the amount of 100 µl, left at 37° C. for 45 minutes, and then, washed five-times with the wash buffer. After washing, 90 µl of substrate solution was added and left at 37° C. for 15~30 minutes under the condition of darkness (with no lightening). When proper color is obtained, 50 µl of stop solution was added and the absorbance at 450 nm was measured.

Figure 9:
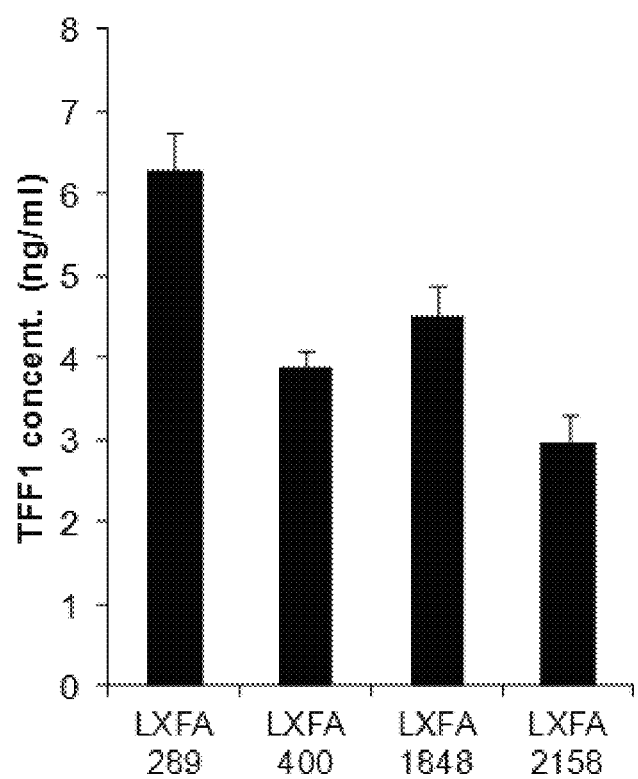
FIG. 9 is a graph showing the expression level of TFF1 protein in serum obtained from a mouse xenograft model.

The concentration that is determined by applying the measured absorbance to the standard was shown in FIG. 9. As shown in FIG. 9, in the serum obtained from the mouse xenograft model to which patient-derived lung cancer cells are grafted, the TFF1 was measured at the detectable range (0.15~10.0 ng/ml), indicating that TFF1 protein can act as a soluble marker. In FIG. 9, LXFA2158 is an efficient group of c-Met inhibitor (L3-1Y/IgG2), and the others are non-efficient groups of c-Met inhibitor (L3-1Y/IgG2). According to the results of FIG. 9, when TFF1 protein is used as a marker under the above experiment conditions, the concentration of TFF1 protein which is a standard to distinguish efficient group and non-efficient group can be determined as about 3 to about 3.5 ng/ml (e.g., if the concentration of TFF1 protein is the above scope or less, the group can be determined as an efficient group, and if the concentration of TFF1 protein is higher than the above scope, the group can be determined as a non-efficient group).

Example 5: Method of Identifying a Subject for Application of a c-Met Inhibitor by Measuring the Levels of c-Met and TFF1

In this experiment, it was examined that mRNA level or protein level of c-Met can be used alone or together with TFF1, for selecting a subject for application of a c-Met inhibitor.

8 xenograft tumor samples (prepared by Oncotest GmbH (Freibrug Germany)) of lung adenocarcinoma were used for this experiment using Affymetrix U133Plus 2.0 array.

Capture and preparation of mRNA was carried out according to the standard protocol of U133 Plus 2.0 array ("GeneChip 3' IVT PLUS Reagent Kit User Manual", the entire disclosure of which is hereby incorporated by reference). After experiment, the data obtained from the DNA chip were subjected to quantile normalization (Bolstad, B. M., Irizarry R. A., Astrand, M, and Speed, T. P. (2003) A Comparison of Normalization Methods for High Density Oligonucleotide Array Data Based on Bias and Variance. Bioinformatics 19(2), pp 185-193), to correct the expression values, and then, the expression value of TFF1 gene was evaluated (Affymetrix probe id: 205009_at). The expression of TFF1 gene can be measured by any other method than the method using the DNA chip as described herein, which is clearly and readily selected by a person skilled in the art.

The obtained results are shown in FIG. 10. In FIG. 10, each spot indicates an individual subject, x axis refers to mRNA expression level of c-Met gene, and y axis refers to mRNA expression level of TFF1 gene, wherein spots 526, 1647, 623, and 2158 indicate efficient groups of c-Met inhibitor L3-1Y/IgG2, spots 923, 1041, 1848, 297, 677, 289, 749, 400, and 983 indicate non-efficient groups of c-Met inhibitor L3-1Y/IgG2, and the other spots indicates absence of data (n=1163). When the expression level of c-Met is high, it is generally expected that a c-Met inhibitor can be exhibit its effect; however, when it is difficult to distinguish efficient group and non-efficient group due to variables such as characteristics of the subject population, limitations of experiment equipment used, and the like, the information of expression level of TFF1 can allow to more exactly analyze and select the subject groups.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of selecting a subject with gastric or lung cancer for treatment with a c-Met inhibitor, the method comprising
measuring in a biological sample from a subject with gastric or lung cancer the level of at least one selected from the group consisting of a TFF1 protein level and a TFF1 mRNA level,
and administering the c-Met inhibitor to the subject if the level of the TFF1 protein or mRNA in the biological sample is lower than that of a reference sample which is obtained from a patient for whom the c-Met inhibitor does not exhibit its effect, wherein the c-Met inhibitor is an anti-c-Met antibody.

2. The method of claim 1, wherein the step of measuring comprises:
adding a material to the biological sample that interacts with the at least one selected from the group consisting of a TFF1 protein and a TFF1 mRNA to form a reaction mixture, wherein the material is a polynucleotide or antibody;
quantifying the level of at least one selected from the group consisting of a TFF1 protein and a TFF1 mRNA in the reaction mixture.

3. The method of claim 1, further comprising measuring the level of at least one selected from the group consisting of c-Met protein and c-Met mRNA in the biological sample.

4. The method of claim 1,
wherein the anti-c-Met antibody is selected from the group consisting of (1) onartuzumab, LY2875358, rilotumumab, and an antibody comprising
a CDR-H1 of SEQ ID NO: 1, a CDR-H2 of SEQ ID NO: 2, a CDR-H3 of SEQ ID NO: 3, a CDR-L1 of SEQ ID NO: 10, a CDR-L2 of SEQ ID NO: 11, and a CDR-L3 of SEQ ID NO: 13,
a CDR-H1 of SEQ ID NO: 1, a CDR-H2 of SEQ ID NO: 2, a CDR-H3 of SEQ ID NO: 3, a CDR-L1 of SEQ ID NO: 106, a CDR-L2 of SEQ ID NO: 11, and a CDR-L3 of SEQ ID NO: 13,
a CDR-H1 of SEQ ID NO: 1, a CDR-H2 of SEQ ID NO: 2, a CDR-H3 of SEQ ID NO: 3, a CDR-L1 of SEQ ID NO: 10, a CDR-L2 of SEQ ID NO: 11, and a CDR-L3 of SEQ ID NO: 12,
a CDR-H1 of SEQ ID NO: 1, a CDR-H2 of SEQ ID NO: 2, a CDR-H3 of SEQ ID NO: 3, a CDR-L1 of SEQ ID NO: 10, a CDR-L2 of SEQ ID NO: 11, and a CDR-L3 of SEQ ID NO: 14,
a CDR-H1 of SEQ ID NO: 1, a CDR-H2 of SEQ ID NO: 2, a CDR-H3 of SEQ ID NO: 3, a CDR-L1 of SEQ ID NO: 10, a CDR-L2 of SEQ ID NO: 11, and a CDR-L3 of SEQ ID NO: 15, or
a CDR-H1 of SEQ ID NO: 1, a CDR-H2 of SEQ ID NO: 2, a CDR-H3 of SEQ ID NO: 3, a CDR-L1 of SEQ ID NO: 10, a CDR-L2 of SEQ ID NO: 11, and a CDR-L3 of SEQ ID NO: 16.

5. The method of claim 1, wherein the measuring step further comprises determining:
i) a ratio of average mRNA expression level of TFF1 gene/average mRNA expression level of GAPDH gene is about 0.59 or less;
ii) a ratio of average mRNA expression level of TFF1 gene/average mRNA expression level of HPRT1 gene is about 1.24 or less; or
iii) a ratio of average mRNA expression level of TFF1 gene/average mRNA expression level of reference genes is about 0.72 or less, wherein the reference genes comprise EEF1A1, RPL23A, TPT1, HUWE1, MATR3, SRSF3, HNRNPC, SMARCA4, WDR90, and TUT1.

6. The method of claim 1, wherein the subject has gastric cancer.

7. The method of claim 1, wherein the subject has lung cancer.

* * * * *